US012642994B2

(12) United States Patent (10) Patent No.: US 12,642,994 B2
Miller et al. (45) Date of Patent: Jun. 2, 2026

(54) HISTOTRIPSY SYSTEMS AND METHODS

(71) Applicant: HistoSonics, Inc., Plymouth, MN (US)

(72) Inventors: Ryan M. Miller, Saline, MI (US);
Viktor Bollen, Chelsea, MI (US);
Carol L. Shaffer, Minnetrista, MN
(US); Carolyn M. Turner,
Minneapolis, MN (US); **Ehsan
Hamtaei**, Ann Arbor, MI (US)

(73) Assignee: HistoSonics, Inc., Plymouth, MN (US)

( * ) Notice: Subject to any disclaimer, the term of this
patent is extended or adjusted under 35
U.S.C. 154(b) by 14 days.

(21) Appl. No.: 18/499,847

(22) Filed: Nov. 1, 2023

(65) Prior Publication Data

US 2024/0139553 A1    May 2, 2024

Related U.S. Application Data

(60) Provisional application No. 63/381,888, filed on Nov.
1, 2022.

(51) Int. Cl.
*A61N 7/02* (2006.01)
*B06B 1/02* (2006.01)
(52) U.S. Cl.
CPC .............. *A61N 7/02* (2013.01); *B06B 1/0215*
(2013.01); *B06B 2201/40* (2013.01); *B06B
2201/76* (2013.01)
(58) Field of Classification Search
CPC .... A61N 7/02; B06B 1/0215; B06B 2201/40;
B06B 2201/76
See application file for complete search history.

(56) References Cited

U.S. PATENT DOCUMENTS

| | | | |
|---|---|---|---|
| 3,243,497 A | 3/1966 | Kendall et al. | |
| 3,679,021 A | 7/1972 | Goldberg et al. | |
| 3,693,415 A | 9/1972 | Whittington | |
| 3,879,699 A | 4/1975 | Pepper | |
| 4,016,749 A | 4/1977 | Wachter | |
| 4,024,501 A | 5/1977 | Herring et al. | |
| 4,051,394 A | 9/1977 | Tieden | |
| 4,114,457 A | 9/1978 | Thun | |
| 4,117,446 A | 9/1978 | Alais | |
| 4,266,747 A | 5/1981 | Souder, Jr. et al. | |
| 4,269,174 A | 5/1981 | Adair | |

(Continued)

FOREIGN PATENT DOCUMENTS

| | | |
|---|---|---|
| AU | 2017222925 B2 | 11/2021 |
| AU | 2023231624 | 9/2024 |

(Continued)

OTHER PUBLICATIONS

International Society for Magnetic Resonance in Medicine (ISMRM);
No. 105; XP040714022;I Jul. 24, 2020.

(Continued)

*Primary Examiner* — Mark D Remaly
(74) *Attorney, Agent, or Firm* — Shay Glenn LLP

(57) ABSTRACT

A histotripsy therapy system configured for the treatment of
tissue is provided, which may include any number of fea-
tures. Provided herein are systems and methods that provide
efficacious non-invasive and minimally invasive therapeu-
tic, diagnostic and research procedures. The systems and
methods herein are configured to measure and display forces
acting upon the therapy treatment head during a procedure.
In some aspects, buoyancy forces from the acoustic coupling
medium are also accounted for.

22 Claims, 32 Drawing Sheets

(56)  References Cited

U.S. PATENT DOCUMENTS

| | | | |
|---|---|---|---|
| 4,277,367 A | 7/1981 | Madsen et al. | |
| 4,351,038 A | 9/1982 | Alais | |
| 4,406,153 A | 9/1983 | Ophir et al. | |
| 4,440,025 A | 4/1984 | Hayakawa et al. | |
| 4,447,031 A | 5/1984 | Souder, Jr. et al. | |
| 4,453,408 A | 6/1984 | Clayman | |
| 4,483,343 A | 11/1984 | Beyer et al. | |
| 4,483,345 A | 11/1984 | Miwa | |
| 4,548,374 A | 10/1985 | Thompson et al. | |
| 4,549,533 A | 10/1985 | Cain et al. | |
| 4,550,606 A | 11/1985 | Drost | |
| 4,551,794 A | 11/1985 | Sandell | |
| 4,575,330 A | 3/1986 | Hull | |
| 4,622,972 A | 11/1986 | Giebeler, Jr. | |
| 4,625,731 A | 12/1986 | Quedens et al. | |
| 4,641,378 A | 2/1987 | McConnell et al. | |
| 4,669,483 A | 6/1987 | Hepp et al. | |
| 4,689,986 A | 9/1987 | Carson et al. | |
| 4,757,820 A | 7/1988 | Itoh | |
| 4,791,915 A | 12/1988 | Barsotti et al. | |
| 4,819,621 A | 4/1989 | Ueberle et al. | |
| 4,829,491 A | 5/1989 | Saugeon et al. | |
| 4,856,107 A | 8/1989 | Dory | |
| 4,865,042 A | 9/1989 | Umemura et al. | |
| 4,888,746 A | 12/1989 | Wurster et al. | |
| 4,890,267 A | 12/1989 | Rudolph | |
| 4,922,917 A | 5/1990 | Dory | |
| 4,928,672 A | 5/1990 | Grasser et al. | |
| 4,938,217 A | 7/1990 | Lele | |
| 4,957,099 A | 9/1990 | Hassler | |
| 4,973,980 A | 11/1990 | Howkins et al. | |
| 4,984,575 A | 1/1991 | Uchiyama et al. | |
| 4,991,151 A | 2/1991 | Dory | |
| 4,995,012 A | 2/1991 | Dory | |
| RE33,590 E | 5/1991 | Dory | |
| 5,014,686 A | 5/1991 | Schafer | |
| 5,065,751 A | 11/1991 | Wolf | |
| 5,078,140 A | 1/1992 | Kwoh | |
| 5,080,101 A | 1/1992 | Dory | |
| 5,080,102 A | 1/1992 | Dory | |
| 5,091,893 A | 2/1992 | Smith et al. | |
| 5,092,336 A | 3/1992 | Fink | |
| 5,097,709 A | 3/1992 | Masuzawa et al. | |
| 5,111,822 A | 5/1992 | Dory | |
| 5,143,073 A | 9/1992 | Dory | |
| 5,143,074 A | 9/1992 | Dory | |
| 5,150,711 A | 9/1992 | Dory | |
| 5,158,070 A | 10/1992 | Dory | |
| 5,158,071 A | 10/1992 | Umemura et al. | |
| 5,163,421 A | 11/1992 | Bernstein et al. | |
| 5,165,412 A | 11/1992 | Okazaki | |
| 5,174,294 A | 12/1992 | Saito et al. | |
| 5,195,509 A | 3/1993 | Rentschler et al. | |
| 5,209,221 A | 5/1993 | Riedlinger | |
| 5,215,680 A | 6/1993 | D'Arrigo | |
| 5,219,401 A | 6/1993 | Cathignol et al. | |
| 5,222,806 A | 6/1993 | Roberts | |
| 5,230,340 A | 7/1993 | Rhyne | |
| 5,295,484 A | 3/1994 | Marcus et al. | |
| 5,316,000 A | 5/1994 | Chapelon et al. | |
| 5,354,258 A | 10/1994 | Dory | |
| 5,380,411 A | 1/1995 | Schlief | |
| 5,393,296 A | 2/1995 | Rattner | |
| 5,409,002 A | 4/1995 | Pell | |
| 5,431,621 A | 7/1995 | Dory | |
| 5,435,311 A | 7/1995 | Umemura et al. | |
| 5,443,069 A | 8/1995 | Schaetzle | |
| 5,450,305 A | 9/1995 | Boys et al. | |
| 5,469,852 A | 11/1995 | Nakamura et al. | |
| 5,474,071 A | 12/1995 | Chapelon et al. | |
| 5,474,531 A | 12/1995 | Carter | |
| 5,490,051 A | 2/1996 | Messana | |
| 5,492,126 A | 2/1996 | Hennige et al. | |
| 5,501,655 A | 3/1996 | Rolt et al. | |
| 5,520,188 A | 5/1996 | Hennige et al. | |
| 5,523,058 A | 6/1996 | Umemura et al. | |
| 5,524,620 A | 6/1996 | Rosenschein | |
| 5,524,875 A | 6/1996 | Thommen, Jr. | |
| 5,540,909 A | 7/1996 | Schutt | |
| 5,542,935 A | 8/1996 | Unger et al. | |
| 5,558,092 A | 9/1996 | Unger et al. | |
| 5,563,346 A | 10/1996 | Bartelt et al. | |
| 5,566,675 A | 10/1996 | Li et al. | |
| 5,573,497 A | 11/1996 | Chapelon | |
| 5,580,575 A | 12/1996 | Unger et al. | |
| 5,582,578 A | 12/1996 | Zhong et al. | |
| 5,590,657 A | 1/1997 | Cain et al. | |
| 5,601,526 A | 2/1997 | Chapelon et al. | |
| 5,617,862 A | 4/1997 | Cole et al. | |
| 5,648,098 A | 7/1997 | Porter | |
| 5,665,054 A | 9/1997 | Dory | |
| 5,666,954 A | 9/1997 | Chapelon et al. | |
| 5,676,452 A | 10/1997 | Scholz | |
| 5,676,692 A | 10/1997 | Sanghvi et al. | |
| 5,678,554 A | 10/1997 | Hossack et al. | |
| 5,683,064 A | 11/1997 | Copeland et al. | |
| 5,694,936 A | 12/1997 | Fujimoto et al. | |
| 5,695,460 A | 12/1997 | Siegel et al. | |
| 5,717,657 A | 2/1998 | Ruffa | |
| 5,720,287 A | 2/1998 | Chapelon et al. | |
| 5,724,972 A | 3/1998 | Petrofsky | |
| 5,743,863 A | 4/1998 | Chapelon | |
| 5,753,929 A | 5/1998 | Bliss | |
| 5,759,162 A | 6/1998 | Oppelt et al. | |
| 5,766,138 A | 6/1998 | Rattner | |
| 5,769,790 A | 6/1998 | Watkins et al. | |
| 5,797,848 A | 8/1998 | Marian et al. | |
| 5,800,365 A | 9/1998 | Zhong et al. | |
| 5,820,623 A | 10/1998 | Ng | |
| 5,823,962 A | 10/1998 | Schaetzle et al. | |
| 5,827,204 A | 10/1998 | Grandia et al. | |
| 5,836,896 A | 11/1998 | Rosenschein | |
| 5,849,727 A | 12/1998 | Porter et al. | |
| 5,873,902 A | 2/1999 | Sanghvi et al. | |
| 5,879,314 A | 3/1999 | Peterson et al. | |
| 5,928,169 A | 7/1999 | Schitzle et al. | |
| 5,932,807 A | 8/1999 | Mallart | |
| 5,947,904 A | 9/1999 | Hossack et al. | |
| 6,001,069 A | 12/1999 | Tachibana et al. | |
| 6,007,499 A | 12/1999 | Martin et al. | |
| 6,022,309 A | 2/2000 | Celliers et al. | |
| 6,036,667 A | 3/2000 | Manna et al. | |
| 6,065,166 A | 5/2000 | Sharrock et al. | |
| 6,088,613 A | 7/2000 | Inger | |
| 6,093,883 A | 7/2000 | Sanghvi et al. | |
| 6,113,558 A | 9/2000 | Rosenschein et al. | |
| 6,126,607 A | 10/2000 | Whitmore, III et al. | |
| 6,128,958 A | 10/2000 | Cain | |
| 6,143,018 A | 11/2000 | Beuthan et al. | |
| 6,165,144 A | 12/2000 | Talish et al. | |
| 6,176,842 B1 | 1/2001 | Tachibana et al. | |
| 6,296,619 B1 | 10/2001 | Brisken et al. | |
| 6,308,585 B1 | 10/2001 | Nilsson et al. | |
| 6,308,710 B1 | 10/2001 | Silva | |
| 6,309,355 B1 | 10/2001 | Cain et al. | |
| 6,318,146 B1 | 11/2001 | Madsen et al. | |
| 6,321,109 B2 | 11/2001 | Ben-Haim et al. | |
| 6,338,566 B1 | 1/2002 | Verdier | |
| 6,344,489 B1 | 2/2002 | Spears | |
| 6,391,020 B1 | 5/2002 | Kurtz et al. | |
| 6,413,216 B1 | 7/2002 | Cain et al. | |
| 6,419,648 B1 | 7/2002 | Vitek et al. | |
| 6,424,885 B1 | 7/2002 | Niemeyer et al. | |
| 6,470,204 B1 | 10/2002 | Uzgiris et al. | |
| 6,488,639 B1 | 12/2002 | Ribault et al. | |
| 6,490,469 B2 | 12/2002 | Candy | |
| 6,500,141 B1 | 12/2002 | Irion et al. | |
| 6,506,154 B1 | 1/2003 | Ezion et al. | |
| 6,506,171 B1 | 1/2003 | Vitek et al. | |
| 6,508,774 B1 | 1/2003 | Acker et al. | |
| 6,511,428 B1 | 1/2003 | Azuma et al. | |
| 6,511,444 B2 | 1/2003 | Hynynen et al. | |
| 6,522,142 B1 | 2/2003 | Freundlich | |
| 6,524,251 B2 | 2/2003 | Rabiner et al. | |

(56) References Cited

U.S. PATENT DOCUMENTS

| | | | |
|---|---|---|---|
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unge |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,773,401 B1 | 8/2004 | Dreschel et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckal et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,175,599 B2 | 2/2007 | Hynynen et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,429,249 B1 | 9/2008 | Winder et al. |
| 7,431,704 B2 | 10/2008 | Babaev |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 7,695,437 B2 | 4/2010 | Quistgaard et al. |
| 7,714,481 B2 | 5/2010 | Sakai |
| 7,771,359 B2 | 8/2010 | Adam |
| 7,967,763 B2 | 6/2011 | Deem et al. |
| 8,057,408 B2 | 11/2011 | Cain et al. |
| 8,295,912 B2 | 10/2012 | Gertner |
| 8,333,115 B1 | 12/2012 | Garvey et al. |
| 8,337,407 B2 | 12/2012 | Quistgaard et al. |
| 8,342,467 B2 | 1/2013 | Stachowski et al. |
| 8,376,970 B2 | 2/2013 | Babaev |
| 8,539,813 B2 | 9/2013 | Cain et al. |
| 8,568,339 B2 | 10/2013 | Rybyanets |
| 8,636,664 B2 | 1/2014 | Brannan |
| 8,715,187 B2 | 5/2014 | Landberg Davis et al. |
| 8,845,537 B2 | 9/2014 | Tanaka et al. |
| 8,932,239 B2 | 1/2015 | Sokka et al. |
| 9,028,434 B2 | 5/2015 | Tanaka |
| 9,049,783 B2 | 6/2015 | Teofilovic |
| 9,061,131 B2 | 6/2015 | Jahnke et al. |
| 9,144,694 B2 | 9/2015 | Cain |
| 9,220,476 B2 | 12/2015 | Coussios et al. |
| 9,228,730 B1 | 1/2016 | Inbody |
| 9,302,124 B2 | 4/2016 | Konofagou et al. |
| 9,457,201 B2 | 10/2016 | Hoelscher et al. |
| 9,526,923 B2 | 12/2016 | Jahnke et al. |
| 9,636,133 B2 | 5/2017 | Hall et al. |
| 9,642,634 B2 | 5/2017 | Cain et al. |
| 9,763,688 B2 | 9/2017 | Stulen et al. |
| 9,901,753 B2 | 2/2018 | Cain et al. |
| 9,943,708 B2 | 4/2018 | Roberts et al. |
| 10,022,107 B2 | 7/2018 | Thornton et al. |
| 10,046,179 B2 | 8/2018 | Oskar-Kohler |
| 10,046,181 B2 | 8/2018 | Barthe et al. |
| 10,058,352 B2 | 8/2018 | Carvell et al. |
| 10,071,266 B2 | 9/2018 | Cain |
| 10,130,828 B2 | 11/2018 | Vortman et al. |
| 10,219,815 B2 | 3/2019 | Maxwell et al. |
| 10,293,187 B2 | 5/2019 | Cannata et al. |
| 10,293,374 B2 | 5/2019 | Torashima et al. |
| 10,751,015 B2 | 8/2020 | Anderson et al. |
| 10,751,125 B2 | 8/2020 | Levy et al. |
| 10,765,892 B1 | 9/2020 | Vitek et al. |
| 10,772,646 B2 | 9/2020 | Lu et al. |
| 10,780,298 B2 | 9/2020 | Cain et al. |
| 10,791,991 B2 | 10/2020 | Burkett et al. |
| 10,799,209 B2 | 10/2020 | Lahti et al. |
| 10,806,421 B2 | 10/2020 | Keller |
| 10,820,813 B2 | 11/2020 | Alpert |
| 10,847,264 B2 | 11/2020 | Mansker et al. |
| 10,849,511 B2 | 12/2020 | Tochterman et al. |
| 10,869,603 B2 | 12/2020 | Millett et al. |
| 10,869,633 B2 | 12/2020 | Burkett |
| 10,869,648 B2 | 12/2020 | Hubbard et al. |
| 10,874,353 B2 | 12/2020 | Assif |
| 10,874,409 B2 | 12/2020 | Matsubara et al. |
| 10,878,586 B2 | 12/2020 | Brokman et al. |
| 10,888,232 B2 | 1/2021 | Anderson et al. |
| 10,893,808 B2 | 1/2021 | Dorando |
| 10,900,933 B2 | 1/2021 | Prus et al. |
| 10,905,394 B2 | 2/2021 | Stigall et al. |
| 10,912,463 B2 | 2/2021 | Davies et al. |
| 10,925,688 B2 | 2/2021 | Millett et al. |
| 10,927,003 B2 | 2/2021 | Millett et al. |
| 10,932,678 B2 | 3/2021 | Burkett |
| 10,939,826 B2 | 3/2021 | Glynn et al. |
| 10,942,022 B2 | 3/2021 | Johansson et al. |
| 10,973,419 B2 | 4/2021 | Corl |
| 10,993,618 B2 | 5/2021 | Mansker et al. |
| 10,993,628 B2 | 5/2021 | Tochterman |
| 10,993,694 B2 | 5/2021 | Meyer et al. |
| 11,000,185 B2 | 5/2021 | Stigall et al. |
| 11,006,840 B2 | 5/2021 | Stigall |
| 11,013,491 B2 | 5/2021 | Rice et al. |
| 11,020,087 B2 | 6/2021 | Hoffman |
| 11,020,089 B2 | 6/2021 | Cort |
| 11,026,591 B2 | 6/2021 | Burkett et al. |
| 11,040,140 B2 | 6/2021 | Unser et al. |
| 11,058,399 B2 | 7/2021 | Xu et al. |
| 11,071,522 B2 | 7/2021 | Hynynen et al. |
| 11,103,731 B2 | 8/2021 | Vortman et al. |
| 11,112,473 B2 | 9/2021 | Assif |
| 11,119,552 B2 | 9/2021 | Spencer et al. |
| 11,120,896 B2 | 9/2021 | Balignasay et al. |
| 11,123,019 B2 | 9/2021 | Merritt et al. |
| 11,123,575 B2 | 9/2021 | Vortman et al. |
| 11,135,454 B2 | 10/2021 | Xu et al. |
| 11,141,063 B2 | 10/2021 | Kemp et al. |
| 11,141,131 B2 | 10/2021 | Stigall et al. |
| 11,160,513 B2 | 11/2021 | Anderson et al. |
| 11,205,507 B2 | 12/2021 | Anderson et al. |
| 11,219,748 B2 | 1/2022 | Burkett et al. |
| 11,224,349 B2 | 1/2022 | Davies et al. |
| 11,224,403 B2 | 1/2022 | Cort |
| 11,224,407 B2 | 1/2022 | Wrolstad et al. |

(56) References Cited

U.S. PATENT DOCUMENTS

| | | | |
|---|---|---|---|
| 11,234,649 B2 | 2/2022 | Matsubara et al. |
| 11,246,533 B2 | 2/2022 | Henderson et al. |
| 11,246,565 B2 | 2/2022 | Corl |
| 11,253,225 B2 | 2/2022 | Hancock et al. |
| 11,260,160 B2 | 3/2022 | Matsubara et al. |
| 11,272,845 B2 | 3/2022 | Cheline et al. |
| 11,272,904 B2 | 3/2022 | Vortman et al. |
| 11,291,866 B2 | 4/2022 | Levy et al. |
| 11,298,030 B2 | 4/2022 | Davies et al. |
| 11,309,071 B2 | 4/2022 | Anderson |
| 11,311,271 B2 | 4/2022 | Stigall et al. |
| 11,324,410 B2 | 5/2022 | Burkett |
| 11,350,906 B2 | 6/2022 | Castella et al. |
| 11,350,954 B2 | 6/2022 | De Cicco et al. |
| 11,364,042 B2 | 6/2022 | Maxwell et al. |
| 11,369,346 B2 | 6/2022 | De Cicco et al. |
| 11,369,994 B2 | 6/2022 | Greenberg et al. |
| 11,395,638 B2 | 7/2022 | Shin et al. |
| 11,406,334 B2 | 8/2022 | Merritt |
| 11,406,355 B2 | 8/2022 | Hoffman et al. |
| 11,406,498 B2 | 8/2022 | Stigall et al. |
| 11,408,987 B2 | 8/2022 | Vignon et al. |
| 11,413,017 B2 | 8/2022 | Stigall et al. |
| 11,419,580 B2 | 8/2022 | Stigall et al. |
| 11,426,140 B2 | 8/2022 | Sudol et al. |
| 11,432,795 B2 | 9/2022 | Merritt |
| 11,432,900 B2 | 9/2022 | Rakic et al. |
| 11,446,000 B2 | 9/2022 | Minas et al. |
| 11,452,496 B2 | 9/2022 | Minas et al. |
| 11,452,506 B2 | 9/2022 | Perez et al. |
| 11,471,215 B2 | 10/2022 | Stigall et al. |
| 11,484,294 B2 | 11/2022 | Hancock et al. |
| 11,510,632 B2 | 11/2022 | Begin et al. |
| 11,517,291 B2 | 12/2022 | Kantor et al. |
| 11,520,874 B2 | 12/2022 | Kennedy et al. |
| 11,524,183 B1 | 12/2022 | Garcia Gutierrez et al. |
| 11,527,001 B2 | 12/2022 | Brokman et al. |
| 11,547,389 B2 | 1/2023 | Shin et al. |
| 11,553,889 B2 | 1/2023 | Spencer et al. |
| 11,554,386 B2 | 1/2023 | Pernot et al. |
| 11,559,207 B2 | 1/2023 | Stigall et al. |
| 11,567,153 B2 | 1/2023 | Stormont et al. |
| 11,576,649 B2 | 2/2023 | Corl |
| 11,576,652 B2 | 2/2023 | De Cicco et al. |
| 11,583,193 B2 | 2/2023 | Groenland et al. |
| 11,589,835 B2 | 2/2023 | Stigall et al. |
| 11,596,351 B2 | 3/2023 | Nair |
| 11,596,384 B2 | 3/2023 | Nair et al. |
| 11,596,385 B2 | 3/2023 | Stigall et al. |
| 11,596,387 B2 | 3/2023 | Song |
| 11,596,389 B2 | 3/2023 | Nair |
| 11,596,469 B2 | 3/2023 | Nair |
| 11,622,746 B2 | 4/2023 | Minas et al. |
| 11,638,576 B2 | 5/2023 | Groenland et al. |
| 11,647,989 B2 | 5/2023 | Hope Simpson et al. |
| 11,648,424 B2 | 5/2023 | Cannata et al. |
| 11,653,895 B2 | 5/2023 | Stigall et al. |
| 11,660,070 B2 | 5/2023 | Stigall et al. |
| 11,666,245 B2 | 6/2023 | Rajguru et al. |
| 11,666,307 B2 | 6/2023 | Unser |
| 11,672,433 B2 | 6/2023 | Park et al. |
| 11,672,552 B2 | 6/2023 | Pasquino et al. |
| 11,672,953 B2 | 6/2023 | May |
| 11,684,342 B2 | 6/2023 | Groenland et al. |
| 11,684,807 B2 | 6/2023 | Vortman et al. |
| 11,701,134 B2 | 7/2023 | Maxwell et al. |
| 11,707,207 B2 | 7/2023 | Stigall et al. |
| 11,707,254 B2 | 7/2023 | Di Tullio et al. |
| 11,733,881 B2 | 8/2023 | Perez |
| 11,737,728 B2 | 8/2023 | Davies et al. |
| 11,744,527 B2 | 9/2023 | Scott et al. |
| 11,744,547 B2 | 9/2023 | Hynynen |
| 11,759,169 B2 | 9/2023 | Cort |
| 11,759,174 B2 | 9/2023 | Saroha et al. |
| 11,766,237 B2 | 9/2023 | Anderson |
| 11,771,370 B2 | 10/2023 | Hynynen |
| 11,771,405 B2 | 10/2023 | Rhodes |
| 11,771,869 B2 | 10/2023 | Cicco |
| 11,779,307 B2 | 10/2023 | Norris et al. |
| 11,806,167 B2 | 11/2023 | Burkett |
| 11,813,484 B2 | 11/2023 | Cannata et al. |
| 11,813,485 B2 | 11/2023 | Xu et al. |
| 11,819,712 B2 | 11/2023 | Cain et al. |
| 11,854,687 B2 | 12/2023 | Keller |
| 11,857,362 B2 | 1/2024 | Wrolstad et al. |
| 11,857,807 B2 | 1/2024 | Levy et al. |
| 11,864,918 B2 | 1/2024 | Burkett et al. |
| 11,872,412 B2 | 1/2024 | Vortman et al. |
| 11,879,973 B2 | 1/2024 | Prus et al. |
| 11,883,235 B2 | 1/2024 | Stigall et al. |
| 11,890,025 B2 | 2/2024 | Stigall et al. |
| 11,890,136 B2 | 2/2024 | Stigall et al. |
| 11,890,137 B2 | 2/2024 | Jenkins et al. |
| 11,950,954 B2 | 4/2024 | Hyun et al. |
| 11,963,822 B2 | 4/2024 | Wrolstad |
| 11,986,682 B2 | 5/2024 | Prus et al. |
| 11,992,366 B2 | 5/2024 | Stigall et al. |
| 12,017,013 B2 | 6/2024 | Sasamine et al. |
| 12,035,919 B2 | 7/2024 | Unser |
| 12,036,066 B2 | 7/2024 | De Cicco et al. |
| 12,053,194 B2 | 8/2024 | Goertz et al. |
| 12,082,970 B2 | 9/2024 | Goodman |
| 12,096,949 B2 | 9/2024 | Fermi et al. |
| 12,097,072 B2 | 9/2024 | Stigall et al. |
| 12,112,850 B2 | 10/2024 | Kuo et al. |
| 12,115,007 B2 | 10/2024 | Merritt et al. |
| 12,144,677 B2 | 11/2024 | Corl |
| 12,167,931 B2 | 12/2024 | Cort |
| 12,178,642 B2 | 12/2024 | Rajguru et al. |
| 12,178,643 B2 | 12/2024 | Stigall et al. |
| 12,186,130 B2 | 1/2025 | Davies |
| 12,220,259 B2 | 2/2025 | Burkett et al. |
| 12,232,907 B2 | 2/2025 | Chao et al. |
| 12,246,195 B2 | 3/2025 | Levy et al. |
| 12,257,461 B2 | 3/2025 | Son et al. |
| 12,263,035 B2 | 4/2025 | Stigall et al. |
| 12,295,600 B2 | 5/2025 | Stigall et al. |
| 12,303,327 B2 | 5/2025 | Stigall et al. |
| 12,343,198 B2 | 7/2025 | Laroya |
| 12,402,802 B2 | 9/2025 | Vitek et al. |
| 12,419,607 B2 | 9/2025 | Rajguru et al. |
| 12,440,188 B2 | 10/2025 | Chao et al. |
| 12,465,477 B2 | 11/2025 | Pasquino et al. |
| 12,490,936 B2 | 12/2025 | Corl |
| 2001/0039420 A1 | 11/2001 | Burbank et al. |
| 2001/0041163 A1 | 11/2001 | Sugita et al. |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2002/0145091 A1 | 10/2002 | Talish et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0169591 A1 | 9/2003 | Cochran |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0162571 A1 | 8/2004 | Rabiner et al. |
| 2004/0164213 A1 | 8/2004 | Stephan |
| 2004/0236248 A1 | 11/2004 | Svedman |
| 2004/0243021 A1 | 12/2004 | Murphy et al. |
| 2004/0249509 A1 | 12/2004 | Rogers et al. |
| 2004/0260214 A1 | 12/2004 | Echt et al. |
| 2005/0011296 A1 | 1/2005 | Koseki |
| 2005/0020945 A1 | 1/2005 | Tosaya et al. |
| 2005/0028289 A1 | 2/2005 | Hakamiun |
| 2005/0038339 A1 | 2/2005 | Chauhan et al. |
| 2005/0038361 A1 | 2/2005 | Zhong et al. |
| 2005/0121734 A1 | 6/2005 | Degertekin et al. |
| 2005/0152561 A1 | 7/2005 | Spencer |

(56) References Cited

U.S. PATENT DOCUMENTS

| | | |
|---|---|---|
| 2005/0154314 A1 | 7/2005 | Quistgaard |
| 2005/0154431 A1 | 7/2005 | Quistgaard et al. |
| 2005/0203399 A1 | 9/2005 | Vaezy et al. |
| 2005/0215901 A1 | 9/2005 | Anderson et al. |
| 2005/0234438 A1 | 10/2005 | Mast et al. |
| 2005/0283098 A1 | 12/2005 | Conston et al. |
| 2006/0058678 A1 | 3/2006 | Vitek et al. |
| 2006/0060991 A1 | 3/2006 | Holsteyns et al. |
| 2006/0074303 A1 | 4/2006 | Chornenky et al. |
| 2006/0089636 A1 | 4/2006 | Christopherson et al. |
| 2006/0173321 A1 | 8/2006 | Kubota et al. |
| 2006/0173387 A1 | 8/2006 | Hansmann et al. |
| 2006/0184166 A1 | 8/2006 | Valle et al. |
| 2006/0206028 A1 | 9/2006 | Lee et al. |
| 2006/0229659 A1 | 10/2006 | Gifford et al. |
| 2006/0241466 A1 | 10/2006 | Ottoboni et al. |
| 2006/0241523 A1 | 10/2006 | Sinelnikov et al. |
| 2006/0241533 A1 | 10/2006 | Geller |
| 2006/0264760 A1 | 11/2006 | Liu et al. |
| 2006/0293598 A1 | 12/2006 | Fraser |
| 2006/0293630 A1 | 12/2006 | Manna et al. |
| 2007/0004984 A1 | 1/2007 | Crum et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1 | 4/2007 | Cain et al. |
| 2007/0140413 A1 | 6/2007 | Saracen |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2007/0239001 A1 | 10/2007 | Mehl et al. |
| 2007/0270683 A1 | 11/2007 | Meloy |
| 2007/0293762 A1 | 12/2007 | Sawada et al. |
| 2008/0013593 A1 | 1/2008 | Kawabata |
| 2008/0033297 A1 | 2/2008 | Sliwa |
| 2008/0033417 A1 | 2/2008 | Nields et al. |
| 2008/0051656 A1 | 2/2008 | Vaezy et al. |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0154132 A1 | 6/2008 | Hall et al. |
| 2008/0167555 A1 | 7/2008 | Qian et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0269614 A1 | 10/2008 | Adachi et al. |
| 2008/0283303 A1 | 11/2008 | Cote |
| 2008/0300485 A1 | 12/2008 | Liu et al. |
| 2008/0312561 A1 | 12/2008 | Chauhan |
| 2008/0319376 A1 | 12/2008 | Wilcox et al. |
| 2009/0012514 A1 | 1/2009 | Moonen et al. |
| 2009/0030339 A1 | 1/2009 | Cheng et al. |
| 2009/0036773 A1 | 2/2009 | Lau et al. |
| 2009/0112098 A1 | 4/2009 | Vaezy et al. |
| 2009/0171254 A1 | 7/2009 | Kushculey et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2009/0230823 A1 | 9/2009 | Kushculey et al. |
| 2009/0254008 A1 | 10/2009 | Shields, Jr. |
| 2009/0287083 A1 | 11/2009 | Kushculey et al. |
| 2009/0306502 A1 | 12/2009 | Lacoste |
| 2010/0011845 A1 | 1/2010 | Laugharn et al. |
| 2010/0042020 A1 | 2/2010 | Ben-Ezra |
| 2010/0056924 A1 | 3/2010 | Powers |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0204578 A1 | 8/2010 | Schmidt et al. |
| 2010/0251823 A1 | 10/2010 | Adachi et al. |
| 2010/0255623 A1 | 10/2010 | Huang |
| 2010/0261994 A1 | 10/2010 | Davalos et al. |
| 2010/0274136 A1 | 10/2010 | Cerofolini |
| 2010/0280374 A1 | 11/2010 | Roberts et al. |
| 2010/0286518 A1 | 11/2010 | Lee et al. |
| 2010/0286519 A1 | 11/2010 | Lee et al. |
| 2010/0298744 A1 | 11/2010 | Altshuler et al. |
| 2010/0305432 A1 | 12/2010 | Duhay et al. |
| 2010/0317971 A1 | 12/2010 | Fan et al. |
| 2010/0318002 A1 | 12/2010 | Prus et al. |
| 2011/0072970 A1 | 3/2011 | Slobodzian et al. |
| 2011/0112400 A1 | 5/2011 | Emery et al. |
| 2011/0118600 A1 | 5/2011 | Gertner |
| 2011/0118602 A1 | 5/2011 | Weng et al. |
| 2011/0144490 A1 | 6/2011 | Davis et al. |
| 2011/0144545 A1 | 6/2011 | Fan et al. |
| 2011/0172529 A1 | 7/2011 | Gertner |
| 2011/0178444 A1 | 7/2011 | Slayton et al. |
| 2011/0208059 A1 | 8/2011 | Cerofolini |
| 2011/0245671 A1 | 10/2011 | Sato |
| 2011/0251528 A1 | 10/2011 | Canney et al. |
| 2011/0257524 A1 | 10/2011 | Gertner |
| 2011/0257561 A1 | 10/2011 | Gertner et al. |
| 2011/0263967 A1 | 10/2011 | Bailey et al. |
| 2011/0270136 A1 | 11/2011 | Vitek et al. |
| 2011/0302719 A1 | 12/2011 | Schwirian et al. |
| 2011/0319765 A1 | 12/2011 | Gertner |
| 2011/0319927 A1 | 12/2011 | Nita |
| 2012/0029337 A1 | 2/2012 | Aoyagi |
| 2012/0029353 A1 | 2/2012 | Slayton et al. |
| 2012/0029393 A1 | 2/2012 | Lee |
| 2012/0046592 A1 | 2/2012 | Albright et al. |
| 2012/0059264 A1 | 3/2012 | Hope Simpson et al. |
| 2012/0059285 A1 | 3/2012 | Soltani et al. |
| 2012/0065492 A1 | 3/2012 | Gertner et al. |
| 2012/0065493 A1 | 3/2012 | Gertner |
| 2012/0065494 A1 | 3/2012 | Gertner et al. |
| 2012/0092724 A1 | 4/2012 | Pettis |
| 2012/0101412 A1 | 4/2012 | Vortman et al. |
| 2012/0111339 A1 | 5/2012 | Barthe et al. |
| 2012/0130288 A1 | 5/2012 | Holland et al. |
| 2012/0136279 A1 | 5/2012 | Tanaka et al. |
| 2012/0158013 A1 | 6/2012 | Stefanchik et al. |
| 2012/0172720 A1 | 7/2012 | Asami et al. |
| 2012/0189998 A1 | 7/2012 | Kruecker et al. |
| 2012/0215157 A1 | 8/2012 | Berryman et al. |
| 2012/0232388 A1 | 9/2012 | Curra et al. |
| 2012/0253176 A1 | 10/2012 | Dumoulin |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2012/0281902 A1 | 11/2012 | Oikawa et al. |
| 2013/0051178 A1 | 2/2013 | Rybyanets |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0144165 A1 | 6/2013 | Ebbini et al. |
| 2013/0172739 A1 | 7/2013 | Paladini |
| 2013/0190623 A1 | 7/2013 | Bertolina et al. |
| 2013/0190661 A1 | 7/2013 | Wing et al. |
| 2013/0255426 A1 | 10/2013 | Kassow et al. |
| 2013/0257224 A1 | 10/2013 | Wodnicki et al. |
| 2013/0261467 A1 | 10/2013 | Dausch et al. |
| 2013/0267853 A1 | 10/2013 | Dausch et al. |
| 2013/0303906 A1 | 11/2013 | Cain et al. |
| 2014/0005521 A1 | 1/2014 | Kohler et al. |
| 2014/0030806 A1 | 1/2014 | Dudley et al. |
| 2014/0039358 A1 | 2/2014 | Zhou et al. |
| 2014/0046181 A1 | 2/2014 | Benchimol et al. |
| 2014/0058293 A1 | 2/2014 | Hynynen et al. |
| 2014/0058294 A1 | 2/2014 | Gross et al. |
| 2014/0073995 A1 | 3/2014 | Teofilovic et al. |
| 2014/0074076 A1 | 3/2014 | Gertner |
| 2014/0088613 A1 | 3/2014 | Seo et al. |
| 2014/0100459 A1 | 4/2014 | Xu et al. |
| 2014/0112107 A1 | 4/2014 | Guo et al. |

(56)　　　　References Cited

U.S. PATENT DOCUMENTS

| | | |
|---|---|---|
| 2014/0128734 A1 | 5/2014 | Genstler et al. |
| 2014/0180072 A1 | 6/2014 | Davies |
| 2014/0180273 A1 | 6/2014 | Nair |
| 2014/0200489 A1 | 7/2014 | Behar et al. |
| 2014/0243664 A1 | 8/2014 | El-Sayed et al. |
| 2014/0288428 A1 | 9/2014 | Rothberg et al. |
| 2014/0316269 A1 | 10/2014 | Zhang et al. |
| 2014/0324034 A1 | 10/2014 | Assaf et al. |
| 2014/0330124 A1 | 11/2014 | Carol |
| 2014/0378832 A1 | 12/2014 | Sanghvi et al. |
| 2014/0378964 A1 | 12/2014 | Pearson |
| 2015/0011875 A1 | 1/2015 | Noordhoek et al. |
| 2015/0063668 A1 | 3/2015 | You et al. |
| 2015/0073261 A1 | 3/2015 | Kohler et al. |
| 2015/0080926 A1 | 3/2015 | Emery |
| 2015/0112235 A1 | 4/2015 | Brasset et al. |
| 2015/0148659 A1 | 5/2015 | Vahala |
| 2015/0151141 A1 | 6/2015 | Arnal et al. |
| 2015/0190121 A1 | 7/2015 | Slayton et al. |
| 2015/0190659 A1 | 7/2015 | Kolher |
| 2015/0196239 A1 | 7/2015 | Meehan et al. |
| 2015/0224347 A1 | 8/2015 | Barthe et al. |
| 2015/0257779 A1 | 9/2015 | Sinelnikov et al. |
| 2015/0258352 A1 | 9/2015 | Lin et al. |
| 2015/0265243 A1 | 9/2015 | Kelly |
| 2015/0273246 A1 | 10/2015 | Darlington et al. |
| 2015/0297177 A1 | 10/2015 | Boctor et al. |
| 2016/0004933 A1 | 1/2016 | Hu et al. |
| 2016/0038665 A1 | 2/2016 | Schaefer et al. |
| 2016/0114194 A1 | 4/2016 | Gertner |
| 2016/0120572 A1 | 5/2016 | Lee |
| 2016/0135782 A1 | 5/2016 | Chen et al. |
| 2016/0151618 A1 | 6/2016 | Powers et al. |
| 2016/0184614 A1 | 6/2016 | Matula et al. |
| 2016/0206341 A1 | 7/2016 | Slayton |
| 2016/0206867 A1 | 7/2016 | Hossack et al. |
| 2016/0249859 A1 | 9/2016 | Babkin et al. |
| 2016/0287909 A1 | 10/2016 | Maxwell et al. |
| 2016/0303166 A1 | 10/2016 | Katz et al. |
| 2016/0331583 A1 | 11/2016 | Geringer |
| 2016/0331585 A1 | 11/2016 | Kim |
| 2016/0339273 A1 | 11/2016 | Al Mayiah |
| 2016/0345938 A1 | 12/2016 | Tanter et al. |
| 2016/0354087 A1 | 12/2016 | Noonan et al. |
| 2016/0361574 A1 | 12/2016 | Barthe et al. |
| 2017/0000376 A1 | 1/2017 | Partanen et al. |
| 2017/0042521 A1 | 2/2017 | Popovic et al. |
| 2017/0049463 A1 | 2/2017 | Popovic et al. |
| 2017/0071515 A1 | 3/2017 | Chevillet et al. |
| 2017/0072227 A1 | 3/2017 | Khokhlova et al. |
| 2017/0072228 A1 | 3/2017 | Wang et al. |
| 2017/0079519 A1 | 3/2017 | Sung et al. |
| 2017/0100145 A1 | 4/2017 | Khoklova et al. |
| 2017/0120080 A1 | 5/2017 | Phillips et al. |
| 2017/0165046 A1 | 6/2017 | Johnson et al. |
| 2017/0183062 A1 | 6/2017 | Lee |
| 2017/0197099 A1 | 7/2017 | Ruebel et al. |
| 2017/0232277 A1 | 8/2017 | Hall et al. |
| 2017/0263846 A1 | 9/2017 | Nakamura et al. |
| 2017/0281983 A1 | 10/2017 | Marquet et al. |
| 2017/0326589 A1 | 11/2017 | Sudol |
| 2018/0000444 A1 | 1/2018 | Dayton et al. |
| 2018/0008787 A1 | 1/2018 | Schriver et al. |
| 2018/0028841 A1 | 2/2018 | Konofagou et al. |
| 2018/0064412 A1 | 3/2018 | Messas et al. |
| 2018/0161086 A1 | 6/2018 | Davalos et al. |
| 2018/0169444 A1 | 6/2018 | Averkiou et al. |
| 2018/0206816 A1 | 7/2018 | Prus et al. |
| 2018/0207029 A1 | 7/2018 | Herekar et al. |
| 2018/0236271 A1 | 8/2018 | Tanter et al. |
| 2018/0317884 A1 | 11/2018 | Chapelon et al. |
| 2018/0374471 A1 | 12/2018 | Dirksen et al. |
| 2019/0000422 A1 | 1/2019 | West et al. |
| 2019/0023804 A1 | 1/2019 | Onik et al. |
| 2019/0082998 A1 | 3/2019 | Nowroozi et al. |
| 2019/0105113 A1 | 4/2019 | Popovic et al. |
| 2019/0275353 A1 | 9/2019 | Cannata et al. |
| 2019/0282294 A1 | 9/2019 | Davalos et al. |
| 2019/0314045 A1 | 10/2019 | Cunitz et al. |
| 2019/0320904 A1 | 10/2019 | Mei |
| 2019/0323086 A1 | 10/2019 | Leuthardt et al. |
| 2019/0328500 A1 | 10/2019 | Cichon et al. |
| 2020/0010575 A1 | 1/2020 | Hode et al. |
| 2020/0037990 A1 | 2/2020 | Qiao et al. |
| 2020/0055085 A1 | 2/2020 | Taffler |
| 2020/0078608 A1 | 3/2020 | Maxwell et al. |
| 2020/0107843 A1 | 4/2020 | Goertz et al. |
| 2020/0182989 A1 | 6/2020 | Freeman et al. |
| 2020/0194117 A1 | 6/2020 | Krieger et al. |
| 2020/0253550 A1 | 8/2020 | Nair |
| 2020/0254285 A1 | 8/2020 | Jang et al. |
| 2020/0260964 A1 | 8/2020 | Collins et al. |
| 2020/0282239 A1 | 9/2020 | Beder et al. |
| 2020/0289080 A1 | 9/2020 | Yang et al. |
| 2020/0305842 A1 | 10/2020 | Rosenzweig et al. |
| 2020/0308785 A1 | 10/2020 | Sennhauser |
| 2020/0323515 A1 | 10/2020 | Levy |
| 2020/0330039 A1 | 10/2020 | Burkett et al. |
| 2020/0330075 A1 | 10/2020 | O'Reilly et al. |
| 2020/0346044 A1 | 11/2020 | Woodcare et al. |
| 2020/0353293 A1 | 11/2020 | Khokhlova et al. |
| 2020/0367835 A1 | 11/2020 | Anderson |
| 2020/0375576 A1 | 12/2020 | Moulton |
| 2020/0405258 A1 | 12/2020 | Dayton et al. |
| 2020/0405259 A1 | 12/2020 | Merritt |
| 2021/0000541 A1 | 1/2021 | Levy et al. |
| 2021/0009936 A1 | 1/2021 | Kamen et al. |
| 2021/0022703 A1 | 1/2021 | Nair |
| 2021/0022714 A1 | 1/2021 | Zagrodsky et al. |
| 2021/0100527 A1 | 4/2021 | Martin |
| 2021/0108866 A1 | 4/2021 | Lucht et al. |
| 2021/0121122 A1 | 4/2021 | Melcher et al. |
| 2021/0161398 A1 | 6/2021 | Millett et al. |
| 2021/0169515 A1 | 6/2021 | Pahk et al. |
| 2021/0170204 A1 | 6/2021 | Vortman et al. |
| 2021/0170205 A1 | 6/2021 | Vortman et al. |
| 2021/0187331 A1 | 6/2021 | Zadicario et al. |
| 2021/0196295 A1 | 7/2021 | Goudot et al. |
| 2021/0220607 A1 | 7/2021 | Sasamine et al. |
| 2021/0330294 A1 | 10/2021 | Hynynen et al. |
| 2021/0353161 A1 | 11/2021 | Merritt et al. |
| 2021/0386451 A1 | 12/2021 | Escudero et al. |
| 2021/0401366 A1 | 12/2021 | Weiss et al. |
| 2021/0401400 A1 | 12/2021 | Sheehan et al. |
| 2022/0008036 A1 | 1/2022 | Gulsen et al. |
| 2022/0022845 A1 | 1/2022 | Cort |
| 2022/0031287 A1 | 2/2022 | Ebbini et al. |
| 2022/0043143 A1 | 2/2022 | Prus et al. |
| 2022/0059227 A1 | 2/2022 | Park et al. |
| 2022/0079563 A1 | 3/2022 | Kemp |
| 2022/0087640 A1 | 3/2022 | Minas et al. |
| 2022/0110809 A1 | 4/2022 | Grindstaff et al. |
| 2022/0166462 A1 | 5/2022 | Deurenberg et al. |
| 2022/0167920 A1 | 6/2022 | Margolis |
| 2022/0168470 A1 | 6/2022 | Ricotti et al. |
| 2022/0196771 A1 | 6/2022 | Zur et al. |
| 2022/0202483 A1 | 6/2022 | Gertner |
| 2022/0203139 A1 | 6/2022 | Shapira |
| 2022/0219019 A1 | 7/2022 | Xu et al. |
| 2022/0233890 A1 | 7/2022 | Hynynen et al. |
| 2022/0240890 A1 | 8/2022 | Hancock et al. |
| 2022/0257329 A1 | 8/2022 | Stigall et al. |
| 2022/0280233 A1 | 9/2022 | Park et al. |
| 2022/0280367 A1 | 9/2022 | Diodato et al. |
| 2022/0296211 A1 | 9/2022 | Saroha et al. |
| 2022/0331611 A1 | 10/2022 | Razavi et al. |
| 2022/0338750 A1 | 10/2022 | Allen et al. |
| 2022/0346756 A1 | 11/2022 | Chen |
| 2022/0370025 A1 | 11/2022 | Regensburger et al. |
| 2022/0386970 A1 | 12/2022 | Merritt |
| 2022/0395333 A1 | 12/2022 | Merritt et al. |
| 2022/0409171 A1 | 12/2022 | Sudol et al. |
| 2022/0409858 A1 | 12/2022 | Lin |
| 2023/0000466 A1 | 1/2023 | Levy et al. |

(56) References Cited

U.S. PATENT DOCUMENTS

| 2023/0000469 | A1 | 1/2023 | Prus et al. |
|---|---|---|---|
| 2023/0008714 | A1 | 1/2023 | Rajguru et al. |
| 2023/0012365 | A1 | 1/2023 | Alpert et al. |
| 2023/0024998 | A1 | 1/2023 | Greenberg |
| 2023/0031859 | A1 | 2/2023 | Davies et al. |
| 2023/0037603 | A1 | 2/2023 | Pombo et al. |
| 2023/0038498 | A1 | 2/2023 | Xu et al. |
| 2023/0038543 | A1 | 2/2023 | Minas et al. |
| 2023/0042834 | A1 | 2/2023 | Henderson et al. |
| 2023/0045488 | A1 | 2/2023 | Rajguru et al. |
| 2023/0048979 | A1 | 2/2023 | Lindenmoyer et al. |
| 2023/0050732 | A1 | 2/2023 | Hancock et al. |
| 2023/0061534 | A1 | 3/2023 | Stopek |
| 2023/0073447 | A1 | 3/2023 | Minas et al. |
| 2023/0100912 | A1 | 3/2023 | Amar et al. |
| 2023/0112722 | A1 | 4/2023 | Hoffman et al. |
| 2023/0114972 | A1 | 4/2023 | Bigham et al. |
| 2023/0121688 | A1 | 4/2023 | Begin et al. |
| 2023/0126520 | A1 | 4/2023 | Lenich et al. |
| 2023/0145064 | A1 | 5/2023 | Vortman et al. |
| 2023/0181140 | A1 | 6/2023 | Cohen et al. |
| 2023/0181156 | A1 | 6/2023 | Cohen et al. |
| 2023/0190119 | A1 | 6/2023 | Groenland et al. |
| 2023/0190215 | A1 | 6/2023 | Nachtomy et al. |
| 2023/0190224 | A1 | 6/2023 | Rajguru et al. |
| 2023/0190225 | A1 | 6/2023 | Cohen et al. |
| 2023/0190226 | A1 | 6/2023 | Rajguru et al. |
| 2023/0190227 | A1 | 6/2023 | Cohen et al. |
| 2023/0190228 | A1 | 6/2023 | Cohen et al. |
| 2023/0190229 | A1 | 6/2023 | Cohen et al. |
| 2023/0190230 | A1 | 6/2023 | Yang et al. |
| 2023/0191162 | A1 | 6/2023 | Yau et al. |
| 2023/0196569 | A1 | 6/2023 | Cohen et al. |
| 2023/0200899 | A1 | 6/2023 | Nair |
| 2023/0201553 | A1 | 6/2023 | Levy et al. |
| 2023/0218230 | A1 | 7/2023 | Wu et al. |
| 2023/0218262 | A1 | 7/2023 | Boutelle et al. |
| 2023/0218266 | A1 | 7/2023 | Stigall et al. |
| 2023/0218269 | A1 | 7/2023 | Alpert et al. |
| 2023/0218930 | A1 | 7/2023 | Stopek et al. |
| 2023/0240615 | A1 | 8/2023 | May et al. |
| 2023/0240647 | A1 | 8/2023 | Minas et al. |
| 2023/0240663 | A1 | 8/2023 | Lafond et al. |
| 2023/0240792 | A1 | 8/2023 | Rakic et al. |
| 2023/0255597 | A1 | 8/2023 | O'Reilly et al. |
| 2023/0260601 | A1 | 8/2023 | Abel et al. |
| 2023/0263507 | A1 | 8/2023 | Groenland et al. |
| 2023/0270388 | A1 | 8/2023 | Richardson et al. |
| 2023/0293148 | A1 | 9/2023 | Stigall et al. |
| 2023/0293149 | A1 | 9/2023 | Stigall et al. |
| 2023/0309859 | A1 | 10/2023 | Sreedhar et al. |
| 2023/0310899 | A1 | 10/2023 | Hall et al. |
| 2023/0310900 | A1 | 10/2023 | Cannata et al. |
| 2023/0310901 | A1 | 10/2023 | Cannata et al. |
| 2023/0320600 | A1 | 10/2023 | Tochterman et al. |
| 2023/0321327 | A1 | 10/2023 | Maxwell et al. |
| 2023/0321398 | A1 | 10/2023 | May |
| 2023/0329559 | A1 | 10/2023 | Xu et al. |
| 2023/0333617 | A1 | 10/2023 | Spencer et al. |
| 2023/0334659 | A1 | 10/2023 | Marama et al. |
| 2023/0334677 | A1 | 10/2023 | Sturm |
| 2023/0338010 | A1 | 10/2023 | Sturm |
| 2023/0372025 | A1 | 11/2023 | Van der Zaag et al. |
| 2023/0381544 | A1 | 11/2023 | Penot et al. |
| 2023/0389891 | A1 | 12/2023 | Cohen et al. |
| 2023/0398381 | A1 | 12/2023 | Vitek et al. |
| 2024/0000422 | A1 | 1/2024 | Cort |
| 2024/0000426 | A1 | 1/2024 | Davies et al. |
| 2024/0001157 | A1 | 1/2024 | Cannata et al. |
| 2024/0001158 | A1 | 1/2024 | Cannata et al. |
| 2024/0023928 | A1 | 1/2024 | Di Tullio et al. |
| 2024/0023930 | A1 | 1/2024 | Anderson |
| 2024/0023941 | A1 | 1/2024 | Rhodes |
| 2024/0024705 | A1 | 1/2024 | Xu et al. |
| 2024/0033542 | A1 | 2/2024 | Cain et al. |
| 2024/0065632 | A1 | 2/2024 | Burkett |
| 2024/0081754 | A1 | 3/2024 | Regensburger et al. |
| 2024/0138807 | A1 | 5/2024 | Minas |
| 2024/0165666 | A1 | 5/2024 | Hynynen et al. |
| 2024/0188929 | A1 | 6/2024 | Minas et al. |
| 2024/0188931 | A1 | 6/2024 | Ossmann et al. |
| 2024/0189627 | A1 | 6/2024 | Bogott et al. |
| 2024/0225592 | A1 | 7/2024 | May et al. |
| 2024/0245374 | A1 | 7/2024 | Jenkins et al. |
| 2024/0245390 | A1 | 7/2024 | Winkler Brown et al. |
| 2024/0245465 | A1 | 7/2024 | Jenkins et al. |
| 2024/0285249 | A1 | 8/2024 | May |
| 2024/0299092 | A1 | 9/2024 | Boinagrov et al. |
| 2024/0307027 | A1 | 9/2024 | Minas |
| 2024/0335680 | A1 | 10/2024 | Achrol et al. |
| 2024/0341732 | A1 | 10/2024 | Hoffman et al. |
| 2024/0350118 | A1 | 10/2024 | Jenkins et al. |
| 2024/0374242 | A1 | 11/2024 | Merritt et al. |
| 2024/0408416 | A1 | 12/2024 | Cannata et al. |
| 2025/0018227 | A1 | 1/2025 | Son et al. |
| 2025/0040912 | A1 | 2/2025 | Levy et al. |
| 2025/0041577 | A1 | 2/2025 | Shapira et al. |
| 2025/0072872 | A1 | 3/2025 | Nachtomy et al. |
| 2025/0160786 | A1 | 5/2025 | Zagrodsky et al. |
| 2025/0186808 | A1 | 6/2025 | Cannata et al. |
| 2025/0249289 | A1 | 8/2025 | Miller et al. |
| 2025/0256132 | A1 | 8/2025 | Xu et al. |
| 2025/0263798 | A1 | 8/2025 | Achrol et al. |
| 2025/0320390 | A1 | 10/2025 | Shachaf et al. |
| 2025/0344999 | A1 | 11/2025 | Wu et al. |
| 2025/0349023 | A1 | 11/2025 | Rajguru et al. |
| 2025/0352828 | A1 | 11/2025 | Miller et al. |
| 2025/0352831 | A1 | 11/2025 | Cannata et al. |
| 2025/0360344 | A1 | 11/2025 | Hall et al. |
| 2025/0367478 | A1 | 12/2025 | Xu et al. |

FOREIGN PATENT DOCUMENTS

| AU | 2021406651 | B2 | 4/2025 |
|---|---|---|---|
| AU | 2022215411 | B2 | 5/2025 |
| BR | 112018017326 | B1 | 12/2022 |
| BR | 102023017634 | A2 | 1/2025 |
| CA | 3073552 | A1 | 3/2019 |
| CA | 3101381 | A1 | 11/2019 |
| CA | 3055856 | A1 | 4/2020 |
| CA | 3130859 | A1 | 10/2020 |
| CA | 3153080 | A1 | 4/2021 |
| CA | 2910561 | C | 7/2021 |
| CA | 2908740 | C | 10/2021 |
| CA | 2980976 | C | 3/2023 |
| CA | 2840014 | C | 8/2023 |
| CN | 1669672 | A | 9/2005 |
| CN | 1732031 | A | 2/2006 |
| CN | 201197744 | Y | 2/2009 |
| CN | 102292123 | A | 12/2011 |
| CN | 102481164 | A | 5/2012 |
| CN | 102665585 | A | 9/2012 |
| CN | 103537016 | A | 1/2014 |
| CN | 103648361 | A | 3/2014 |
| CN | 103812477 | A | 5/2014 |
| CN | 104013444 | A | 9/2014 |
| CN | 104135938 | A | 11/2014 |
| CN | 104208822 | A | 12/2014 |
| CN | 106999076 | B | 8/2017 |
| CN | 109185113 | A | 1/2019 |
| CN | 109219415 | A | 1/2019 |
| CN | 109689160 | A | 4/2019 |
| CN | 208725992 | U | 4/2019 |
| CN | 111565642 | A | 8/2020 |
| CN | 111655337 | A | 9/2020 |
| CN | 111699022 | A | 9/2020 |
| CN | 111712300 | A | 9/2020 |
| CN | 111712301 | A | 9/2020 |
| CN | 106999053 | B | 10/2020 |
| CN | 107660137 | B | 10/2020 |
| CN | 111757769 | A | 10/2020 |
| CN | 112204412 | A | 1/2021 |
| CN | 112236195 | A | 1/2021 |
| CN | 106661535 | B | 3/2021 |

(56) References Cited

FOREIGN PATENT DOCUMENTS

| | | | |
|---|---|---|---|
| CN | 112533673 | A | 3/2021 |
| CN | 112566694 | A | 3/2021 |
| CN | 106999054 | B | 5/2021 |
| CN | 106793997 | B | 6/2021 |
| CN | 107530049 | B | 6/2021 |
| CN | 112912011 | A | 6/2021 |
| CN | 112912012 | A | 6/2021 |
| CN | 112912013 | A | 6/2021 |
| CN | 112969413 | A | 6/2021 |
| CN | 112996445 | A | 6/2021 |
| CN | 113167877 | A | 7/2021 |
| CN | 113196080 | A | 7/2021 |
| CN | 109196369 | B | 8/2021 |
| CN | 109200484 | B | 8/2021 |
| CN | 113316419 | A | 8/2021 |
| CN | 113329788 | A | 8/2021 |
| CN | 109640830 | B | 10/2021 |
| CN | 113473917 | A | 10/2021 |
| CN | 113507946 | A | 10/2021 |
| CN | 113518588 | A | 10/2021 |
| CN | 113705586 | A | 11/2021 |
| CN | 110662575 | B | 12/2021 |
| CN | 113905666 | A | 1/2022 |
| CN | 114222536 | A | 3/2022 |
| CN | 114366154 | A | 4/2022 |
| CN | 114423362 | A | 4/2022 |
| CN | 110248606 | B | 6/2022 |
| CN | 115227992 | A | 10/2022 |
| CN | 109843181 | B | 11/2022 |
| CN | 115461000 | A | 12/2022 |
| CN | 115515504 | A | 12/2022 |
| CN | 109091768 | B | 3/2023 |
| CN | 115779285 | A | 3/2023 |
| CN | 115779287 | A | 3/2023 |
| CN | 115813438 | A | 3/2023 |
| CN | 111032157 | B | 4/2023 |
| CN | 115916035 | A | 4/2023 |
| CN | 110958858 | B | 5/2023 |
| CN | 116172611 | A | 5/2023 |
| CN | 111655337 | B | 6/2023 |
| CN | 109416908 | B | 7/2023 |
| CN | 116507295 | A | 7/2023 |
| CN | 107529989 | B | 8/2023 |
| CN | 111372522 | B | 8/2023 |
| CN | 116617589 | A | 8/2023 |
| CN | 112236195 | B | 9/2023 |
| CN | 113615098 | B | 9/2023 |
| CN | 114555247 | B | 9/2023 |
| CN | 116744856 | A | 9/2023 |
| CN | 116761554 | A | 9/2023 |
| CN | 109416907 | B | 10/2023 |
| CN | 117321444 | A | 12/2023 |
| CN | 117500437 | A | 2/2024 |
| CN | 117580499 | A | 2/2024 |
| CN | 111212606 | B | 3/2024 |
| CN | 113490459 | B | 5/2024 |
| CN | 118042992 | A | 5/2024 |
| CN | 118414127 | A | 7/2024 |
| CN | 112601498 | B | 9/2024 |
| CN | 118678921 | A | 9/2024 |
| CN | 113271866 | B | 10/2024 |
| CN | 112603273 | B | 12/2024 |
| CN | 112639754 | B | 12/2024 |
| CN | 119367006 | A | 1/2025 |
| CN | 112704620 | B | 2/2025 |
| CN | 114287963 | B | 2/2025 |
| CN | 110410498 | B | 3/2025 |
| CN | 112426634 | B | 3/2025 |
| CN | 112545816 | B | 5/2025 |
| CN | 112546464 | B | 6/2025 |
| CN | 112618971 | B | 6/2025 |
| CN | 113040905 | B | 6/2025 |
| CN | 114340682 | B | 7/2025 |
| CN | 115515567 | B | 7/2025 |
| CN | 112546465 | B | 8/2025 |
| CN | 309464789 | S | 8/2025 |
| CN | 111991712 | B | 9/2025 |
| CN | 112494106 | B | 10/2025 |
| CN | 114638798 | B | 10/2025 |
| DE | 3220751 | A1 | 12/1983 |
| DE | 3544628 | A1 | 6/1987 |
| DE | 3817094 | A1 | 11/1989 |
| DE | 4012760 | A1 | 5/1992 |
| DE | 602020055151 | T2 | 7/2025 |
| DE | 602022018890 | T2 | 8/2025 |
| DE | 602020058523 | T2 | 9/2025 |
| DE | 602020059056 | T2 | 9/2025 |
| DE | 602022021590 | T2 | 9/2025 |
| DE | 112023005080 | T5 | 10/2025 |
| DE | 602017092008 | T2 | 10/2025 |
| DE | 602022022517 | T2 | 10/2025 |
| EP | 0017382 | A1 | 10/1980 |
| EP | 0320303 | A2 | 6/1989 |
| EP | 0332871 | A2 | 9/1989 |
| EP | 0384831 | A2 | 8/1990 |
| EP | 0619156 | A1 | 10/1994 |
| EP | 0755653 | A1 | 1/1997 |
| EP | 1374785 | A1 | 1/2004 |
| EP | 1504713 | A1 | 2/2005 |
| EP | 1566201 | A2 | 8/2005 |
| EP | 2397188 | A1 | 12/2011 |
| EP | 2934308 | B1 | 10/2015 |
| EP | 2934309 | B1 | 10/2015 |
| EP | 3097180 | B1 | 11/2016 |
| EP | 3100767 | B1 | 11/2019 |
| EP | 2759003 | B1 | 8/2020 |
| EP | 3558457 | A4 | 8/2020 |
| EP | 3700629 | A1 | 9/2020 |
| EP | 3218829 | B1 | 10/2020 |
| EP | 3229688 | B1 | 10/2020 |
| EP | 3723857 | A1 | 10/2020 |
| EP | 2887989 | B1 | 2/2021 |
| EP | 3777689 | A1 | 2/2021 |
| EP | 2938253 | B1 | 3/2021 |
| EP | 3076864 | B1 | 3/2021 |
| EP | 2802276 | B1 | 4/2021 |
| EP | 2809221 | B1 | 4/2021 |
| EP | 3801761 | A1 | 4/2021 |
| EP | 3801762 | A2 | 4/2021 |
| EP | 3801763 | A1 | 4/2021 |
| EP | 2967369 | B1 | 5/2021 |
| EP | 2967488 | B1 | 6/2021 |
| EP | 3184048 | B1 | 6/2021 |
| EP | 2967370 | B1 | 9/2021 |
| EP | 3482390 | B1 | 9/2021 |
| EP | 3870067 | A1 | 9/2021 |
| EP | 3870069 | A1 | 9/2021 |
| EP | 3876843 | A1 | 9/2021 |
| EP | 2931130 | B1 | 10/2021 |
| EP | 2934304 | B1 | 10/2021 |
| EP | 3887843 | A1 | 10/2021 |
| EP | 3888534 | A1 | 10/2021 |
| EP | 3895604 | A1 | 10/2021 |
| EP | 3897391 | A1 | 10/2021 |
| EP | 3229672 | B1 | 11/2021 |
| EP | 3902603 | A1 | 11/2021 |
| EP | 3903672 | A1 | 11/2021 |
| EP | 2964096 | B1 | 12/2021 |
| EP | 3930776 | A1 | 1/2022 |
| EP | 3545829 | B1 | 3/2022 |
| EP | 3959530 | A2 | 3/2022 |
| EP | 3060129 | B1 | 4/2022 |
| EP | 3986296 | A1 | 4/2022 |
| EP | 3988167 | A1 | 4/2022 |
| EP | 2914166 | B1 | 5/2022 |
| EP | 3229674 | B1 | 5/2022 |
| EP | 2779907 | B1 | 6/2022 |
| EP | 3102098 | B1 | 6/2022 |
| EP | 2965263 | B1 | 7/2022 |
| EP | 2726152 | B1 | 8/2022 |
| EP | 4041387 | A1 | 8/2022 |
| EP | 4042936 | A1 | 8/2022 |
| EP | 3298959 | B2 | 9/2022 |
| EP | 2931131 | B1 | 11/2022 |

(56)          References Cited

FOREIGN PATENT DOCUMENTS

| | | | |
|---|---|---|---|
| EP | 2938268 | B1 | 11/2022 |
| EP | 3581103 | B1 | 11/2022 |
| EP | 4087492 | A1 | 11/2022 |
| EP | 4093470 | A1 | 11/2022 |
| EP | 3091905 | B1 | 12/2022 |
| EP | 4098203 | A1 | 12/2022 |
| EP | 2950737 | B1 | 1/2023 |
| EP | 3057496 | B1 | 1/2023 |
| EP | 4114274 | A1 | 1/2023 |
| EP | 4117534 | A1 | 1/2023 |
| EP | 2869804 | B1 | 2/2023 |
| EP | 2938265 | B1 | 2/2023 |
| EP | 3024403 | B1 | 3/2023 |
| EP | 4138672 | A1 | 3/2023 |
| EP | 4151156 | A1 | 3/2023 |
| EP | 2938271 | B1 | 4/2023 |
| EP | 4161360 | A1 | 4/2023 |
| EP | 4179995 | A2 | 5/2023 |
| EP | 3171764 | B1 | 6/2023 |
| EP | 4201342 | A1 | 6/2023 |
| EP | 2931132 | B1 | 7/2023 |
| EP | 3229695 | B1 | 7/2023 |
| EP | 4209178 | A1 | 7/2023 |
| EP | 4209179 | A1 | 7/2023 |
| EP | 4226864 | A1 | 8/2023 |
| EP | 4230121 | A2 | 8/2023 |
| EP | 4230146 | A1 | 8/2023 |
| EP | 4233972 | A2 | 8/2023 |
| EP | 2866733 | B1 | 9/2023 |
| EP | 3870069 | B1 | 9/2023 |
| EP | 4247489 | A1 | 9/2023 |
| EP | 3484371 | B1 | 10/2023 |
| EP | 3658037 | B1 | 10/2023 |
| EP | 3685874 | B1 | 10/2023 |
| EP | 3870070 | B1 | 10/2023 |
| EP | 4257151 | A1 | 10/2023 |
| EP | 2938255 | B1 | 11/2023 |
| EP | 3229906 | B1 | 11/2023 |
| EP | 3764914 | B1 | 11/2023 |
| EP | 3903672 | B1 | 11/2023 |
| EP | 4272654 | A2 | 11/2023 |
| EP | 4275609 | A2 | 11/2023 |
| EP | 3316804 | B1 | 12/2023 |
| EP | 3519109 | B1 | 12/2023 |
| EP | 3166479 | B1 | 1/2024 |
| EP | 3537984 | B1 | 1/2024 |
| EP | 3908195 | B1 | 2/2024 |
| EP | 3182920 | B1 | 3/2024 |
| EP | 3174643 | B1 | 4/2024 |
| EP | 3814917 | B1 | 4/2024 |
| EP | 4349283 | A1 | 4/2024 |
| EP | 3681419 | B1 | 5/2024 |
| EP | 4368118 | A2 | 5/2024 |
| EP | 2804525 | B1 | 6/2024 |
| EP | 4380667 | A2 | 6/2024 |
| EP | 4385428 | A1 | 6/2024 |
| EP | 4459545 | A1 | 6/2024 |
| EP | 3324836 | B1 | 9/2024 |
| EP | 3624732 | B1 | 11/2024 |
| EP | 4289415 | A4 | 1/2025 |
| EP | 4406484 | B1 | 1/2025 |
| EP | 3190958 | B1 | 2/2025 |
| EP | 4282471 | B1 | 3/2025 |
| EP | 3277378 | B1 | 5/2025 |
| EP | 4041463 | B1 | 8/2025 |
| EP | 3986296 | B1 | 9/2025 |
| EP | 4275744 | B1 | 10/2025 |
| EP | 4633490 | A1 | 10/2025 |
| ES | 2774069 | T3 | 7/2020 |
| ES | 2819552 | T3 | 4/2021 |
| ES | 2829822 | T3 | 6/2021 |
| ES | 2998435 | T3 | 2/2025 |
| ES | 3005837 | T3 | 3/2025 |
| GB | 2099582 | A | 12/1982 |
| HK | 1245715 | B | 1/2021 |
| IL | 254768 | A | 5/2021 |
| IL | 261285 | B | 2/2022 |
| IN | 202117039853 | A | 12/2021 |
| IN | 387413 | B | 1/2022 |
| IN | 445766 | B | 8/2023 |
| JP | 60-80779 | A | 5/1985 |
| JP | 61-196718 | A | 8/1986 |
| JP | S62144641 | A | 6/1987 |
| JP | H02104343 | A | 4/1990 |
| JP | 02-215451 | A | 8/1990 |
| JP | H0422351 | A | 1/1992 |
| JP | 06-197907 | A | 7/1994 |
| JP | 07-504339 | A | 5/1995 |
| JP | H07213527 | A | 8/1995 |
| JP | H07284499 | A | 10/1995 |
| JP | 08-84740 | A | 4/1996 |
| JP | 06-304178 | A | 5/1996 |
| JP | 08-131454 | A | 5/1996 |
| JP | 09-55571 | A | 2/1997 |
| JP | H10305041 | A | 11/1998 |
| JP | 10-512477 | A | 12/1998 |
| JP | 2000300559 | A | 10/2000 |
| JP | 2003510159 | A | 3/2003 |
| JP | 2004505660 | A | 2/2004 |
| JP | 2004249106 | A | 9/2004 |
| JP | 2005167058 | A | 6/2005 |
| JP | 2006511265 | A | 4/2006 |
| JP | 2007144225 | A | 6/2007 |
| JP | 2007520307 | A | 7/2007 |
| JP | 2008049199 | A | 3/2008 |
| JP | 2010019554 | A | 1/2010 |
| JP | 2010029650 | A | 2/2010 |
| JP | 2010204068 | A | 9/2010 |
| JP | 2013538097 | A | 10/2013 |
| JP | 2004512502 | A | 4/2014 |
| JP | 2014204876 | A | 10/2014 |
| JP | 2015002983 | A | 1/2015 |
| JP | 2015519970 | A | 7/2015 |
| JP | 2016508808 | A | 3/2016 |
| JP | 2017/506542 | A | 3/2017 |
| JP | 2017506538 | A | 3/2017 |
| JP | 2019051295 | A | 4/2019 |
| JP | 2020525167 | A | 8/2020 |
| JP | 2020525168 | A | 8/2020 |
| JP | 2020525169 | A | 8/2020 |
| JP | 6785554 | B2 | 10/2020 |
| JP | 6789944 | B2 | 11/2020 |
| JP | 2020534077 | A | 11/2020 |
| JP | 2020195788 | A | 12/2020 |
| JP | 2020535895 | A | 12/2020 |
| JP | 6832958 | B2 | 2/2021 |
| JP | 6835719 | B2 | 2/2021 |
| JP | 6838057 | B2 | 3/2021 |
| JP | 6849592 | B2 | 3/2021 |
| JP | 2021510104 | A | 4/2021 |
| JP | 6896719 | B2 | 6/2021 |
| JP | 6934933 | B2 | 9/2021 |
| JP | 6951560 | B2 | 10/2021 |
| JP | 6979633 | B2 | 12/2021 |
| JP | 6980696 | B2 | 12/2021 |
| JP | 7012726 | B2 | 1/2022 |
| JP | 2022500092 | A | 1/2022 |
| JP | 2022500093 | A | 1/2022 |
| JP | 2022501080 | A | 1/2022 |
| JP | 2022504159 | A | 1/2022 |
| JP | 2022509389 | A | 1/2022 |
| JP | 2022509391 | A | 1/2022 |
| JP | 2022509392 | A | 1/2022 |
| JP | 2022509393 | A | 1/2022 |
| JP | 2022509395 | A | 1/2022 |
| JP | 2022509401 | A | 1/2022 |
| JP | 2022509453 | A | 1/2022 |
| JP | 2022510217 | A | 1/2022 |
| JP | 7019679 | B2 | 2/2022 |
| JP | 7026118 | B2 | 2/2022 |
| JP | 2022514272 | A | 2/2022 |
| JP | 2022515488 | A | 2/2022 |
| JP | 2022516078 | A | 2/2022 |
| JP | 7053500 | B2 | 4/2022 |

(56) References Cited

FOREIGN PATENT DOCUMENTS

| | | | |
|----|------------------|----|---------|
| JP | 2022526104 | A  | 5/2022  |
| JP | 2022527043 | A  | 5/2022  |
| JP | 2022095785 | A  | 6/2022  |
| JP | 7171645    | B2 | 11/2022 |
| JP | 7171663    | B2 | 11/2022 |
| JP | 7175640    | B2 | 11/2022 |
| JP | 2022546288 | A  | 11/2022 |
| JP | 7187715    | B2 | 12/2022 |
| JP | 2022551875 | A  | 12/2022 |
| JP | 2022552229 | A  | 12/2022 |
| JP | 7201819    | B2 | 1/2023  |
| JP | 7232204    | B2 | 3/2023  |
| JP | 7239466    | B2 | 3/2023  |
| JP | 7265525    | B2 | 4/2023  |
| JP | 2023071859 | A  | 5/2023  |
| JP | 7292448    | B2 | 6/2023  |
| JP | 7299992    | B2 | 6/2023  |
| JP | 2023085350 | A  | 6/2023  |
| JP | 7302936    | B2 | 7/2023  |
| JP | 7304344    | B2 | 7/2023  |
| JP | 7321162    | B2 | 8/2023  |
| JP | 7325430    | B2 | 8/2023  |
| JP | 7335367    | B2 | 8/2023  |
| JP | 2023116673 | A  | 8/2023  |
| JP | 7340594    | B2 | 9/2023  |
| JP | 7346293    | B2 | 9/2023  |
| JP | 7351972    | B2 | 9/2023  |
| JP | 7352561    | B2 | 9/2023  |
| JP | 2023123676 | A  | 9/2023  |
| JP | 2023134811 | A  | 9/2023  |
| JP | 7358391    | B2 | 10/2023 |
| JP | 7359765    | B2 | 10/2023 |
| JP | 7370386    | B2 | 10/2023 |
| JP | 2023162327 | A  | 11/2023 |
| JP | 7391100    | B2 | 12/2023 |
| JP | 2024010135 | A  | 1/2024  |
| JP | 2024020483 | A  | 2/2024  |
| JP | 7479288    | B2 | 5/2024  |
| JP | 7479351    | B2 | 5/2024  |
| JP | 7485383    | B2 | 5/2024  |
| JP | 7530561    | B2 | 8/2024  |
| JP | 7542708    | B2 | 8/2024  |
| JP | 2024161427 | A  | 11/2024 |
| JP | 7612816    | B2 | 1/2025  |
| JP | 2025013082 | A  | 1/2025  |
| JP | 7641600    | B2 | 3/2025  |
| JP | 7643694    | B2 | 3/2025  |
| JP | 2025031814 | A  | 3/2025  |
| KR | 102574559  | B1 | 9/2023  |
| KR | 102764982  | B1 | 2/2025  |
| KR | 20250019597 | A  | 2/2025  |
| KR | DM226835001 | S1 | 4/2025  |
| KR | 102854907  | B1 | 9/2025  |
| RU | 2589649    | C1 | 7/2016  |
| RU | 2839094    | C2 | 4/2025  |
| TW | 201729929  | A  | 9/2017  |
| WO | WO94/06355 | A1 | 3/1994  |
| WO | WO02/32506 | A1 | 4/2002  |
| WO | WO2005/018469 | A1 | 3/2005 |
| WO | WO2008/051484 | A2 | 5/2008 |
| WO | WO2011/040054 | A1 | 7/2011 |
| WO | WO2011/092683 | A1 | 8/2011 |
| WO | WO2011/154654 | A2 | 12/2011 |
| WO | WO2014/008594 | A1 | 1/2014 |
| WO | WO2014/071386 | A1 | 5/2014 |
| WO | WO2015/000953 | A1 | 1/2015 |
| WO | WO2015/031532 | A1 | 3/2015 |
| WO | WO2015/153909 | A2 | 10/2015 |
| WO | WO2016/099279 | A1 | 6/2016 |
| WO | WO2018/149671 | A1 | 8/2018 |
| WO | WO2018/208189 | A1 | 11/2018 |
| WO | WO2019/081329 | A1 | 5/2019 |
| WO | WO2019/117926 | A1 | 6/2019 |
| WO | WO2019/122941 | A1 | 6/2019 |
| WO | WO2019/148154 | A1 | 8/2019 |
| WO | WO2020/074615 | A1 | 4/2020 |
| WO | WO2020/087049 | A1 | 4/2020 |
| WO | WO2020/112688 | A1 | 6/2020 |
| WO | WO2020/217098 | A2 | 10/2020 |
| WO | WO2020/237382 | A1 | 12/2020 |
| WO | WO2020/245660 | A1 | 12/2020 |
| WO | WO2021/014221 | A1 | 1/2021 |
| WO | WO2021/032887 | A1 | 2/2021 |
| WO | WO2021/069216 | A1 | 4/2021 |
| WO | WO2021/069971 | A1 | 4/2021 |
| WO | WO2021/089810 | A1 | 5/2021 |
| WO | WO2021/105358 | A1 | 6/2021 |
| WO | WO2021/115958 | A1 | 6/2021 |
| WO | WO2021/116763 | A1 | 6/2021 |
| WO | WO2021/122253 | A1 | 6/2021 |
| WO | WO2021/123905 | A2 | 6/2021 |
| WO | WO2021/123906 | A1 | 6/2021 |
| WO | WO2021/140042 | A1 | 7/2021 |
| WO | WO2021/142090 | A1 | 7/2021 |
| WO | WO2021/170510 | A1 | 9/2021 |
| WO | WO2021/175626 | A1 | 9/2021 |
| WO | WO2021/176275 | A1 | 9/2021 |
| WO | WO2021/178961 | A1 | 9/2021 |
| WO | WO2021/180501 | A1 | 9/2021 |
| WO | WO2021/180550 | A1 | 9/2021 |
| WO | WO2021/213927 | A1 | 10/2021 |
| WO | WO2021/249936 | A1 | 12/2021 |
| WO | WO2021/258007 | A1 | 12/2021 |
| WO | WO2022/013266 | A1 | 1/2022 |
| WO | WO2022/040493 | A1 | 2/2022 |
| WO | WO2022/047193 | A8 | 3/2022 |
| WO | WO2022/056394 | A1 | 3/2022 |
| WO | WO2022/069254 | A1 | 4/2022 |
| WO | WO2022/069303 | A2 | 4/2022 |
| WO | WO2022/069327 | A2 | 4/2022 |
| WO | WO2022/078744 | A1 | 4/2022 |
| WO | WO2022/097138 | A1 | 5/2022 |
| WO | WO2022/104683 | A1 | 5/2022 |
| WO | WO2022/106891 | A1 | 5/2022 |
| WO | WO2022/152724 | A1 | 7/2022 |
| WO | WO2022/152827 | A1 | 7/2022 |
| WO | WO2022/152828 | A1 | 7/2022 |
| WO | WO2022/228922 | A1 | 11/2022 |
| WO | WO2022/238058 | A1 | 11/2022 |
| WO | WO2022/238092 | A1 | 11/2022 |
| WO | WO2022/238229 | A1 | 11/2022 |
| WO | WO2022/238274 | A1 | 11/2022 |
| WO | WO2022/238276 | A1 | 11/2022 |
| WO | WO2022/238392 | A1 | 11/2022 |
| WO | WO2022/247242 | A1 | 12/2022 |
| WO | WO2022/258561 | A1 | 12/2022 |
| WO | WO2022/260746 | A1 | 12/2022 |
| WO | WO2022/260747 | A1 | 12/2022 |
| WO | WO2023/274899 | A1 | 1/2023 |
| WO | WO2023/275617 | A2 | 1/2023 |
| WO | WO2023/275771 | A1 | 1/2023 |
| WO | WO2023/012516 | A2 | 2/2023 |
| WO | WO2023/036742 | A1 | 3/2023 |
| WO | WO2023/052278 | A1 | 4/2023 |
| WO | WO2023/084307 | A1 | 5/2023 |
| WO | WO2023/104599 | A1 | 6/2023 |
| WO | WO2023/104841 | A1 | 6/2023 |
| WO | WO2023/110555 | A1 | 6/2023 |
| WO | WO2023/110556 | A1 | 6/2023 |
| WO | WO2023/110594 | A1 | 6/2023 |
| WO | WO2023/110607 | A1 | 6/2023 |
| WO | WO2023/117721 | A1 | 6/2023 |
| WO | WO2023/117821 | A1 | 6/2023 |
| WO | WO2023/117822 | A1 | 6/2023 |
| WO | WO2023/118080 | A1 | 6/2023 |
| WO | WO2023105288 | A1 | 6/2023 |
| WO | WO2023105290 | A1 | 6/2023 |
| WO | WO2023/131566 | A1 | 7/2023 |
| WO | WO2023/131574 | A1 | 7/2023 |
| WO | WO2023/135024 | A1 | 7/2023 |
| WO | WO2023/141653 | A2 | 7/2023 |
| WO | WO2023/152639 | A1 | 8/2023 |
| WO | WO2023/169967 | A1 | 9/2023 |
| WO | WO2023/180811 | A2 | 9/2023 |

(56)                    References Cited

FOREIGN PATENT DOCUMENTS

| | | | |
|---|---|---|---|
| WO | WO2023/218428 A1 | 11/2023 |
| WO | WO2023/230053 A1 | 11/2023 |
| WO | WO2023/230054 A1 | 11/2023 |
| WO | WO2024/009143 A1 | 1/2024 |
| WO | WO2024/016088 A1 | 1/2024 |
| WO | WO2024/040185 A2 | 2/2024 |
| WO | WO2024/047580 A1 | 3/2024 |
| WO | WO2024/092272 A1 | 5/2024 |
| WO | WO2024/120659 A1 | 6/2024 |
| WO | WO2024/125872 A1 | 6/2024 |
| WO | WO2024/130252 A1 | 6/2024 |
| WO | WO2024/144897 A1 | 7/2024 |
| WO | WO2024/148416 A1 | 7/2024 |
| WO | WO2024/157226 A1 | 8/2024 |
| WO | WO2024/163876 A1 | 8/2024 |
| WO | WO2024/201441 A1 | 10/2024 |
| WO | WO2024/208895 A1 | 10/2024 |
| WO | WO2024/209347 A1 | 10/2024 |
| WO | WO2024/209348 A1 | 10/2024 |
| WO | WO2024/211441 A1 | 10/2024 |
| WO | WO2024/211443 A1 | 10/2024 |
| WO | WO2024/216282 A2 | 10/2024 |
| WO | WO2024/221001 A2 | 10/2024 |
| WO | WO2025/038127 A1 | 2/2025 |
| WO | WO2025/059671 A1 | 3/2025 |

OTHER PUBLICATIONS

Hoogenboom et al.; Mechanical high-intensity focused ultrasound destruction of soft tissue: working mechanisms and physiologic effects; Ultrasound in medicine & biology; 41(6); pp. 1500-1517; Jun. 1, 2015.

Ma et al.; Acoustic focusing and imaging via phononic crystal and acoustic metamaterials; Journal of Applied Physics; 131(1); doi: 10.10653/5.0074503; 29 pages; Jan. 5, 2022.

Sukovich et al.; Real-time transcranial histotripsy treatment localization and mapping using acoustic cavitation emission feedback; IEEE transactions on ultrasonics, ferroelectrics, and frequency control; 67(6); pp. 1178-1791; Jan. 17, 2020.

Stopek.; U.S. Appl. No. 18/761,937 entitled "Minimally invasive histotripsy systems and methods," filed Jul. 2, 2024.

Shaffer et al.; U.S. Appl. No. 18/832,708 entitled "Histotripsy systems and methods," filed Jul. 24, 2024.

Cain et al.; Concentric-ring and sector-vortex phased-array applicators for ultrasound hyperthermia; IEEE Transactions on Microwave Theory and Techniques; 34(5); pp. 542-551; May 1986.

Hynynen et al.; Feasibility of using ultrasound phased arrays for MRI monitored noninvasive surgery; IEEE transactions on ultrasonics, ferroelectrics, and frequency control; 43(6); pp. 1043-1053; Nov. 1996.

Xu et al.; U.S. Appl. No. 18/568,038 entitled "Minimally invasive histotripsy systems and methods," filed Dec. 7, 2023.

Xu et al.; U.S. Appl. No. 18/568,045 entitled "All-in-one ultrasound systems and methods including histotripsy," filed Dec. 7, 2023.

Bogott et al.; U.S. Appl. No. 18/535,728 entitled "Fluidics cart and degassing system for histotripsy systems and methods," filed Dec. 11, 2023.

Grumbir et al.; U.S. Appl. No. 18/535,877 entitled "Ultrasound coupling device for histotripsy systems and methods," filed Dec. 11, 2023.

Cannata et al.; U.S. Appl. No. 18/594,843 entitled "Histotripsy systems and methods," filed Mar. 4, 2024.

Kisting et al.; Imaging for targeting, monitoring, and assessment after histotripsy: a non-invasive, non-thermal therapy for cancer; Blood Vessels; vol. 10; pp. 15-21; Mar. 2023.

Stocker et al.; Endocavity histotripsy for efficient tissue ablationRtransducer design and characterization. IEEE transactions on ultrasonics, ferroelectrics, and frequency control; 68(9); pp. 2896-2905; Jan. 28, 2021.

Woodacre et al; A low-cost miniature histotripsy transducer for precision tissue ablation. IEEE transactions on ultrasonics, ferroelectrics, and frequency control; 65(11); pp. 2131-2140; Nov. 1, 2018.

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.

Appel et al.; Stereoscopic highspeed recording of bubble filaments; Ultrasonics Sonochemistry; vol. 11(1); pp. 39-42; Jan. 2004.

Arani et al.; Transurethral prostate magnetic resonance elestography; prospective imaging requirements; Magn. Reson. Med.; 65(2); pp. 340-349; Feb. 2011.

Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.

Atchley et al.; Thresholds for cavitation produced in water by pulsed ultrasound; Ultrasonics.; vol. 26(5); pp. 280-285; Sep. 1988.

Avago Technologies; ACNV2601 High Insulation Voltage 10 MBd Digital Opotcoupler. Avago Technologies Data Sheet; pp. 1-11; Jul. 29, 2010.

Avago Technologies; Avago's ACNV2601 optocoupler is an optically coupled logic gate; Data Sheet; 2 pages; Jul. 29, 2010.

Avtech; AVR-8 Data sheet; May 23, 2004; 3 pages; retrieved from the internet (http//www.avtechpulse.com).

Bak; Rapid protytyping or rapid production? 3D printing processes move industry towards the latter; Assembly Automation; 23(4); pp. 340-345; Dec. 1, 2003.

Billson et al.; Rapid prototyping technologies for ultrasonic beam focussing in NDE; IEEE International Ultrasonic Symposium Proceedings; pp. 2472-2474; Oct. 2011.

Bjoerk et al.; Cool/MOS CP—How to make most beneficial use of the generation of super junction technology devices. Infineon Technologies AG. [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderid=db3a304412b407950112b408e8c90004&fileid=db3a304412b407950112b40ac9a40688>pp. 1, 4, 14; Feb. 2007.

Bland et al.; Surgical Oncology; McGraw Hill; Chap. 5 (Cavitron Ultrasonic Aspirator); pp. 461-462; Jan. 29, 2001.

Burdin et al.; Implementation of the laser diffraction technique for cavitation bubble investigations; Particle & Particle Systems Characterization; vol. 19; pp. 73-83; May 2002.

Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.

Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).

Chan et al.; An image-guided high intensity focused ultrasound device for uterine fibroids treatment; Medical Physics, vol. 29, pp. 2611-2620, Nov. 2002.

Clasen et al.; MR-guided radiofrequency ablation of hepatocellular carcinoma: Long-term effectiveness; J Vase Interv Radiol; 22(6); pp. 762-770; Jun. 2011.

Clement et al.; A hemisphere array for non-invasive ultrasound brain therapy and surgery; Physics in Medicine and Biology, vol. 45, p. 3707-3719, Dec. 2000.

Cline et al.; Magnetic resonance-guided thermal surgery; Magnetic Resonance in Medicine; 30(1); pp. 98-106; Jul. 1993.

Curiel et al.; Elastography for the follow-up of high-intensity focused ultrasound prostate cancer treatment: Initial comparison with MRI; Ultrasound Med. Biol; 31(11); pp. 1461-1468; Nov. 2005.

Desilets et al.; The Design of Efficient Broad-Band Piezoelectric Transducers; Sonics and Ultrasonics, IEEE Transactions on, vol. 25, pp. 115-125, May 1978.

(56)　　　　　References Cited

OTHER PUBLICATIONS

Dovedi et al.; Acquired Resistance to Fractionated Radiotherapy Can Be Overcome by Concurrent PD-LI Blockade; Cancer Research; 74(19); pp. 5458-5468; Oct. 1, 2014.

Emelianov et al.; Triplex ultrasound: Elasticity imaging to age deep venous thrombosis; Ultrasound Med Biol; 28(6); pp. 757-767; Jun. 2002.

Gateau et al.; Transcranial ultrasonic therapy based on time reversal of acoustically induced cavitation bubble signature. IEEE Transactions on Biomedical Engineering; 57(1); pp. 134-144; Sep. 18, 2009.

Giannatsis et al.; Additive fabrication technologies applied to medicine and health care: a review; The International Journal of Advanced Manufacturing Technology; 40(1-2); pp. 116-127; Jan. 2009.

Gudra et al.; Influence of acoustic impedance of multilayer acoustic systems on the transfer function of ultrasonic airborne transducers; Ultrasonics, vol. 40, pp. 457-463, May 2002.

Hall et al.; A Low Cost Compact 512 Channel Therapeutic Ultrasound System For Transcutaneous Ultrasound Surgery; AIP Conference Proceedings, Boston, MA; vol. 829, pp. 445-449, Oct. 27-29, 2005.

Hall et al.; Acoustic Access to the Prostate for Extracorporeal Ultrasound Ablation; Journal of Endourology, vol. 24, pp. 1875-1881, Nov. 2010.

Hall et al.; Histotripsy of the prostate: dose effects in a chronic canine model; Urology; 74(4); pp. 932-937; Oct. 2009 (author manuscript).

Hall et al.; Imaging feedback of tissue liquefaction (histotripsy) in ultrasound surgery; IEEE Ultrasonic Symposium, Sep. 18-21, 2005, pp. 1732-1734.

Haller et al.; Determination of acoustic cavitation probabilities and thresholds using a single focusing transducer to induce and detect acoustic cavitation events: I. Method and terminology; Ultrasound in Medicine & Biology; 44(2); pp. 377-396; Feb. 1, 2018.

Hartmann; Ultrasonic properties of poly(4-methyl pentene-1), Journal of Applied Physics, vol. 51, pp. 310-314, Jan. 1980.

Hobarth et al.; Color flow doppler sonography for extracorporal shock wave lithotripsy; Journal of Urology; 150(6); pp. 1768-1770; Dec. 1, 1993.

Holland et al.; Thresholds for transient cavitation produced by pulsed ultrasound in a controlled nuclei environment; J. Acoust. Soc. Am.; vol. 88(5); pp. 2059-2069; Nov. 1990.

Huber et al.; Influence of shock wave pressure amplitude and pulse repetition frequency on the lifespan, size and number of transient cavities in the field of an electromagnetic lithotripter; Physics in Medicine and Biology; vol. 43 (10); pp. 3113-3128; Oct. 1998.

Hynynen et al.; Tissue thermometry during ultrasound exposure; European Urology; 23(Suppl 1); pp. 12-16; (the year of publication is sufficiently earlier than the effective U.S. filing date and any foreign priority date so that the particular month of publication is not in issue)1993.

Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.

Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.

Kim et al.; Dependence of particle volume fraction on sound velocity and attenuation of EPDM composites; Ultrasonics, vol. 46, pp. 177-183, Feb. 2007.

Kim et al.; Development of a wearable robotic positioning system for noninvasive transcranial focused ultrasound stimulation. IEEE/ASME Transactions on Mechatronics; 21(5); pp. 2284-2293; Jun. 13, 2016.

Konofagou; Quo vadis elasticity imaging?; Ultrasonics; 42(1-9); pp. 331-336; Apr. 2004.

Krimholtz et al.; New equivalent circuits for elementary piezoelectric transducers; Electronics Letters, vol. 6, pp. 398-399, Jun. 1970.

Kruse et al.; Tissue characterization using magnetic resonance elastography: Preliminary results; Phys. Med. Biol; 45(6); pp. 1579-1590; Jun. 2000.

Lake et al.; Histotripsy: minimally invasive technology for prostatic tissue ablation in an in vivo canine model; Urology; 72(3); pp. 682-686; Sep. 2008.

Lauterborn et al.; Cavitation bubble dynamics studied by high speed photography and holography: part one; Ultrasonics; vol. 23; pp. 260-268; Nov. 1985.

Lensing et al.; Deep-vein thrombosis; The Lancet, vol. 353, pp. 479-485, Feb. 6, 1999.

Lin et al.; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).

Liu et al.; Real-time 2-D temperature imaging using ultrasound; IEEE Trans Biomed Eng; 57(1); pp. 12-16; Jan. 2010 (author manuscript, 16 pgs.).

Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).

Macoskey; Acoustic methods for histotripsy feedback; (Dissertation); Biomedical Engineering and Science Computing; University of Michigan 2019; 207 pages; retrived from the internet (https://deepblue.lib.umich.edu/handle/2027.42/149988) on Feb. 2022.

Manes et al.; Design of a Simplified Delay System for Ultrasound Phased Array Imaging; Sonics and Ultrasonics, IEEE Transactions on, vol. 30, pp. 350-354, Nov. 1983.

Maréchal et al.; Effect of Radial Displacement of Lens on Response of Focused Ultrasonic Transducer; Japanese Journal of Applied Physics, vol. 46, p. 3077-3085; May 15, 2007.

Maréchal et al.; Lens-focused transducer modeling using an extended KLM model; Ultrasonics, vol. 46, pp. 155-167, May 2007.

Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.

Maxwell et al.; Cavitation clouds created by shock scattering from bubbles during histotripsy; J. Acoust. Soc. Am.; 130(4); pp. 1888-1898; Oct. 2011.

Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).

Maxwell; Noninvasive thrombolysis using histotripsy pulsed ultrasound cavitation therapy; PhD Dissertation. University of Michigan, Ann Arbor, Michigan. Jun. 2012.

Maxwell et al.; In-vivo study of non-invasive thrombolysis by histotripsy in a porcine model; IEEE international Ultrasonics Symposium; IEEE; p. 220-223; Sep. 20, 2009.

Maxwell et al.; The role of compressional pressure in the formation of dense bubble clouds in histotripsy; 2009 IEEE International Ultrasonics Symposium; pp. 81-84; Sep. 20, 2009.

Miller et al.; A review of in vitro bioeffects of inertial ultrasonic cavitation from a mechanistic perspective; Ultrasound in Medicine and Biology; vol. 22; pp. 1131-1154; (the year of publication is sufficiently earlier than the effective U.S. filing date and any foreign priority date so that the particular month of publication is not in issue) 1996.

Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.

Miller et al.; Real-time elastography-based monitoring of histotripsy tissue fractionation using color doppler; Ultrasonics Symposium (IUS): 2012 IEEE International, 8 pages; Oct. 7-10, 2012.

Nightingale et al.; Analysis of contrast in images generated with transient acoustic radiation force; Ultrasound Med Biol; 32(1); pp. 61-72; Jan. 2006.

Ohl et al.; Bubble dynamics, shock waves and sonoluminescence; Phil. Trans. R. Soc. Lond. A; vol. 357; pp. 269-294; (the year of publication is sufficiently earlier than the effective U.S. filing date and any foreign priority date so that the particular month of publication is not in issue) 1999.

(56)                    References Cited

OTHER PUBLICATIONS

Okada et al.; A case of hepatocellular carcinoma treated by MR-guided focused ultrasound ablation with respiratory gating; Magn Reson Med Sci; 5(3); pp. 167-171; Oct. 2006.

Palmeri et al.; Acoustic radiation force-based elasticity imaging methods; Interface Focus; 1; pp. 553-564; Aug. 2011.

Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.

Parsons et al.; Pulsed cavitational ultrasound therapy for controlled tissue homogenization; Ultrasound in Med. & Biol.; vol. 32(1); pp. 115-129; Jan. 2006.

Pishchalnikov et al.; Cavitation Bubble Cluster Activity in the Breakage of Kidney Stones by Lithotripter Shock Waves; J Endourol.; 17(7): 435-446; Sep. 2003.

Porter et al.; Reduction in left ventricular cavitary attenuation and improvement in posterior myocardial contrast . . . ; J Am Soc Echocardiography; pp. 437-441; Jul.-Aug. 1996.

Qu et al.; Non-thermal histotripsy tumor ablation promotes abscopal immune responses that enhance cancer immunotherapy; Journal for immunotherapy of cancer; 8(1); Jan. 15, 2020.

Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.

Rosenschein et al.; Ultrasound Imaging-Guided Noninvasive Ultrasound Thrombolysis: Preclinical Results; Circulation; vol. 102; pp. 238-245, Jul. 11, 2000.

Rowland et al.; MRI study of hepatic tumours following high intensity focused ultrasound surgery; British Journal of Radiology; 70; pp. 144-153; Feb. 1997.

Roy et al.; A precise technique for the measurement of acoustic cavitation thresholds and some preliminary results; Journal of the Acoustical Society of America; vol. 78(5); pp. 1799-1805; Nov. 1985.

Sapareto et al.; Thermal dose determination in cancer therapy; Int J Radiat Oncol Biol Phys; 10(6); pp. 787-800; Apr. 1984.

Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.

Sato et al.; Experimental Investigation of Phased Array Using Tapered Matching Layers. 2002 IEEE Ultrasound Symposium. vol. 2; pp. 1235-1238, Oct. 2002.

Sferruzza et al.; Generation of high power unipolar pulse with a piezocomposite transducer; In 1999 IEEE Ultrasonics Symposium Proceedings; International Symposium (Cat. No. 99CH37027); vol. 2; pp. 1125-1128; Oct. 17, 1999.

Shung; Diagnostic Ultrasound: Imaging and Blood Flow Measurements; Taylor and Francis Group, LLC; Boca Raton, FL; 207 pages; (the year of publication is sufficiently earlier than the effective U.S. filing date and any foreign priority date so that the particular month of publication is not in issue) 2006.

Simonin et al.; Characterization of heterogeneous structure in a polymer object manufactured by stereolithography with low-frequency microechography; Journal of Materials Chemistry; vol. 6, pp. 1595-1599, Sep. 1996.

Sokolov et al.; Use of a dual-pulse lithotripter to generate a localized and intensified cavitation field; Journal of the Acoustical Society of America; vol. 110(3); pp. 1685-1695; Sep. 2001.

Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).

Souchon et al.; Visualisation of HIFU lesions using elastography of the human prostate in vivo: Preliminary results; Ultrasound Med. Biol; 29(7); pp. 1007-1015; Jul. 2003.

Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.

Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan. 28, 2014] from: (http://web archive.org/web/20110720091822/http://www.histotripsy.umich.edu/index.html> entiredocument) Jul. 2011.

Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.

Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.

Van Kervel et al.; A calculation scheme for the optimum design of ultrasonic transducers; Ultrasonics, vol. 21, pp. 134-140, May 1983.

Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.

Wikipedia; Medical ultrasound; 15 pages; retrieved from the internet (https://en.wikipedia.org/w/index.php?title=Medical_utrasound&oldid=515340960) on Jan. 12, 2018.

Wu et al.; Mechanism and dynamics of hydrodynamic-acoustic cavitation (HAC); Ultrasonics sonochemistry; vol. 49., pp. 89-96; Dec. 1, 2018.

Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.

Yan et al.; A review of rapid prototyping technologies and systems; Computer-Aided Design, vol. 28, pp. 307-318, Apr. 1996.

Zhang et al.; A fast tissue stiffness-dependent elastography for HIFU-induced lesions inspection; Ultrasonics; 51(8); pp. 857-869; Dec. 2011.

Zheng et al.; An acoustic backscatter-based method for localization of lesions induced by high-intensity focused ultrasound; Ultrasound Med Biol; 36(4); pp. 610-622; Apr. 2010.

Cannata et al.; U.S. Appl. No. 18/311,050 entitled "Histotripsy systems and methods," filed May 2, 2023.

Maxwell et al.; U.S. Appl. No. 18/329,459 entitled "Histotripsy for thrombolysis," filed Jun. 5, 2023.

Duryea et al.; U.S. Appl. No. 18/497,856 entitled "Histotripsy systems and methods," filed Oct. 31, 2023.

Duryea et al.; U.S. Appl. No. 18/498,966 entitled "Histotripsy systems and methods," filed Oct. 31, 2023.

Duryea et al.; U.S. Appl. No. 18/498,979 entitled "Histotripsy systems and methods," filed Oct. 31, 2023.

(56) References Cited

OTHER PUBLICATIONS

Xu et al.; U.S. Appl. No. 18/555,683 entitled "Design and fabrication of therapeutic ultrasound transducer with arbitrarily shaped, densely packing, removable modular elements," filed Oct. 16, 2023.

Bader et al.; For whom the bubble grows: physical principles of bubble nucleation and dynamics in histotripsy ultrasound therapy; Ultrasound in medicine & biology; 45(5); pp. 1056-1080, May 1, 2019.

Cannata et al.; U.S. Appl. No. 18/630,758 entitled "Histotripsy systems and methods," filed Apr. 9, 2024.

Cannata et al.; U.S. Appl. No. 18/642,529 entitled "Histotripsy systems and associated methods including user interfaces and workflows for treatment planning and therapy," filed Apr. 22, 2024.

Maxwell et al.; U.S. Appl. No. 18/737,731 entitled "Histotripsy for thrombolysis," filed Jun. 7, 2024.

Cannata et al.; U.S. Appl. No. 18/737,746 entitled "Histotripsy excitation sequences optimized for bubble cloud formation using shoock scattering," filed Jun. 7, 2024.

Lu et al.; Transcranial MR-guided histotripsy system; IEEE transactions on ultrasonics, ferroelectrics, and frequency control; 68(9); pp. 2917-2929; Mar. 23, 2021.

Rosnitskiy et al.; Method for designing multielement fully populated random phased arrays for ultrasound surgery applications. IEEE transactions on ultrasonics, ferroelectrics, and frequency control; 65(4); pp. 630-637; Jan. 31, 2018.

Wagner et al.; An X-ray C-arm guided automatic targeting system for histotripsy; IEEE Transactions on Biomedical Engineering; 70(2); pp. 592-602; Aug. 15, 2022.

Wijlemans et al.; Magnetic resonance-guided high-intensity focused ultrasound (MR-HIFU) ablation of liver tumours; Cancer Imaging; 12(2); pp. 387-394; Sep. 28, 2012.

Snell et al.; U.S. Appl. No. 18/886,807 entitled "Simulation software and tools for evaluating histotripsy therapy for a given pose and position of a therapy array," filed Sep. 16, 2024.

Schell et al.; U.S. Appl. No. 18/890,580 entitled "Co-registration techniques between computed tomography imaging systems and histotripsy robotic systems," filed Sep. 14, 2024.

Miller et al.; U.S. Appl. No. 18/924,812 entitled "Histotripsy systems and methods," filed Oct. 23, 2024.

Coon et al.; HIFU treatment time reduction in superficial tumours through focal zone path selection; International journal of hyperthermia; 27(5); pp. 465-481; Aug. 1, 2011.

Froghi et al.; Liver ultrasound histotripsy: novel analysis of the histotripsy site cell constituents with implications for histotripsy application in cell transplantation and cancer therapy; Bioengineering; 10(2); 276; 20 pages; Feb. 20, 2023.

Stopek; U.S. Appl. No. 19/361,539 entitled "Histotripsy systems and methods for rejected organ recovery" filed Oct. 17, 2025.

Miller; U.S. Appl. No. 19/103,752 entitled "Histotripsy systems and methods," filed Feb. 13, 2025.

Maxwell et al.; U.S. Appl. No. 19/187,641 entitled "Histotripsy for thrombolysis," filed Apr. 23, 2025.

Duryea et al.; U.S. Appl. No. 19/139,227 entitled "Systems and methods for enhancing histotripsy bubble cloud size through pulse shape optimization," filed Jun. 13, 2025.

Cannata et al.; U.S. Appl. No. 19/329,331 entitled "Histotripsy systems and associated methods including user interfaces and workflows for treatment planning and therapy," filed Sep. 15, 2025.

801

803

842

Resistance Detected

Treatment Arm

840

801

803

842

840

801

803

842

Resistance Detected

840

801

803

Resistance Detected

Treatment Arm

842

840

801

803

842

Resistance Detected

Treatment Arm

840

801

803

842

Resistance Detected

840

801

803

842

840

801

803

842

Resistance Detected

840

801

803

842

840

801

803

842

840

801

803

842

840

801

803

842

840

Resistance Detected

801

803

842

840

Resistance Detected

Figure 9:
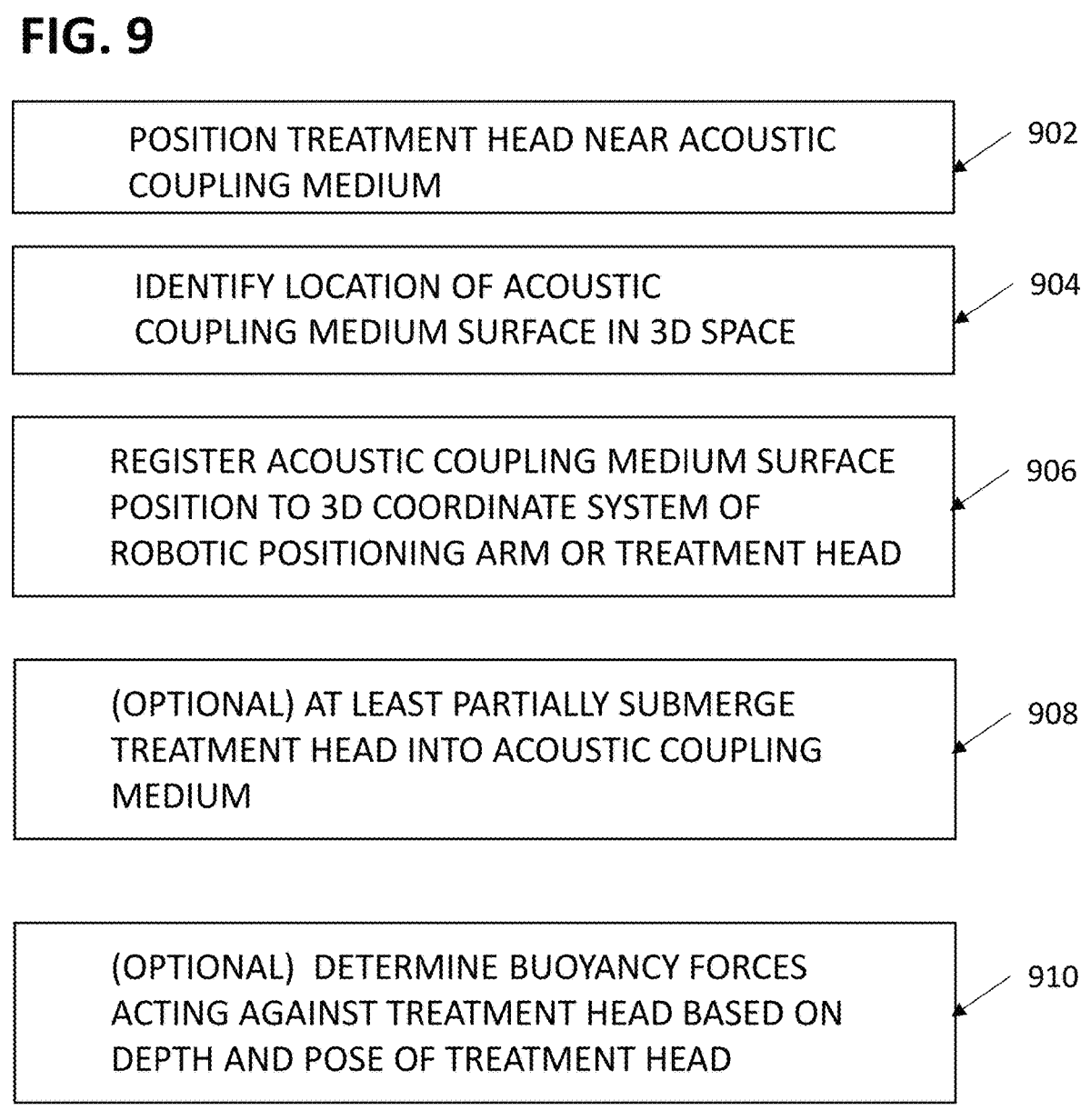

POSITION TREATMENT HEAD NEAR ACOUSTIC COUPLING MEDIUM — 902

IDENTIFY LOCATION OF ACOUSTIC COUPLING MEDIUM SURFACE IN 3D SPACE — 904

REGISTER ACOUSTIC COUPLING MEDIUM SURFACE POSITION TO 3D COORDINATE SYSTEM OF ROBOTIC POSITIONING ARM OR TREATMENT HEAD — 906

(OPTIONAL) AT LEAST PARTIALLY SUBMERGE TREATMENT HEAD INTO ACOUSTIC COUPLING MEDIUM — 908

(OPTIONAL) DETERMINE BUOYANCY FORCES ACTING AGAINST TREATMENT HEAD BASED ON DEPTH AND POSE OF TREATMENT HEAD — 910

FIG. 10

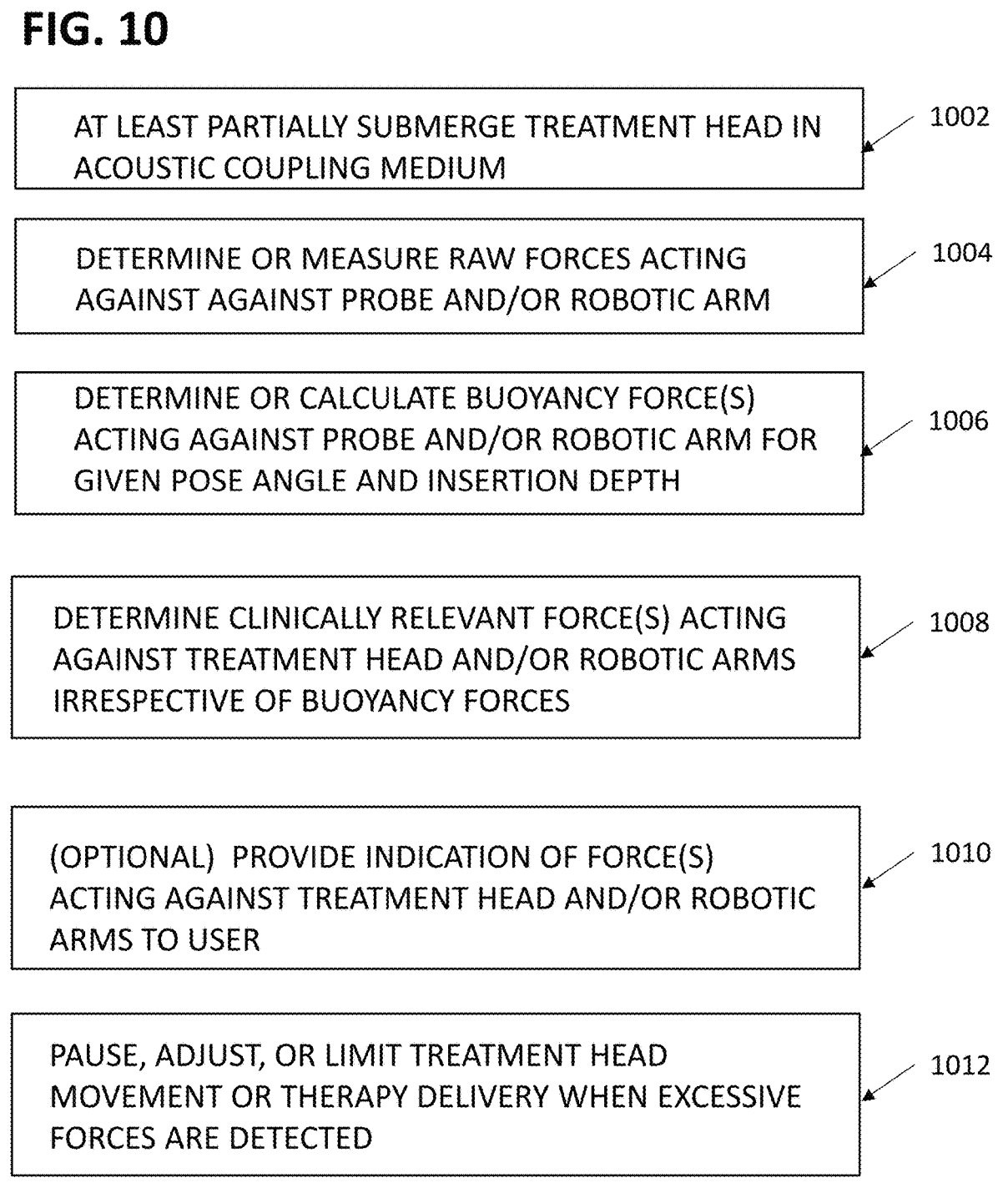

AT LEAST PARTIALLY SUBMERGE TREATMENT HEAD IN ACOUSTIC COUPLING MEDIUM — 1002

DETERMINE OR MEASURE RAW FORCES ACTING AGAINST AGAINST PROBE AND/OR ROBOTIC ARM — 1004

DETERMINE OR CALCULATE BUOYANCY FORCE(S) ACTING AGAINST PROBE AND/OR ROBOTIC ARM FOR GIVEN POSE ANGLE AND INSERTION DEPTH — 1006

DETERMINE CLINICALLY RELEVANT FORCE(S) ACTING AGAINST TREATMENT HEAD AND/OR ROBOTIC ARMS IRRESPECTIVE OF BUOYANCY FORCES — 1008

(OPTIONAL)  PROVIDE INDICATION OF FORCE(S) ACTING AGAINST TREATMENT HEAD AND/OR ROBOTIC ARMS TO USER — 1010

PAUSE, ADJUST, OR LIMIT TREATMENT HEAD MOVEMENT OR THERAPY DELIVERY WHEN EXCESSIVE FORCES ARE DETECTED — 1012

HISTOTRIPSY SYSTEMS AND METHODS

CROSS REFERENCE TO RELATED APPLICATIONS

This patent application claims priority to U.S. provisional patent application No. 63/381,888, titled "HISTOTRIPSY SYSTEMS AND METHODS" and filed Nov. 1, 2022, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure details novel high intensity therapeutic ultrasound (HITU) systems configured to produce acoustic cavitation, methods, devices and procedures for the minimally and non-invasive treatment of healthy, diseased and/or injured tissue. The acoustic cavitation systems and methods described herein, also referred to Histotripsy, may include transducers, drive electronics, positioning robotics, imaging systems, and integrated treatment planning and control software to provide comprehensive treatment and therapy for soft tissues in a patient.

BACKGROUND

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high amplitude acoustic pulses with low duty cycle.

Compared with conventional focused ultrasound technologies, Histotripsy has important advantages: 1) the destructive process at the focus is mechanical, not thermal; 2) cavitation appears bright on ultrasound imaging thereby confirming correct targeting and localization of treatment; 3) treated tissue generally, but not always, appears darker (more hypoechoic) on ultrasound imaging, so that the operator knows what has been treated; and 4) Histotripsy produces lesions in a controlled and precise manner. It is important to emphasize that unlike thermal ablative technologies such as microwave, radiofrequency, high-intensity focused ultrasound (HIFU) cryo or radiation, Histotripsy relies on the mechanical action of cavitation for tissue destruction and not on heat, cold or ionizing energy.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 9 is a flowchart describing a method of performing therapy with an ultrasound system.

FIG. 10 is a flowchart describing a method of performing therapy with an ultrasound system.

SUMMARY OF THE DISCLOSURE

Figure 1A:
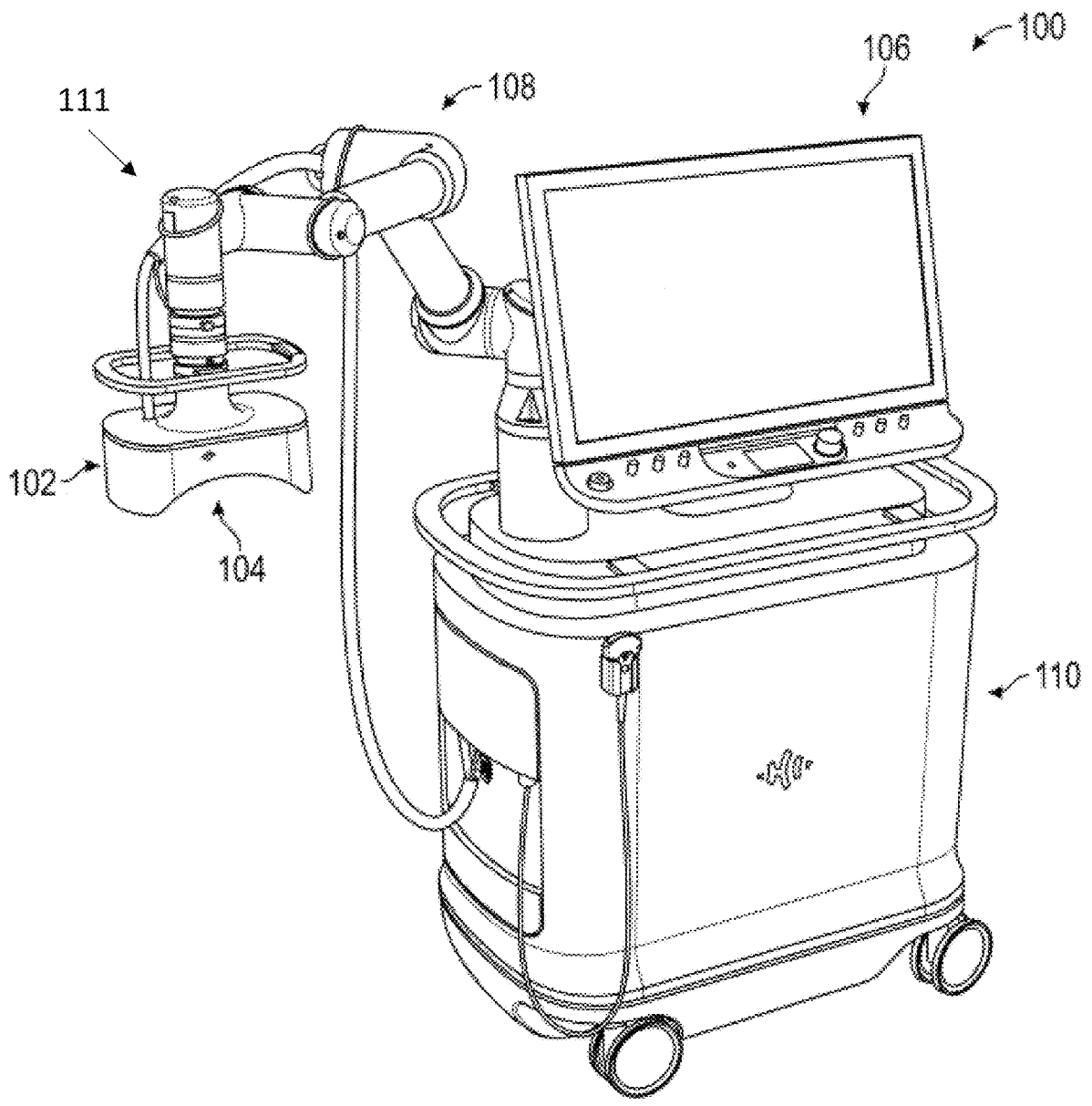
FIGS. 1A-1B illustrate an ultrasound imaging and therapy system.

A method of monitoring forces against an ultrasound treatment head is provided, comprising: at least partially submerging the ultrasound treatment head in an acoustic coupling medium; determining raw forces acting against the ultrasound treatment head; determining buoyancy forces acting against the treatment head for a given pose angle and insertion depth of the ultrasound treatment head; determining clinically relevant forces acting against the ultrasound treatment head irrespective of the buoyancy forces; and adjusting ultrasound treatment head movement in response to clinically relevant forces that exceed at least one safety threshold.

In some aspects, determining the raw forces acting against the ultrasound treatment head comprises measuring the raw forces with one or more force sensors disposed on or within the ultrasound treatment head.

In one aspect, determining the raw forces acting against the ultrasound treatment head comprises measuring the raw forces with one or more force sensors disposed on or within a robotic positioning arm coupled to the ultrasound treatment head.

In some aspects, the given pose angle is determined by one or more processors operatively coupled to the ultrasound treatment head.

In some aspects, the insertion depth is determined based on a surface level of the acoustic coupling medium.

In one aspect, determining the buoyancy forces further comprises calculating the buoyancy forces with a model equation with best fit coefficients that uses the insertion depth and pose angle as inputs.

In some aspects, determining the clinically relevant forces comprises subtracting the buoyancy forces from the raw forces.

In other aspects, the acoustic coupling medium is disposed within a coupling container placed on a patient.

In one aspect, the method includes at least partially submerging the ultrasound treatment head comprises moving the ultrasound treatment head with at least one robotic positioning arm.

In some aspects, determining buoyancy forces further comprises repeatedly or continuously determining buoyancy forces acting against the ultrasound treatment head for a given pose angle and insertion depth of the ultrasound treatment head.

In other aspects, the buoyancy forces are determined in real time.

In some aspects, the buoyancy forces are determined from a lookup table.

In other aspects, the method includes indicating the clinically relevant forces to a user In one aspect, the method includes providing a visual indicator of the clinically relevant forces to a user on a graphical user interface.

In some aspects, the visual indicator indicates if the clinically relevant forces fall within a low range of forces, a medium range of forces, or a high range of forces.

In other aspects, indicating further comprises displaying a color coded force indication system to the user.

In some aspects, indicating further comprises displaying words that indicate to the user a level of the clinical relevant forces.

In one aspect, indicating further comprises displaying the raw forces.

In some aspects, indicating further comprises indicating a direction or location on the treatment head where the clinically relevant forces are sensed or measured.

In some aspects, the at least one safety threshold comprises a moderate or medium safety threshold, and wherein adjusting treatment head movement further comprises limiting treatment head movement speed to a maximum movement speed.

In some aspects, the at least one safety threshold comprises a moderate or medium safety threshold, and wherein adjusting treatment head movement further comprises limiting treatment head movement in the direction of the detected clinically relevant force that exceeds the moderate or medium safety threshold.

In one aspect, the at least one safety threshold comprises a high or excessive safety threshold, and wherein adjusting treatment head movement further comprises terminating treatment head movement.

In some aspects, the at least one safety threshold comprises a high or excessive safety threshold, and wherein adjusting treatment head movement further comprises moving the treatment head in the opposite direction of the clinically relevant force that exceeds the high or excessive safety threshold.

A system, comprising: a robotic positioning arm; an ultrasound treatment head coupled to the robotic positioning arm; at least one force sensor coupled to the robotic positioning arm and/or the ultrasound treatment head; an acoustic coupling container containing an acoustic coupling medium; a graphical user interface; and one or more processors operatively coupled to the robotic positioning arm, the at least one force sensor, and the ultrasound treatment head, the one or more processors being configured to: control the robotic positioning arm to at least partially submerge the ultrasound treatment head in the acoustic coupling medium determine raw forces acting against the ultrasound treatment head with the at least one force sensor; determine buoyancy forces acting against the treatment head for a given pose angle and insertion depth of the ultrasound treatment head; determine clinically relevant forces acting against the ultrasound treatment head irrespective of the buoyancy forces; and provide an indication of clinically relevant forces acting upon the ultrasound treatment head to the user on the graphical user interface.

In some aspects, the one or more processors are further configured to adjust movement of the robotic positioning arm in response to the clinically relevant forces that exceed at least one safety threshold.

In other aspects, the at least one force sensor is disposed on or within the ultrasound treatment head.

In some aspects, the at least one force sensor is disposed on or within the robotic positioning arm.

In some aspects, the given pose angle is determined by the one or more processors.

In one aspect, the insertion depth is determined by the one or more processors based on a surface level of the acoustic coupling medium.

In some aspects, the one or more processors are configured to determine the buoyancy forces by calculating the buoyancy forces with a model equation with best fit coefficients that uses the insertion depth and given pose angle as inputs.

In some aspects, the one or more processors are configured to determine the clinically relevant forces by subtracting the buoyancy forces from the raw forces.

In other aspects, the one or more processors are configured to repeatedly or continuously determine buoyancy forces acting against the ultrasound treatment head for a given pose angle and insertion depth of the ultrasound treatment head.

In some aspects, the one or more processors are configured to determine the buoyancy forces in real time.

In other aspects, the one or more processors are configured to determine the buoyancy forces from a lookup table.

In some aspects, the indication comprises a visual indicator of the clinically relevant forces on the graphical user interface.

In one aspect, the visual indicator indicates if the clinically relevant forces fall within an acceptable range of forces, an increased range of forces, or a dangerous range of forces.

In some aspects, the visual indicator comprises a color coded force indication system.

In one aspect, the visual indicator includes words that indicate to the user a level of the clinical relevant forces.

In some aspects, the visual indicator includes a numeric indicator of the raw forces.

In one aspect, the visual indicator includes a direction or location on the treatment head where the clinically relevant forces are sensed or measured.

In some aspects, the one or more processors are configured to limit treatment head movement speed to a maximum movement speed if the clinically relevant forces exceed a medium safety threshold.

In another aspect, the one or more processors are configured to limit treatment head movement in the direction of detected clinically relevant forces that exceed a medium safety threshold.

In some aspects, the one or more processors are configured to terminate treatment head movement if the detected clinically relevant forces exceed an excessive safety threshold In one aspect, the one or more processors are configured to move the treatment head in the opposite direction of detected clinically relevant forces that exceed an excessive safety threshold.

A histotripsy system is provided, comprising: a treatment head comprising an array of transducer elements; a robotic arm coupled to the treatment head; one or more force sensors disposed on the robotic arm configured to sense force data applied to at least one location on the treatment head and to communicate the force data to at least one processor of the histotripsy system; and a user interface configured to present the force data to a user.

In some aspects, the system comprises an acoustic coupling container configured to acoustically couple the treatment head to a patient.

In one aspect, the user interface includes a display for displaying the force data to the user.

In some aspects, the displayed force data is color coded corresponding to various levels of force applied against the treatment head.

In other aspects, the one or more force sensors are configured for repeatedly, intermittently, periodically, or continuously sensing force data.

In some aspects, the at least one processor and/or the robotic arm is configured to make velocity adjustments on the treatment head based on the force data.

In other aspects, the force data comprises forces selected from the group consisting of buoyancy forces, resistance forces, water pressure forces, and forces resulting from movement of the treatment head.

In some aspects, the at least one processor is further configured to adjust, treatment head and/or robotic arm movement in response to force data that exceeds at least one safety threshold.

A method is provided, comprising: positioning an acoustic coupling container and an acoustic coupling medium on a patient; identifying a surface location of the acoustic coupling medium in 3D space; registering the surface location in 3D space to a 3D coordinate system of an ultrasound treatment head; at least partially submerging the ultrasound treatment head into the acoustic coupling medium; and determining buoyancy forces acting against the ultrasound treatment head based on a depth and pose of the treatment head within the acoustic coupling medium.

DETAILED DESCRIPTION

The system, methods and devices of the disclosure may be used for open surgical, minimally invasive surgical (laparoscopic and percutaneous), robotic surgical (integrated into a robotically-enabled medical system), endoscopic or completely transdermal extracorporeal non-invasive acoustic cavitation for the treatment of healthy, diseased and/or injured tissue including but not limited to tissue destruction, cutting, skeletonizing and ablation. Furthermore, due to tissue selective properties, histotripsy may be used to create a cytoskeleton that allows for subsequent tissue regeneration either de novo or through the application of stem cells and other adjuvants. Finally, histotripsy can be used to cause the release of delivered agents such as chemotherapy and immunotherapy by locally causing the release of these agents by the application of acoustic energy to the targets. As will be described below, the acoustic cavitation system may include various sub-systems, including a Cart, Therapy, Integrated Imaging, Robotics, Coupling and Software. The system also may comprise various Other Components, Ancillaries and Accessories, including but not limited to computers, cables and connectors, networking devices, power supplies, displays, drawers/storage, doors, wheels, and various simulation and training tools, etc. All systems, methods and means creating/controlling/delivering histotripsy are considered to be a part of this disclosure, including new related inventions disclosed herein.

FIG. 1A generally illustrates histotripsy system 100 according to the present disclosure, comprising a therapy transducer 102, an imaging system 104, a display and control panel 106, a robotic positioning arm 108, and a cart 110. The system can further include an ultrasound coupling interface and a source of coupling medium, not shown. The robotic positioning arm 108 may include one or more sensors 111 integrated within configured to measure one or more parameters of the positioning arm, including arm pose (e.g., angle) and/or forces acting against the positioning arm (or being applied by the positioning arm). The sensors can be integrated within the arm at selected locations (e.g., at each joint) to provide sensing capabilities for one or more links of the positioning arm. Additionally, the sensors 111 can be positioned at or near the connection to the therapy transducer or treatment head 102 to provide pose or force information pertaining to the treatment head (e.g., the pose of the treatment head or forces acting against or being applied by the treatment head). These sensors can include but not be limited to gyroscopic sensors, accelerometers, force sensors, force transducers, or any other known sensors in the art.

The cart 110 may include one or more processors configured to control operation of the system, including controlling or coordinating movement and positioning of the treatment head via the robotic positioning arm. The one or more processors can control a signal generator to provide ultrasound pulses or waveforms to the treatment head for the delivery of histotripsy energy to a target tissue volume. Additionally, the one or more processors can be in electronic communication with any sensors 111 or other features of the system to assess sensed signals or parameters and adjust therapy or alert the user regarding system features or events. For example, the one or more processors may be configured to assess a depth and/or pose angle of the treatment head within an acoustic coupling medium, determine buoyancy forces acting against the treatment head, and provide an indication of the true forces acting against the treatment head during a therapy procedure.

Figure 1B:
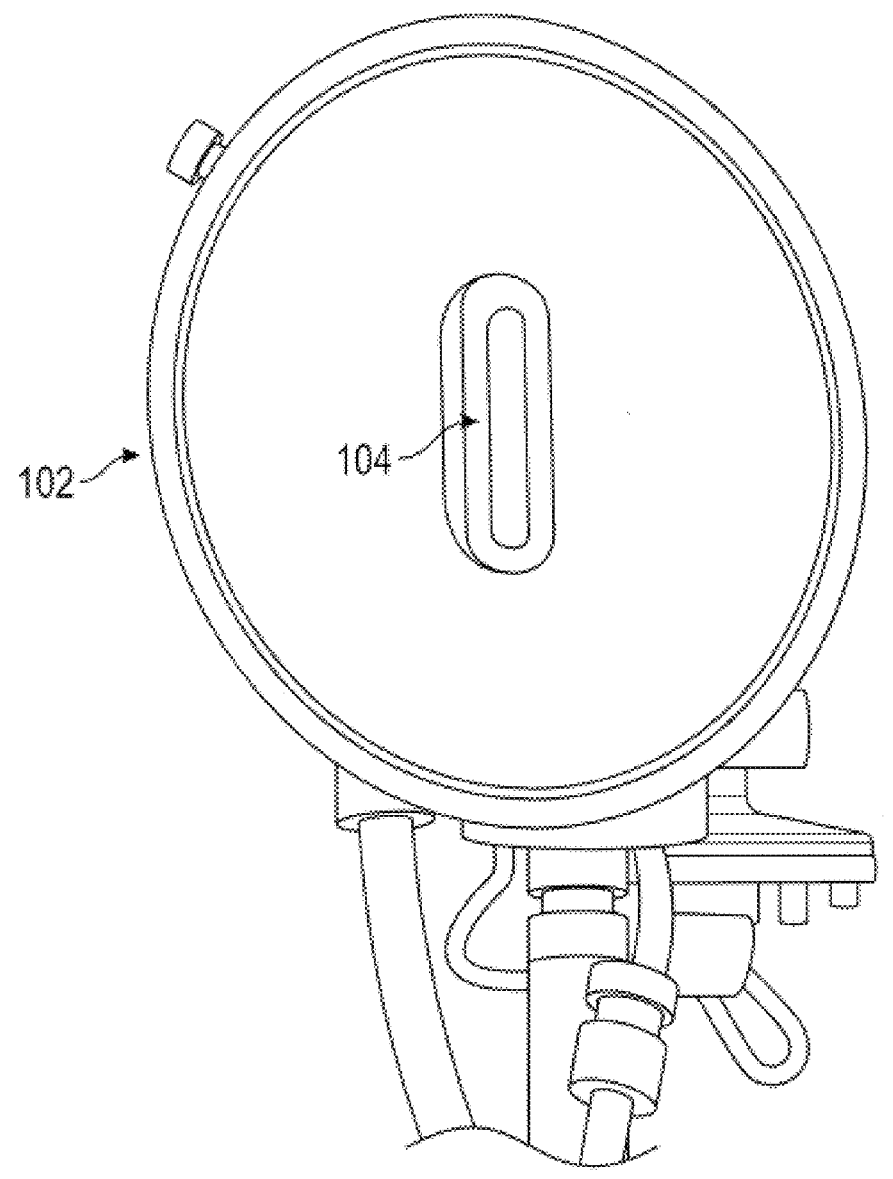

FIG. 1B is a bottom view of the therapy transducer 102 and the imaging system 104. As shown, the imaging system can be positioned in the center of the therapy transducer. However, other embodiments can include the imaging system positioned in other locations within the therapy transducer, or even directly integrated into the therapy transducer. In some embodiments, the imaging system is configured to produce real-time imaging at a focal point of the therapy transducer. The system also allows for multiple imaging transducers to be located within the therapy transducer to provide multiple views of the target tissue simultaneously and to integrate these images into a single 3-D image.

The histotripsy system may comprise one or more of various sub-systems, including a Therapy sub-system that can create, apply, focus and deliver acoustic cavitation/histotripsy through one or more therapy transducers, Integrated Imaging sub-system (or connectivity to) allowing real-time visualization of the treatment site and histotripsy effect through-out the procedure, a Robotics positioning sub-system to mechanically and/or electronically steer the therapy transducer, further enabled to connect/support or interact with a Coupling sub-system to allow acoustic coupling between the therapy transducer and the patient, and Software to communicate, control and interface with the system and computer-based control systems (and other external systems) and various Other Components, Ancillaries and Accessories, including one or more user interfaces and displays, and related guided work-flows, all working in part or together. The system may further comprise various fluidics and fluid management components, including but not limited to, pumps, valve and flow controls, temperature and degassing controls, and irrigation and aspiration capabilities, as well as providing and storing fluids. It may also contain various power supplies and protectors.

As described above, the histotripsy system may include integrated imaging. However, in other embodiments, the histotripsy system can be configured to interface with separate imaging systems, such as C-arm, fluoroscope, cone beam CT, MRI, etc., to provide real-time imaging during histotripsy therapy. In some embodiments, the histotripsy system can be sized and configured to fit within a C-arm, fluoroscope, cone beam CT, MRI, etc.

Cart

The Cart 110 may be generally configured in a variety of ways and form factors based on the specific uses and procedures. In some cases, systems may comprise multiple Carts, configured with similar or different arrangements. In some embodiments, the cart may be configured and arranged to be used in a radiology environment and in some cases in concert with imaging (e.g., CT, cone beam CT and/or MRI scanning). In other embodiments, it may be arranged for use in an operating room and a sterile environment for open surgical or laparoscopic surgical and endoscopic application, or in a robotically enabled operating room, and used alone, or as part of a surgical robotics procedure wherein a surgical robot conducts specific tasks before, during or after use of the system and delivery of acoustic cavitation/ histotripsy. As such and depending on the procedure environment based on the aforementioned embodiments, the cart may be positioned to provide sufficient work-space and access to various anatomical locations on the patient (e.g., torso, abdomen, flank, head and neck, etc.), as well as providing work-space for other systems (e.g., anesthesia cart, laparoscopic tower, surgical robot, endoscope tower, etc.).

The Cart may also work with a patient surface (e.g., table or bed) to allow the patient to be presented and repositioned in a plethora of positions, angles and orientations, including allowing changes to such to be made pre, peri and post-procedurally. It may further comprise the ability to interface and communicate with one or more external imaging or image data management and communication systems, not limited to ultrasound, CT, fluoroscopy, cone beam CT, PET, PET/CT, MRI, optical, ultrasound, and image fusion and or image flow, of one or more modalities, to support the procedures and/or environments of use, including physical/ mechanical interoperability (e.g., compatible within cone beam CT work-space for collecting imaging data pre, peri and/or post histotripsy) and to provide access to and display of patient medical data including but not limited to laboratory and historical medical record data.

In some embodiments one or more Carts may be configured to work together. As an example, one Cart may comprise a bedside mobile Cart equipped with one or more Robotic arms enabled with a Therapy transducer, and Therapy generator/amplifier, etc., while a companion cart working in concert and at a distance of the patient may comprise Integrated Imaging and a console/display for controlling the Robotic and Therapy facets, analogous to a surgical robot and master/slave configurations.

In some embodiments, the system may comprise a plurality of Carts, all slave to one master Cart, equipped to conduct acoustic cavitation procedures. In some arrangements and cases, one Cart configuration may allow for storage of specific sub-systems at a distance reducing operating room clutter, while another in concert Cart may comprise essentially bedside sub-systems and componentry (e.g., delivery system and therapy).

One can envision a plethora of permutations and configurations of Cart design, and these examples are in no way limiting the scope of the disclosure.

Histotripsy

Histotripsy comprises short, high amplitude, focused ultrasound pulses to generate a dense, energetic, "bubble cloud", capable of the targeted fractionation and destruction of tissue. Histotripsy is capable of creating controlled tissue erosion when directed at a tissue interface, including tissue/ fluid interfaces, as well as well-demarcated tissue fractionation and destruction, at sub-cellular levels, when it is targeted at bulk tissue. Unlike other forms of ablation, including thermal and radiation-based modalities, histotripsy does not rely on heat cold or ionizing (high) energy to treat tissue. Instead, histotripsy uses acoustic cavitation generated at the focus to mechanically effect tissue structure, and in some cases liquefy, suspend, solubilize and/or destruct tissue into sub-cellular components.

Histotripsy can be applied in various forms, including: 1) Intrinsic-Threshold Histotripsy: Delivers pulses with a 1-2 cycles of high amplitude negative/tensile phase pressure exceeding the intrinsic threshold to generate cavitation in the medium (e.g., −24-28 MPa for water-based soft tissue), 2) Shock-Scattering Histotripsy: Delivers typically pulses 3-20 cycles in duration. The shockwave (positive/compressive phase) scattered from an initial individual microbubble generated forms inverted shockwave, which constructively interfere with the incoming negative/tensile phase to form high amplitude negative/rarefactional phase exceeding the intrinsic threshold. In this way, a cluster of cavitation microbubbles is generated. The amplitude of the tensile phases of the pulses is sufficient to cause bubble nuclei in the medium to undergo inertial cavitation within the focal zone throughout the duration of the pulse. These nuclei scatter the incident shockwaves, which invert and constructively interfere with the incident wave to exceed the threshold for intrinsic nucleation, and 3) Boiling Histotripsy: Employs pulses roughly 1-20 ms in duration. Absorption of the shocked pulse rapidly heats the medium, thereby reducing the threshold for intrinsic nuclei. Once this intrinsic threshold coincides with the peak negative pressure of the incident wave, boiling bubbles form at the focus.

The large pressure generated at the focus causes a cloud of acoustic cavitation bubbles to form above certain thresholds, which creates localized stress and strain in the tissue and mechanical breakdown without significant heat deposition. At pressure levels where cavitation is not generated, minimal effect is observed on the tissue at the focus. This cavitation effect is observed only at pressure levels significantly greater than those which define the inertial cavitation threshold in water for similar pulse durations, on the order of 10 to 30 MPa peak negative pressure.

Histotripsy may be performed in multiple ways and under different parameters. It may be performed totally non-invasively by acoustically coupling a focused ultrasound transducer over the skin of a patient and transmitting acoustic pulses transcutaneously through overlying (and intervening) tissue to the focal zone (treatment zone and site). The application of histotripsy is not limited to a transdermal approach but can be applied through any means that allows contact of the transducer with tissue including open surgical laparoscopic surgical, percutaneous and robotically mediated surgical procedures. It may be further targeted, planned, directed and observed under direct visualization, via ultrasound imaging, given the bubble clouds generated by histotripsy may be visible as highly dynamic, echogenic regions on, for example, B Mode ultrasound images, allowing continuous visualization through its use (and related procedures). Likewise, the treated and fractionated tissue shows a dynamic change in echogenicity (typically a reduction), which can be used to evaluate, plan, observe and monitor treatment.

Generally, in histotripsy treatments, ultrasound pulses with 1 or more acoustic cycles are applied, and the bubble cloud formation relies on the pressure release scattering of the positive shock fronts (sometimes exceeding 100 MPa, P+) from initially initiated, sparsely distributed bubbles (or a single bubble). This is referred to as the "shock scattering mechanism".

This mechanism depends on one (or a few sparsely distributed) bubble(s) initiated with the initial negative half cycle(s) of the pulse at the focus of the transducer. A cloud of microbubbles then forms due to the pressure release backscattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative pressure, but also the number of acoustic cycles and the amplitudes of the positive shocks. Without at least one intense shock front developed by nonlinear propagation, no dense bubble clouds are generated when the peak negative half-cycles are below the intrinsic threshold.

When ultrasound pulses less than 2 cycles are applied, shock scattering can be minimized, and the generation of a dense bubble cloud depends on the negative half cycle(s) of the applied ultrasound pulses exceeding an "intrinsic threshold" of the medium. This is referred to as the "intrinsic threshold mechanism".

This threshold can be in the range of 26-30 MPa for soft tissues with high water content, such as tissues in the human body. In some embodiments, using this intrinsic threshold mechanism, the spatial extent of the lesion may be well-defined and more predictable. With peak negative pressures (P−) not significantly higher than this threshold, sub-wavelength reproducible lesions as small as half of the −6 dB beam width of a transducer may be generated.

With high-frequency Histotripsy pulses, the size of the smallest reproducible lesion becomes smaller, which is beneficial in applications that require precise lesion generation. However, high-frequency pulses are more susceptible to attenuation and aberration, rendering problematical treatments at a larger penetration depth (e.g., ablation deep in the body) or through a highly aberrative medium (e.g., transcranial procedures, or procedures in which the pulses are transmitted through bone(s)). Histotripsy may further also be applied as a low-frequency "pump" pulse (typically <2 cycles and having a frequency between 100 kHz and 1 MHz) can be applied together with a high-frequency "probe" pulse (typically <2 cycles and having a frequency greater than 2 MHz, or ranging between 2 MHz and 10 MHz) wherein the peak negative pressures of the low and high-frequency pulses constructively interfere to exceed the intrinsic threshold in the target tissue or medium. The low-frequency pulse, which is more resistant to attenuation and aberration, can raise the peak negative pressure P− level for a region of interest (ROI), while the high-frequency pulse, which provides more precision, can pin-point a targeted location within the ROI and raise the peak negative pressure P− above the intrinsic threshold. This approach may be referred to as "dual frequency", "dual beam histotripsy" or "parametric histotripsy."

Additional systems, methods and parameters to deliver optimized histotripsy, using shock scattering, intrinsic threshold, and various parameters enabling frequency compounding and bubble manipulation, are herein included as part of the system and methods disclosed herein, including additional means of controlling said histotripsy effect as pertains to steering and positioning the focus, and concurrently managing tissue effects (e.g., prefocal thermal collateral damage) at the treatment site or within intervening tissue. Further, it is disclosed that the various systems and methods, which may include a plurality of parameters, such as but not limited to, frequency, operating frequency, center frequency, pulse repetition frequency, pulses, bursts, number of pulses, cycles, length of pulses, amplitude of pulses, pulse period, delays, burst repetition frequency, sets of the former, loops of multiple sets, loops of multiple and/or different sets, sets of loops, and various combinations or permutations of, etc., are included as a part of this disclosure, including future envisioned embodiments of such.

Therapy Components

The Therapy sub-system may work with other sub-systems to create, optimize, deliver, visualize, monitor and control acoustic cavitation, also referred to herein and in following as "histotripsy", and its derivatives of, including boiling histotripsy and other thermal high frequency ultrasound approaches. It is noted that the disclosed inventions may also further benefit other acoustic therapies that do not comprise a cavitation, mechanical or histotripsy component. The therapy sub-system can include, among other features, an ultrasound therapy transducer and a pulse generator system configured to deliver ultrasound pulses into tissue.

In order to create and deliver histotripsy and derivatives of histotripsy, the therapy sub-system may also comprise components, including but not limited to, one or more function generators, amplifiers, therapy transducers and power supplies.

The therapy transducer can comprise a single element or multiple elements configured to be excited with high amplitude electric pulses (>1000V or any other voltage that can cause harm to living organisms). The amplitude necessary to drive the therapy transducers for Histotripsy vary depending on the design of the transducer and the materials used (e.g., solid or polymer/piezoelectric composite including ceramic or single crystal) and the transducer center frequency which is directly proportional to the thickness of the piezo-electric material. Transducers therefore operating at a high frequency require lower voltage to produce a given surface pressure than is required by low frequency therapy transducers. In some embodiments, the transducer elements are formed using a piezoelectric-polymer composite material or a solid piezoelectric material. Further, the piezoelectric material can be of polycrystalline/ceramic or single crystalline formulation. In some embodiments the transducer elements can be formed using silicon using MEMs technology, including CMUT and PMUT designs.

In some embodiments, the function generator may comprise a field programmable gate array (FPGA) or other suitable function generator. The FPGA may be configured with parameters disclosed previously herein, including but not limited to frequency, pulse repetition frequency, bursts, burst numbers, where bursts may comprise pulses, numbers of pulses, length of pulses, pulse period, delays, burst repetition frequency or period, where sets of bursts may comprise a parameter set, where loop sets may comprise various parameter sets, with or without delays, or varied delays, where multiple loop sets may be repeated and/or new loop sets introduced, of varied time delay and independently controlled, and of various combinations and permutations of such, overall and throughout.

In some embodiments, the generator or amplifier may be configured to be a universal single-cycle or multi-cycle pulse generator, and to support driving via Class D or inductive driving, as well as across all envisioned clinical applications, use environments, also discussed in part later in this disclosure. In other embodiments, the class D or inductive current driver may be configured to comprise transformer and/or auto-transformer driving circuits to further provide step up/down components, and in some cases, to preferably allow a step up in the amplitude. They may also comprise specific protective features, to further support the system, and provide capability to protect other parts of the system (e.g., therapy transducer and/or amplifier circuit components) and/or the user, from various hazards, including but not limited to, electrical safety hazards, which may potentially lead to use environment, system and therapy system, and user harms, damage or issues.

Disclosed generators may allow and support the ability of the system to select, vary and control various parameters (through enabled software tools), including, but not limited to those previously disclosed, as well as the ability to start/stop therapy, set and read voltage level, pulse and/or burst repetition frequency, number of cycles, duty ratio, channel enabled and delay, etc., modulate pulse amplitude on a fast time-scale independent of a high voltage supply, and/or other service, diagnostic or treatment features.

In some embodiments, the Therapy sub-system and/or components of, such as the amplifier, may comprise further integrated computer processing capability and may be networked, connected, accessed, and/or be removable/portable, modular, and/or exchangeable between systems, and/or driven/commanded from/by other systems, or in various combinations. Other systems may include other acoustic cavitation/histotripsy, HIFU, HITU, radiation therapy, radiofrequency, microwave, and cryoablation systems, navigation and localization systems, open surgical, laparoscopic, single incision/single port, endoscopic and non-invasive surgical robots, laparoscopic or surgical towers comprising other energy-based or vision systems, surgical system racks or booms, imaging carts, etc.

In some embodiments, one or more amplifiers may comprise a Class D amplifier and related drive circuitry including matching network components. Depending on the transducer element electric impedance and choice of the matching network components (e.g., an LC circuit made of an inductor L1 in series and the capacitor C1 in parallel), the combined impedance can be aggressively set low in order to have high amplitude electric waveform necessary to drive the transducer element. The maximum amplitude that Class D amplifiers is dependent on the circuit components used, including the driving MOSFET/IGBT transistors, matching network components or inductor, and transformer or auto-transformer, and of which may be typically in the low kV (e.g., 1-3 kV) range.

Therapy transducer element(s) are excited with an electrical waveform with an amplitude (voltage) to produce a pressure output sufficient for Histotripsy therapy. The excitation electric field can be defined as the necessary waveform voltage per thickness of the piezoelectric element. For example, because a piezoelectric element operating at 1 MHz transducer is half the thickness of an equivalent 500 kHz element, it will require half the voltage to achieve the same electric field and surface pressure.

The Therapy sub-system may also comprise therapy transducers of various designs and working parameters, supporting use in various procedures (and procedure settings). Systems may be configured with one or more therapy transducers, that may be further interchangeable, and work with various aspects of the system in similar or different ways (e.g., may interface to a robotic arm using a common interface and exchange feature, or conversely, may adapt to work differently with application specific imaging probes, where different imaging probes may interface and integrate with a therapy transducer in specifically different ways).

Therapy transducers may be configured of various parameters that may include size, shape (e.g., rectangular or round; anatomically curved housings, etc.), geometry, focal length, number of elements, size of elements, distribution of elements (e.g., number of rings, size of rings for annular patterned transducers), frequency, enabling electronic beam steering, etc. Transducers may be composed of various materials (e.g., piezoelectric, silicon, etc.), form factors and types (e.g., machined elements, chip-based, etc.) and/or by various methods of fabrication of.

Transducers may be designed and optimized for clinical applications (e.g., abdominal tumors, peripheral vascular disease, fat ablation, etc.) and desired outcomes (e.g., acoustic cavitation/histotripsy without thermal injury to intervening tissue), and affording a breadth of working ranges, including relatively shallow and superficial targets (e.g., thyroid or breast nodules), versus, deeper or harder to reach targets, such as central liver or brain tumors. They may be configured to enable acoustic cavitation/histotripsy under various parameters and sets of, as enabled by the aforementioned system components (e.g., function generator and amplifier, etc.), including but not limited to frequency, pulse repetition rate, pulses, number of pulses, pulse length, pulse period, delays, repetitions, sync delays, sync period, sync pulses, sync pulse delays, various loop sets, others, and permutations of. The transducer may also be designed to allow for the activation of a drug payload either deposited in tissue through various means including injection, placement or delivery in micelle or nanostructures.

Integrated Imaging

The disclosed system may comprise various imaging modalities to allow users to visualize, monitor and collect/use feedback of the patient's anatomy, related regions of interest and treatment/procedure sites, as well as surrounding and intervening tissues to assess, plan and conduct procedures, and adjust treatment parameters as needed. Imaging modalities may comprise various ultrasound, x-ray, CT, MRI, PET, fluoroscopy, optical, contrast or agent enhanced versions, and/or various combinations of. It is further disclosed that various image processing and characterization technologies may also be utilized to afford enhanced visualization and user decision making. These may be selected or commanded manually by the user or in an automated fashion by the system. The system may be configured to allow side by side, toggling, overlays, 3D reconstruction, segmentation, registration, multi-modal image fusion, image flow, and/or any methodology affording the user to identify, define and inform various aspects of using imaging during the procedure, as displayed in the various system user interfaces and displays. Examples may include locating, displaying and characterizing regions of interest, organ systems, potential treatment sites within, with on and/or surrounding organs or tissues, identifying critical structures such as ducts, vessels, nerves, ureters, fissures, capsules, tumors, tissue trauma/injury/disease, other organs, connective tissues, etc., and/or in context to one another, of one or more (e.g., tumor draining lymphatics or vasculature; or tumor proximity to organ capsule or underlying other organ), as unlimited examples.

Systems may be configured to include onboard integrated imaging hardware, software, sensors, probes and wetware, and/or may be configured to communicate and interface with external imaging and image processing systems. The afore-mentioned components may be also integrated into the system's Therapy sub-system components wherein probes, imaging arrays, or the like, and electrically, mechanically or electromechanically integrated into therapy transducers. This may afford, in part, the ability to have geometrically aligned imaging and therapy, with the therapy directly within the field of view, and in some cases in line, with imaging. In some embodiments, this integration may com-prise a fixed orientation of the imaging capability (e.g., imaging probe) in context to the therapy transducer. In other embodiments, the imaging solution may be able to move or adjust its position, including modifying angle, extension (e.g., distance from therapy transducer or patient), rotation (e.g., imaging plane in example of an ultrasound probe) and/or other parameters, including moving/adjusting dynamically while actively imaging. The imaging compo-nent or probe may be encoded so its orientation and position relative to another aspect of the system, such as the therapy transducer, and/or robotically-enabled positioning compo-nent may be determined.

In one embodiment, the system may comprise onboard ultrasound, further configured to allow users to visualize, monitor and receive feedback for procedure sites through the system displays and software, including allowing ultrasound imaging and characterization (and various forms of), ultra-sound guided planning and ultrasound guided treatment, all in real-time. The system may be configured to allow users to manually, semi-automated or in fully automated means image the patient (e.g., by hand or using a robotically-enabled imager).

In some embodiments, imaging feedback and monitoring can include monitoring changes in: backscatter from bubble clouds; speckle reduction in backscatter; backscatter speckle statistics; mechanical properties of tissue (i.e., elastogra-phy); tissue perfusion (i.e., ultrasound contrast); shear wave propagation; acoustic emissions, electrical impedance tomography, and/or various combinations of, including as displayed or integrated with other forms of imaging (e.g., CT or MRI).

In some embodiments, imaging including feedback and monitoring from backscatter from bubble clouds, may be used as a method to determine immediately if the histotripsy process has been initiated, is being properly maintained, or even if it has been extinguished. For example, this method enables continuously monitored in real time drug delivery, tissue erosion, and the like. The method also can provide feedback permitting the histotripsy process to be initiated at a higher intensity and maintained at a much lower intensity. For example, backscatter feedback can be monitored by any transducer or ultrasonic imager. By measuring feedback for the therapy transducer, an accessory transducer can send out interrogation pulses or be configured to passively detect cavitation. Moreover, the nature of the feedback received can be used to adjust acoustic parameters (and associated system parameters) to optimize the drug delivery and/or tissue erosion process.

In some embodiments, imaging including feedback and monitoring from backscatter, and speckle reduction, may be configured in the system.

For systems comprising feedback and monitoring via backscattering, and as means of background, as tissue is progressively mechanically subdivided, in other words homogenized, disrupted, or eroded tissue, this process results in changes in the size and distribution of acoustic scatter. At some point in the process, the scattering particle size and density is reduced to levels where little ultrasound is scattered, or the amount scattered is reduced significantly. This results in a significant reduction in speckle, which is the coherent constructive and destructive interference patterns of light and dark spots seen on images when coherent sources of illumination are used; in this case, ultrasound. After some treatment time, the speckle reduction results in a dark area in the therapy volume. Since the amount of speckle reduction is related to the amount of tissue subdi-vision, it can be related to the size of the remaining tissue fragments. When this size is reduced to sub-cellular levels, no cells are assumed to have survived. So, treatment can proceed until a desired speckle reduction level has been reached. Speckle is easily seen and evaluated on standard ultrasound imaging systems. Specialized transducers and systems, including those disclosed herein, may also be used to evaluate the backscatter changes.

Further, systems comprising feedback and monitoring via speckle, and as means of background, an image may persist from frame to frame and change very little as long as the scatter distribution does not change and there is no move-ment of the imaged object. However, long before the scatters are reduced enough in size to cause speckle reduction, they may be changed sufficiently to be detected by signal pro-cessing and other means. This family of techniques can operate as detectors of speckle statistics changes. For example, the size and position of one or more speckles in an image will begin to decorrelate before observable speckle reduction occurs. Speckle decorrelation, after appropriate motion compensation, can be a sensitive measure of the mechanical disruption of the tissues, and thus a measure of therapeutic efficacy. This feedback and monitoring tech-nique may permit early observation of changes resulting from the acoustic cavitation/histotripsy process and can identify changes in tissue before substantial or complete tissue effect (e.g., erosion occurs). In one embodiment, this method may be used to monitor the acoustic cavitation/histotripsy process for enhanced drug delivery where treat-ment sites/tissue is temporally disrupted, and tissue damage/erosion is not desired. In other embodiments, this may comprise speckle decorrelation by movement of scatters in an increasingly fluidized therapy volume. For example, in the case where partial or complete tissue erosion is desired.

For systems comprising feedback and monitoring via elastography, and as means of background, as treatment sites/tissue are further subdivided per an acoustic cavitation/histotripsy effect (homogenized, disrupted, or eroded), its mechanical properties change from a soft but interconnected solid to a viscous fluid or paste with few long-range inter-actions. These changes in mechanical properties can be measured by various imaging modalities including MRI and ultrasound imaging systems. For example, an ultrasound pulse can be used to produce a force (i.e., a radiation force) on a localized volume of tissue. The tissue response (dis-placements, strains, and velocities) can change significantly during histotripsy treatment allowing the state of tissue disruption to be determined by imaging or other quantitative means.

Systems may also comprise feedback and monitoring via shear wave propagation changes. As means of background, the subdivision of tissues makes the tissue more fluid and less solid and fluid systems generally do not propagate shear waves. Thus, the extent of tissue fluidization provides opportunities for feedback and monitoring of the histotripsy process. For example, ultrasound and MRI imaging systems can be used to observe the propagation of shear waves. The extinction of such waves in a treated volume is used as a measure of tissue destruction or disruption. In one system embodiment, the system and supporting sub-systems may be used to generate and measure the interacting shear waves. For example, two adjacent ultrasound foci might perturb tissue by pushing it in certain ways. If adjacent foci are in a fluid, no shear waves propagate to interact with each other. If the tissue is not fluidized, the interaction would be detected with external means, for example, by a difference frequency only detected when two shear waves interact nonlinearly, with their disappearance correlated to tissue damage. As such, the system may be configured to use this modality to enhance feedback and monitoring of the acoustic cavitation/histotripsy procedure.

For systems comprising feedback and monitoring via acoustic emission, and as means of background, as a tissue volume is subdivided, its effect on acoustic cavitation/histotripsy (e.g., the bubble cloud here) is changed. For example, bubbles may grow larger and have a different lifetime and collapse changing characteristics in intact versus fluidized tissue. Bubbles may also move and interact after tissue is subdivided producing larger bubbles or cooperative interaction among bubbles, all of which can result in changes in acoustic emission. These emissions can be heard during treatment and they change during treatment. Analysis of these changes, and their correlation to therapeutic efficacy, enables monitoring of the progress of therapy, and may be configured as a feature of the system.

For systems comprising feedback and monitoring via electrical impedance tomography, and as means of background, an impedance map of a therapy site can be produced based upon the spatial electrical characteristics throughout the therapy site. Imaging of the conductivity or permittivity of the therapy site of a patient can be inferred from taking skin surface electrical measurements. Conducting electrodes are attached to a patient's skin and small alternating currents are applied to some or all of the electrodes. One or more known currents are injected into the surface and the voltage is measured at a number of points using the electrodes. The process can be repeated for different configurations of applied current. The resolution of the resultant image can be adjusted by changing the number of electrodes employed. A measure of the electrical properties of the therapy site within the skin surface can be obtained from the impedance map, and changes in and location of the acoustic cavitation/histotripsy (e.g., bubble cloud, specifically) and histotripsy process can be monitored using this as configured in the system and supporting sub-systems.

The user may be allowed to further select, annotate, mark, highlight, and/or contour, various regions of interest or treatment sites, and defined treatment targets (on the image(s)), of which may be used to command and direct the system where to image, test and/or treat, through the system software and user interfaces and displays. In some arrangements, the user may use a manual ultrasound probe (e.g., diagnostic hand-held probe) to conduct the procedure. In another arrangement, the system may use a robot and/or electromechanical positioning system to conduct the procedure, as directed and/or automated by the system, or conversely, the system can enable combinations of manual and automated uses.

The system may further include the ability to conduct image registration, including imaging and image data set registration to allow navigation and localization of the system to the patient, including the treatment site (e.g., tumor, critical structure, bony anatomy, anatomy and identifying features of, etc.). In one embodiment, the system allows the user to image and identify a region of interest, for example the liver, using integrated ultrasound, and to select and mark a tumor (or surrogate marker of) comprised within the liver through/displayed in the system software, and wherein said system registers the image data to a coordinate system defined by the system, that further allows the system's Therapy and Robotics sub-systems to deliver synchronized acoustic cavitation/histotripsy to said marked tumor. The system may comprise the ability to register various image sets, including those previously disclosed, to one another, as well as to afford navigation and localization (e.g., of a therapy transducer to a CT or MRI/ultrasound fusion image with the therapy transducer and Robotics sub-system tracking to said image).

The system may also comprise the ability to work in a variety of interventional, endoscopic and surgical environments, including alone and with other systems (surgical/laparoscopic towers, vision systems, endoscope systems and towers, ultrasound enabled endoscopic ultrasound (flexible and rigid), percutaneous/endoscopic/laparoscopic and minimally invasive navigation systems (e.g., optical, electromagnetic, shape-sensing, ultrasound-enabled, etc.), of also which may work with, or comprise various optical imaging capabilities (e.g., fiber and or digital). The disclosed system may be configured to work with these systems, in some embodiments working alongside them in concert, or in other embodiments where all or some of the system may be integrated into the above systems/platforms (e.g., acoustic cavitation/histotripsy-enabled endoscope system or laparoscopic surgical robot). In many of these environments, a therapy transducer may be utilized at or around the time of use, for example, of an optically guided endoscope/bronchoscope, or as another example, at the time a laparoscopic robot (e.g., Intuitive Da Vinci* Xi system) is viewing/manipulating a tissue/treatment site. Further, these embodiments and examples may include where said other systems/platforms are used to deliver (locally) fluid to enable the creation of a man-made acoustic window, where on under normal circumstances may not exist (e.g., fluidizing a segment or lobe of the lung in preparation for acoustic cavitation/histotripsy via non-invasive transthoracic treatment (e.g., transducer externally placed on/around patient). Systems disclosed herein may also comprise all or some of their sub-system hardware packaged within the other system cart/console/systems described here (e.g., acoustic cavitation/histotripsy system and/or sub-systems integrated and operated from said navigation or laparoscopic system).

The system may also be configured, through various aforementioned parameters and other parameters, to display real-time visualization of a bubble cloud in a spatial-temporal manner, including the resulting tissue effect peri/post-treatment from tissue/bubble cloud interaction, wherein the system can dynamically image and visualize, and display, the bubble cloud, and any changes to it (e.g., decreasing or increasing echogenicity), which may include intensity, shape, size, location, morphology, persistence, etc. These features may allow users to continuously track and follow the treatment in real-time in one integrated procedure and interface/system, and confirm treatment safety and efficacy on the fly (versus other interventional or surgical modalities, which either require multiple procedures to achieve the same, or where the treatment effect is not visible in real-time (e.g., radiation therapy), or where it is not possible to achieve such (e.g., real-time visualization of local tissue during thermal ablation), and/or where the other procedure further require invasive approaches (e.g., incisions or punctures) and iterative imaging in a scanner between procedure steps (e.g., CT or MRI scanning). The above disclosed systems, sub-systems, components, modalities, features and work-flows/methods of use may be implemented in an unlimited fashion through enabling hardware, software, user interfaces and use environments, and future improvements, enhancements and inventions in this area are considered as included in the scope of this disclosure, as well as any of the resulting data and means of using said data for analytics, artificial intelligence or digital health applications and systems.

Robotics

They system may comprise various Robotic sub-systems and components, including but not limited to, one or more robotic arms and controllers, which may further work with other sub-systems or components of the system to deliver and monitor acoustic cavitation/histotripsy. As previously discussed herein, robotic arms and control systems may be integrated into one or more Cart configurations.

For example, one system embodiment may comprise a Cart with an integrated robotic arm and control system, and Therapy, Integrated Imaging and Software, where the robotic arm and other listed sub-systems are controlled by the user through the form factor of a single bedside Cart.

In other embodiments, the Robotic sub-system may be configured in one or more separate Carts, that may be a driven in a master/slave configuration from a separate master or Cart, wherein the robotically-enabled Cart is positioned bed/patient-side, and the Master is at a distance from said Cart.

Disclosed robotic arms may be comprised of a plurality of joints, segments, and degrees of freedom and may also include various integrated sensor types and encoders, implemented for various use and safety features. Sensing technologies and data may comprise, as an example, vision, potentiometers, position/localization, kinematics, force, torque, speed, acceleration, dynamic loading, and/or others. In some cases, sensors may be used for users to direct robot commands (e.g., hand gesture the robot into a preferred set up position, or to dock home). Additional details on robotic arms can be found in US Patent Pub. No. 2013/0255426 to Kassow et al. which is disclosed herein by reference in its entirety.

The robotic arm receives control signals and commands from the robotic control system, which may be housed in a Cart. The system may be configured to provide various functionalities, including but not limited to, position, tracking, patterns, triggering, and events/actions.

Position may be configured to comprise fixed positions, pallet positions, time-controlled positions, distance-controlled positions, variable-time controlled positions, variable-distance controlled positions.

Tracking may be configured to comprise time-controlled tracking and/or distance-controlled tracking.

The patterns of movement may be configured to comprise intermediate positions or waypoints, as well as sequence of positions, through a defined path in space.

Triggers may be configured to comprise distance measuring means, time, and/or various sensor means including those disclosed herein, and not limited to, visual/imaging-based, force, torque, localization, energy/power feedback and/or others.

Events/actions may be configured to comprise various examples, including proximity-based (approaching/departing a target object), activation or de-activation of various end-effectors (e.g., therapy transducers), starting/stopping/pausing sequences of said events, triggering or switching between triggers of events/actions, initiating patterns of movement and changing/toggling between patterns of movement, and/or time-based and temporal over the defined work and time-space.

In one embodiment, the system comprises a three degree of freedom robotic positioning system, enabled to allow the user (through the software of the system and related user interfaces), to micro-position a therapy transducer through X, Y, and Z coordinate system, and where gross macro-positioning of the transducer (e.g., aligning the transducer on the patient's body) is completed manually. In some embodiments, the robot may comprise 6 degrees of freedom including X, Y, Z, and pitch, roll and yaw. In other embodiments, the Robotic sub-system may comprise further degrees of freedom, that allow the robot arm supporting base to be positioned along a linear axis running parallel to the general direction of the patient surface, and/or the supporting base height to be adjusted up or down, allowing the position of the robotic arm to be modified relative to the patient, patient surface, Cart, Coupling sub-system, additional robots/robotic arms and/or additional surgical systems, including but not limited to, surgical towers, imaging systems, endoscopic/laparoscopic systems, and/or other.

One or more robotic arms may also comprise various features to assist in maneuvering and modifying the arm position, manually or semi-manually, and of which said features may interface on or between the therapy transducer and the most distal joint of the robotic arm. In some embodiments, the feature is configured to comprise a handle allowing maneuvering and manual control with one or more hands. The handle may also be configured to include user input and electronic control features of the robotic arm, to command various drive capabilities or modes, to actuate the robot to assist in gross or fine positioning of the arm (e.g., activating or deactivating free drive mode). The work-flow for the initial positioning of the robotic arm and therapy head can be configured to allow either first positioning the therapy transducer/head in the coupling solution, with the therapy transducer directly interfaced to the arm, or in a different work-flow, allowing the user to set up the coupling solution first, and enabling the robot arm to be interfaced to the therapy transducer/coupling solution as a later/terminal set up step.

In some embodiments, the one or more robotic arms or other features of the robotic sub-systems may include sensors or other features configured to measure, determine, or predict the force(s) acting against the robotic arm(s) and/or the therapy transducer array coupled to the robotic arm(s). These sensors can include force sensors or force transducers not limited to load cells, pneumatic load cells, capacitive load cells, strain gauge load cells, hydraulic load cells, etc. In some implementations, the force sensors can be disposed on or in the robotic arm(s), on or in the transducer array or therapy probe, on or in the coupling linkages between the transducer array and robotic arm, or in any other location within the system, including the robotics sub-system, where a force sensor or sensors would be adapted and configured to measure the force applied against the robotic arm or the transducer array. Additionally, these force sensors can be electronically or operatively coupled to any of the control systems described herein, including electronic controllers, robotic positioning systems, navigation systems, or any other cpus, processors, or controllers configured to control the operation of the transducer array, robotics sub-system, or any other sub-system during therapy.

In some embodiments, the robotic arm may comprise a robotic arm on a laparoscopic, single port, endoscopic, hybrid or combination of, and/or other robot, wherein said robot of the system may be a slave to a master that controls said arm, as well as potentially a plurality of other arms, equipped to concurrently execute other tasks (vision, imaging, grasping, cutting, ligating, sealing, closing, stapling, ablating, suturing, marking, etc.), including actuating one or more laparoscopic arms (and instruments) and various histotripsy system components. For example, a laparoscopic robot may be utilized to prepare the surgical site, including manipulating organ position to provide more ideal acoustic access and further stabilizing said organ in some cases to minimize respiratory motion. In conjunction and parallel to this, a second robotic arm may be used to deliver non-invasive acoustic cavitation through a body cavity, as observed under real-time imaging from the therapy transducer (e.g., ultrasound) and with concurrent visualization via a laparoscopic camera. In other related aspects, a similar approach may be utilized with a combination of an endoscopic and non-invasive approach, and further, with a combination of an endoscopic, laparoscopic and non-invasive approach.

Software

The system may comprise various software applications, features and components which allow the user to interact, control and use the system for a plethora of clinical applications. The Software may communicate and work with one or more of the sub-systems, including but not limited to Therapy, Integrated Imaging, Robotics and Other Components, Ancillaries and Accessories of the system.

Overall, in no specific order of importance, the software may provide features and support to initialize and set up the system, service the system, communicate and import/export/store data, modify/manipulate/configure/control/command various settings and parameters by the user, mitigate safety and use-related risks, plan procedures, provide support to various configurations of transducers, robotic arms and drive systems, function generators and amplifier circuits/slaves, test and treatment ultrasound sequences, transducer steering and positioning (electromechanical and electronic beam steering, etc.), treatment patterns, support for imaging and imaging probes, manual and electromechanical/robotically-enabling movement of, imaging support for measuring/characterizing various dimensions within or around procedure and treatment sites (e.g., depth from one anatomical location to another, etc., pre-treatment assessments and protocols for measuring/characterizing in situ treatment site properties and conditions (e.g., acoustic cavitation/histotripsy thresholds and heterogeneity of), targeting and target alignment, calibration, marking/annotating, localizing/navigating, registering, guiding, providing and guiding through work-flows, procedure steps, executing treatment plans and protocols autonomously, autonomously and while under direct observation and viewing with real-time imaging as displayed through the software, including various views and viewports for viewing, communication tools (video, audio, sharing, etc.), troubleshooting, providing directions, warnings, alerts, and/or allowing communication through various networking devices and protocols. It is further envisioned that the software user interfaces and supporting displays may comprise various buttons, commands, icons, graphics, text, etc., that allow the user to interact with the system in a user-friendly and effective manner, and these may be presented in an unlimited number of permutations, layouts and designs, and displayed in similar or different manners or feature sets for systems that may comprise more than one display (e.g., touch screen monitor and touch pad), and/or may network to one or more external displays or systems (e.g., another robot, navigation system, system tower, console, monitor, touch display, mobile device, tablet, etc.).

The software, as a part of a representative system, including one or more computer processors, may support the various aforementioned function generators (e.g., FPGA), amplifiers, power supplies and therapy transducers. The software may be configured to allow users to select, determine and monitor various parameters and settings for acoustic cavitation/histotripsy, and upon observing/receiving feedback on performance and conditions, may allow the user to stop/start/modify said parameters and settings.

The software may be configured to allow users to select from a list or menu of multiple transducers and support the auto-detection of said transducers upon connection to the system (and verification of the appropriate sequence and parameter settings based on selected application). In other embodiments, the software may update the targeting and amplifier settings (e.g., channels) based on the specific transducer selection. The software may also provide transducer recommendations based on pre-treatment and planning inputs. Conversely, the software may provide error messages or warnings to the user if said therapy transducer, amplifier and/or function generator selections or parameters are erroneous, yield a fault or failure. This may further comprise reporting the details and location of such.

In addition to above, the software may be configured to allow users to select treatment sequences and protocols from a list or menu, and to store selected and/or previous selected sequences and protocols as associated with specific clinical uses or patient profiles. Related profiles may comprise any associated patient, procedure, clinical and/or engineering data, and maybe used to inform, modify and/or guide current or future treatments or procedures/interventions, whether as decision support or an active part of a procedure itself (e.g., using serial data sets to build and guide new treatments).

As a part of planning or during the treatment, the software (and in working with other components of the system) may allow the user to evaluate and test acoustic cavitation/histotripsy thresholds at various locations in a user-selected region of interest or defined treatment area/volume, to determine the minimum cavitation thresholds throughout said region or area/volume, to ensure treatment parameters are optimized to achieve, maintain and dynamically control acoustic cavitation/histotripsy. In one embodiment, the system allows a user to manually evaluate and test threshold parameters at various points. Said points may include those at defined boundary, interior to the boundary and center locations/positions, of the selected region of interest and treatment area/volume, and where resulting threshold measurements may be reported/displayed to the user, as well as utilized to update therapy parameters before treatment. In another embodiment, the system may be configured to allow automated threshold measurements and updates, as enabled by the aforementioned Robotics sub-system, wherein the user may direct the robot, or the robot may be commanded to execute the measurements autonomously.

Software may also be configured, by working with computer processors and one or more function generators, amplifiers and therapy transducers, to allow various permutations of delivering and positioning optimized acoustic cavitation/histotripsy in and through a selected area/volume. This may include, but not limited to, systems configured with a fixed/natural focus arrangement using purely electromechanical positioning configuration(s), electronic beam steering (with or without electromechanical positioning), electronic beam steering to a new selected fixed focus with further electromechanical positioning, axial (Z axis) electronic beam steering with lateral (X and Y) electromechanical positioning, high speed axial electronic beam steering with lateral electromechanical positioning, high speed beam steering in 3D space, various combinations of including with dynamically varying one or more acoustic cavitation/histotripsy parameters based on the aforementioned ability to update treatment parameters based on threshold measurements (e.g., dynamically adjusting amplitude across the treatment area/volume).

Other Components, Ancillaries and Accessories

The system may comprise various other components, ancillaries and accessories, including but not limited to computers, computer processors, power supplies including high voltage power supplies, controllers, cables, connectors, networking devices, software applications for security, communication, integration into information systems including hospital information systems, cellular communication devices and modems, handheld wired or wireless controllers, goggles or glasses for advanced visualization, augmented or virtual reality applications, cameras, sensors, tablets, smart devices, phones, internet of things enabling capabilities, specialized use "apps" or user training materials and applications (software or paper based), virtual proctors or trainers and/or other enabling features, devices, systems or applications, and/or methods of using the above.

System Variations and Methods/Applications

In addition to performing a breadth of procedures, the system may allow additional benefits, such as enhanced planning, imaging and guidance to assist the user. In one embodiment, the system may allow a user to create a patient, target and application specific treatment plan, wherein the system may be configured to optimize treatment parameters based on feedback to the system during planning, and where planning may further comprise the ability to run various test protocols to gather specific inputs to the system and plan.

Feedback may include various energy, power, location, position, tissue and/or other parameters.

The system, and the above feedback, may also be further configured and used to autonomously (and robotically) execute the delivery of the optimized treatment plan and protocol, as visualized under real-time imaging during the procedure, allowing the user to directly observe the local treatment tissue effect, as it progresses through treatment, and start/stop/modify treatment at their discretion. Both test and treatment protocols may be updated over the course of the procedure at the direction of the user, or in some embodiments, based on logic embedded within the system.

It is also recognized that many of these benefits may further improve other forms of acoustic therapy, including thermal ablation with high intensity focused ultrasound (HIFU), high intensity therapeutic ultrasound (HITU) including boiling histotripsy (thermal cavitation), and are considered as part of this disclosure. The disclosure also considers the application of histotripsy as a means to activate previously delivered in active drug payloads whose activity is inert due to protection in a micelle, nanostructure or similar protective structure or through molecular arrangement that allows activation only when struck with acoustic energy.

In another aspect, the Therapy sub-system, comprising in part, one or more amplifiers, transducers and power supplies, may be configured to allow multiple acoustic cavitation and histotripsy driving capabilities, affording specific benefits based on application, method and/or patient specific use. These benefits may include, but are not limited to, the ability to better optimize and control treatment parameters, which may allow delivery of more energy, with more desirable thermal profiles, increased treatment speed and reduced procedure times, enable electronic beam steering and/or other features.

This disclosure also includes novel systems and concepts as related to systems and sub-systems comprising new and "universal" amplifiers, which may allow multiple driving approaches (e.g., single and multi-cycle pulsing). In some embodiments, this may include various novel features to further protect the system and user, in terms of electrical safety or other hazards (e.g., damage to transducer and/or amplifier circuitry).

In another aspect, the system, and Therapy sub-system, may include a plethora of therapy transducers, where said therapy transducers are configured for specific applications and uses and may accommodate treating over a wide range of working parameters (target size, depth, location, etc.) and may comprise a wide range of working specifications (detailed below). Transducers may further adapt, interface and connect to a robotically-enabled system, as well as the Coupling sub-system, allowing the transducer to be positioned within, or along with, an acoustic coupling device allowing, in many embodiments, concurrent imaging and histotripsy treatments through an acceptable acoustic window. The therapy transducer may also comprise an integrated imaging probe or localization sensors, capable of displaying and determining transducer position within the treatment site and affording a direct field of view (or representation of) the treatment site, and as the acoustic cavitation/histotripsy tissue effect and bubble cloud may or may not change in appearance and intensity, throughout the treatment, and as a function of its location within said treatment (e.g., tumor, healthy tissue surrounding, critical structures, adipose tissue, etc.).

The systems, methods and use of the system disclosed herein, may be beneficial to overcoming significant unmet needs in the areas of soft tissue ablation, oncology, immuno-oncology, advanced image guided procedures, surgical procedures including but not limited to open, laparoscopic, single incision, natural orifice, endoscopic, non-invasive, various combination of, various interventional spaces for catheter-based procedures of the vascular, cardiovascular pulmonary and/or neurocranial-related spaces, cosmetics/aesthetics, metabolic (e.g., type 2 diabetes), plastic and reconstructive, ocular and ophthalmology, orthopedic, gynecology and men's health, and other systems, devices and methods of treating diseased, injured, undesired, or healthy tissues, organs or cells.

Systems and methods are also provided for improving treatment patterns within tissue that can reduce treatment time, improve efficacy, and reduce the amount of energy and prefocal tissue heating delivered to patients.

Use Environments

The disclosed system, methods of use, and use of the system, may be conducted in a plethora of environments and settings, with or without various support systems such as anesthesia, including but not limited to, procedure suites, operating rooms, hybrid rooms, in and out-patient settings, ambulatory settings, imaging centers, radiology, radiation therapy, oncology, surgical and/or any medical center, as well as physician offices, mobile healthcare centers or systems, automobiles and related vehicles (e.g., van), aero and marine transportation vehicles such as planes and ships, and/or any structure capable of providing temporary procedure support (e.g., tent). In some cases, systems and/or sub-systems disclosed herein may also be provided as integrated features into other environments, for example, the direct integration of the histotripsy Therapy sub-system into a MRI scanner or patient surface/bed, wherein at a minimum the therapy generator and transducer are integral to such, and in other cases wherein the histotripsy configuration further includes a robotic positioning system, which also may be integral to a scanner or bed centered design.

Coupling

Systems may comprise a variety of Coupling sub-system embodiments, of which are enabled and configured to allow acoustic coupling to the patient to afford effective acoustic access for ultrasound visualization and acoustic cavitation/histotripsy (e.g., provide acoustic window and medium between the transducer(s) and patient, and support of). These may include different form factors of such, including open and enclosed device solutions, and some arrangements which may be configured to allow dynamic control over the acoustic medium (e.g., temperature, dissolved gas content, level of particulate filtration, sterility, volume, composition, etc.). Such dynamic control components may be directly integrated to the system (within the Cart), or may be in temporary/intermittent or continuous communication with the system, but externally situated in a separate device and/or cart.

The Coupling sub-system typically comprises, at a minimum, coupling medium (e.g., degassed water or water solutions), a reservoir/container to contain said coupling medium, and a support structure (including interfaces to other surfaces or devices). In most embodiments, the coupling medium is water, and wherein the water may be conditioned before or during the procedure (e.g., chilled, degassed, filtered, etc.). Various conditioning parameters may be employed based on the configuration of the system and its intended use/application.

The reservoir or medium container may be formed and shaped to various sizes and shapes, and to adapt/conform to the patient, allow the therapy transducer to engage/access and work within the acoustic medium, per defined and required working space (minimum volume of medium to allow the therapy transducer to be positioned and/or move through one or more treatment positions or patterns, and at various standoffs or depths from the patient, etc.), and wherein said reservoir or medium container may also mechanically support the load, and distribution of the load, through the use of a mechanical and/or electromechanical support structure. As a representative example, this may include a support frame. The container may be of various shapes, sizes, curvatures, and dimensions, and may be comprised of a variety of materials compositions (single, multiple, composites, etc.), of which may vary throughout. In some embodiments, it may comprise features such as films, drapes, membranes, bellows, etc. that may be insertable and removable, and/or fabricated within, of which may be used to conform to the patient and assist in confining/containing the medium within the container. It may further contain various sensors (e.g., volume/fill level), drains (e.g., inlet/outlet), lighting (e.g., LEDs), markings (e.g., fill lines, set up orientations, etc.), text (e.g., labeling), etc.

In one embodiment, the reservoir or medium container contains a sealable frame, of which a membrane and/or film may be positioned within, to afford a conformable means of contacting the reservoir (later comprising the treatment head/therapy transducer) as an interface to the patient, that further provides a barrier to the medium (e.g., water) between the patient and therapy transducer). In other embodiments, the membrane and/or film may comprise an opening, the patient contacting edge of which affords a fluid/mechanical seal to the patient, but in contrast allows medium communication directly with the patient (e.g., direct degassed water interface with patient). The superstructure of the reservoir or medium container in both these examples may further afford the proximal portion of the structure (e.g., top) to be open or enclosed (e.g., to prevent spillage or afford additional features).

Disclosed membranes may be comprised of various elastomers, viscoelastic polymers, thermoplastics, thermoplastic elastomers, thermoset polymers, silicones, urethanes, rigid/flexible co-polymers, block co-polymers, random block co-polymers, etc. Materials may be hydrophilic, hydrophobic, surface modified, coated, extracted, etc., and may also contain various additives to enhance performance, appearance or stability. In some embodiments, the thermoplastic elastomer may be styrene-ethylene-butylene-styrene (SEBS), or other like strong and flexible elastomers. The membrane form factor can be flat or pre-shaped prior to use. In other embodiments, the membrane could be inelastic (i.e., a convex shape) and pressed against the patient's skin to acoustically couple the transducer to the tissue. Systems and methods are further disclosed to control the level of contaminants (e.g., particulates, etc.) on the membrane to maintain the proper level of ultrasound coupling. Too many particulates or contaminants can cause scattering of the ultrasound waves. This can be achieved with removable films or coatings on the outer surfaces of the membrane to protect against contamination.

Said materials may be formed into useful membranes through molding, casting, spraying, ultrasonic spraying, extruding, and/or any other processing methodology that produces useful embodiments. They may be single use or reposable/reusable. They may be provided non-sterile, aseptically cleaned or sterile, where sterilization may comprise any known method, including but not limited to ethylene oxide, gamma, e-beam, autoclaving, steam, peroxide, plasma, chemical, etc. Membranes can be further configured with an outer molded or over molded frame to provide mechanical stability to the membrane during handling including assembly, set up and take down of the coupling sub-system. Various parameters of the membrane can be optimized for this method of use, including thickness, thickness profile, density, formulation (e.g., polymer molecular weight and copolymer ratios, additives, plasticizers, etc.), including optimizing specifically to maximize acoustic transmission properties, including minimizing impact to cavitation initiation threshold values, and/or ultrasound imaging artifacts, including but not limited to membrane reflections, as representative examples.

Open reservoirs or medium containers may comprise various methods of filling, including using pre-prepared medium or water, that may be delivered into the containers, in some cases to a defined specification of water (level of temperature, gas saturation, etc.), or they may comprise additional features integral to the design that allow filling and draining (e.g., ports, valves, hoses, tubing, fittings, bags, pumps, etc.). These features may be further configured into or to interface to other devices, including for example, a fluidics system. In some cases, the fluidics system may be an in-house medium preparation system in a hospital or care setting room, or conversely, a mobile cart-based system which can prepare and transport medium to and from the cart to the medium container, etc.

Enclosed iterations of the reservoir or medium container may comprise various features for sealing, in some embodiments sealing to a proximal/top portion or structure of a reservoir/container, or in other cases where sealing may comprise embodiments that seal to the transducer, or a feature on the transducer housings. Further, some embodiments may comprise the dynamic ability to control the volume of fluid within these designs, to minimize the potential for air bubbles or turbulence in said fluid and to allow for changes in the focal length to the target area without moving the transducer. As such, integrated features allowing fluid communication, and control of, may be provided (ability to provide/remove fluid on demand), including the ability to monitor and control various fluid parameters, some disclosed above. In order to provide this functionality, the overall system, and as part, the Coupling sub-system, may comprise a fluid conditioning system, which may contain various electromechanical devices, systems, power, sensing, computing, pumping, filtering and control systems, etc. The reservoir may also be configured to receive signals that cause it to deform or change shape in a specific and controlled manner to allow the target point to be adjusted without moving the transducer.

Coupling support systems may include various mechanical support devices to interface the reservoir/container and medium to the patient, and the workspace (e.g., bed, floor, etc.). In some embodiments, the support system comprises a mechanical arm with 3 or more degrees of freedom. Said arm may have a proximal interface with one or more locations (and features) of the bed, including but not limited to, the frame, rails, customized rails or inserts, as well as one or more distal locations of the reservoir or container. The arm may also be a feature implemented on one or more Carts, wherein Carts may be configured in various unlimited permutations, in some cases where a Cart only comprises the role of supporting and providing the disclosed support structure.

In some embodiments, the support structure and arm may be a robotically-enabled arm, implemented as a stand-alone Cart, or integrated into a Cart further comprising two or more system sub-systems, or where in the robotically-enabled arm is an arm of another robot, of interventional, surgical or other type, and may further comprise various user input features to actuate/control the robotic arm (e.g., positioning into/within coupling medium) and/or Coupling solution features (e.g., filling, draining, etc.). In some examples, the support structure robotic arm positional encoders may be used to coordinate the manipulation of the second arm (e.g. comprising the therapy transducer/treatment head), such as to position the therapy transducer to a desired/known location and pose within the coupling support structure.

Overall, significant unmet needs exist in interventional and surgical medical procedures today, including those procedures utilizing minimally invasive devices and approaches to treat disease and/or injury, and across various types of procedures where the unmet needs may be solved with entirely new medical procedures. Today's medical system capabilities are often limited by access, wherein a less or non-invasive approach would be preferred, or wherein today's tools aren't capable to deliver preferred/required tissue effects (e.g., operate around/through critical structures without serious injury), or where the physical set up of the systems makes certain procedure approaches less desirable or not possible, and where a combination of approaches, along with enhanced tissue effecting treatments, may enable entirely new procedures and approaches, not possible today.

In addition, specific needs exist for enabling histotripsy delivery, including robotic histotripsy delivery, wherein one or more histotripsy therapy transducers may be configured to acoustically couple to a patient, using a completely sealed approach (e.g., no acoustic medium communication with the patient's skin) and allowing the one or more histotripsy transducers to be moved within the coupling solution without impeding the motion/movement of the robotic arm or interfering/disturbing the coupling interface, which could affect the intended treatment and/or target location.

Disclosed herein are histotripsy acoustic and patient coupling systems and methods, to enable histotripsy therapy/treatment, as envisioned in any setting, from interventional suite, operating room, hybrid suites, imaging centers, medical centers, office settings, mobile treatment centers, and/or others, as non-limiting examples. The following disclosure further describes novel systems used to create, control, maintain, modify/enhance, monitor and setup/takedown acoustic and patient coupling systems, in a variety of approaches, methods, environments, architectures and work-flows. In general, the disclosed novel systems may allow for a coupling medium, in some examples degassed water, to be interfaced between a histotripsy therapy transducer and a patient, wherein the acoustic medium provides sufficient acoustic coupling to said patient, allowing the delivery of histotripsy pulses through a user desired treatment location (and volume), where the delivery may require physically moving the histotripsy therapy transducer within a defined work-space comprising the coupling medium, and also where the coupling system is configured to allow said movement of the therapy transducer (and positioning system, e.g., robot) freely and unencumbered from by the coupling support system (e.g., a frame or manifold holding the coupling medium).

Coupling System and Sub-Systems/Components

Figure 2:
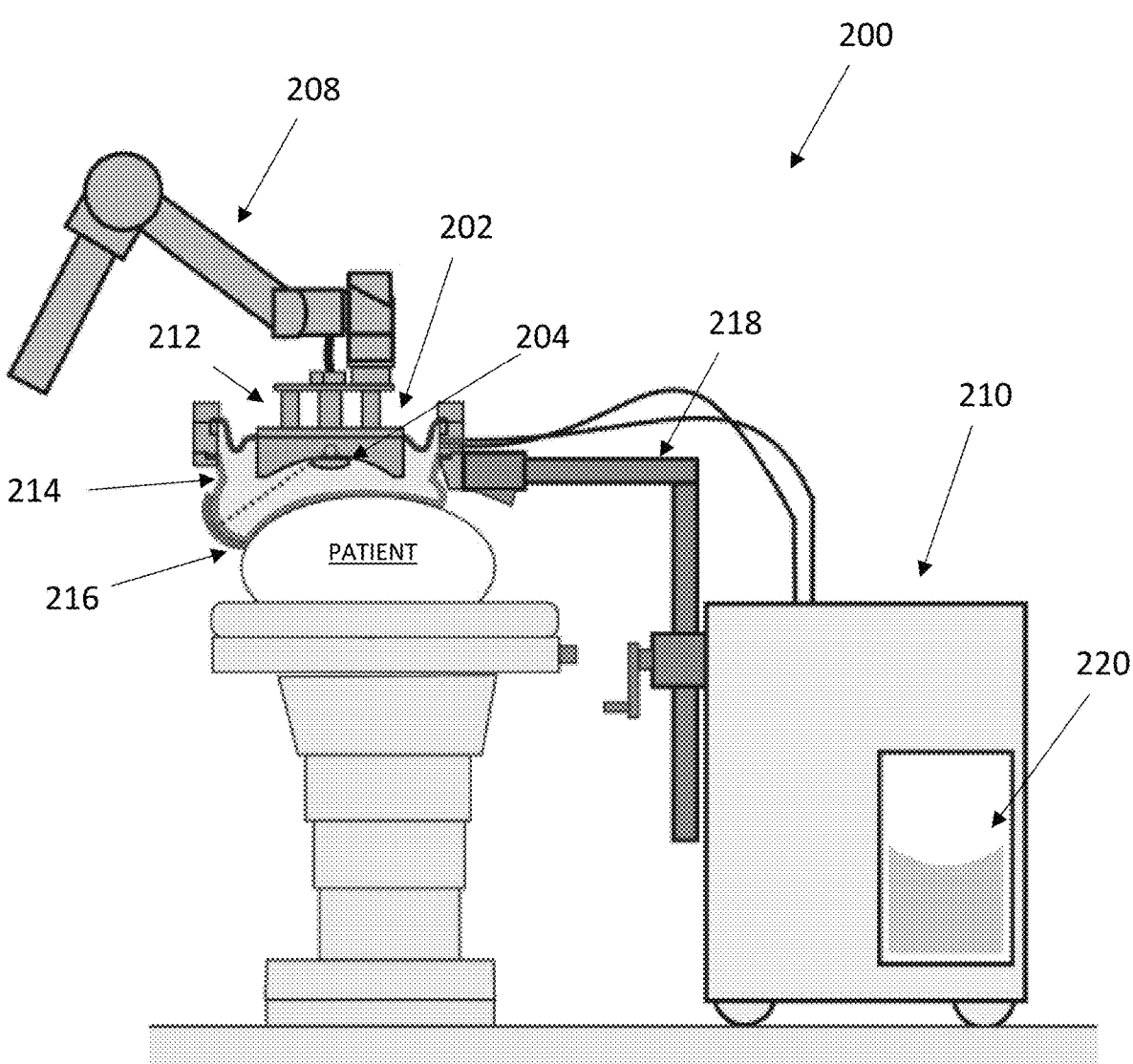
FIG. 2 is one embodiment of a histotripsy therapy and imaging system with a coupling system.

The disclosed histotripsy acoustic and patient coupling systems, in general, may comprise one or more of the following sub-systems and components, an example of which is depicted in FIG. 2, including but not limited to 1) a membrane/barrier film to provide an enclosed, sealed and conformal patient coupling and histotripsy system interface, 2) a frame and assembly to retain the membrane and provide sufficient work and head space for a histotripsy therapy transducers required range of motion (x, y and z, pitch, roll and yaw), 3) a sufficient volume of ultrasound medium to afford acoustic coupling and interfaces to a histotripsy therapy transducer and robotic arm, 4) one or more mechanical support arms to allow placement, positioning and load support of the frame, assembly and medium and 5) a fluidics system to prepare, provide and remove ultrasound medium (s) from the frame and assembly.

In some embodiments, the coupling system may be fully sealed, and in other embodiments and configurations, it may be partially open to afford immediate access (physical and/or visual).

The acoustic and patient coupling systems and sub-systems may further comprise various features and functionality, and associated work-flows, and may also be configured in a variety of ways to enable histotripsy procedures as detailed below.

FIG. 2 illustrates one embodiment of a histotripsy therapy and imaging system 200, including a coupling assembly 212. As described above, a histotripsy therapy and imaging system can include a therapy transducer 202, an imaging system 204, a robotic positioning arm 208, and a cart 210.

The therapy and/or imaging transducers can be housed in a coupling assembly 212 which can further include a coupling membrane 214 and a membrane constraint 216 configured to prevent the membrane from expanding too far from the transducer. The coupling membrane can be filled with an acoustic coupling medium such as a fluid or a gel. The membrane constraint can be, for example, a semi-rigid or rigid material configured to restrict expansion/movement of the membrane. In some embodiments, the membrane constraint is not used, and the elasticity and tensile strength of the membrane prevent over expansion. The coupling membrane can be a mineral-oil infused SEBS membrane to prevent direct fluid contact with the patient's skin. In the illustrated embodiment, the coupling assembly 212 is supported by a mechanical support arm 218 which can be load bearing in the x-y plane but allow for manual or automated z-axis adjustment. The mechanical support arm can be attached to the floor, the patient table, or the cart 210. The mechanical support is designed and configured to conform and hold the coupling membrane 214 in place against the patient's skin while still allowing movement of the therapy/imaging transducer relative to the patient and also relative to the coupling membrane 214 with the robotic positioning arm 208.

The system can further include a fluidics system 220 that can include a fluid source, a cooling and degassing system, and a programmable control system. The fluidics system is configured for external loading of the coupling membrane with automated control of fluidic sequences. Further details on the fluidics system 220 are provided below.

Membranes/Barrier Films and Related Architectures

Membranes and barrier films may be composed of various biocompatible materials which allow conformal coupling to patient anatomy with minimal or no entrapped bubbles capable of interfering with ultrasound imaging and histotripsy therapy, and that are capable of providing a sealed barrier layer between said patient anatomy and the ultrasound medium, of which is contained within the work-space provided by the frame and assembly.

Membrane and barrier film materials may comprise flexible and elastomeric biocompatible materials/polymers, such as various thermoplastic and thermoset materials, as well as permanent or bioresorbable polymers. Additionally, the frame of the UMC can also comprise the same materials. In some examples, the membrane may be rigid or semi-rigid polymers which are pre-shaped or flat.

Ultrasound Medium

As previously described, the ultrasound medium may comprise any applicable medium capable of providing sufficient and useful acoustic coupling to allow histotripsy treatments and enable sufficient clinical imaging (e.g., ultrasound). Ultrasound mediums, as a part of this disclosure and system, may comprise, but are not limited to, various aqueous solutions/mediums, including mixtures with other co-soluble fluids, of which may have preferred or more preferred acoustic qualities, including ability to match speed of sound, etc. Example mediums may comprise degassed water and/or mixtures/co-solutions of degassed water and various alcohols, such as ethanol.

Mechanical Support Arms and Arm Architectures

In order to support the acoustic and patient coupling system, including providing efficient and ergonomic workflows for users, various designs and configurations of mechanical support arms (and arm architectures) may be employed. Support arms may be configured with a range of degrees of freedom, including but not limited to allowing, x, y, z, pitch, roll and yaw, as well additional interfacing features that may allow additional height adjustment or translation.

Arms may comprise a varied number and type of joints and segments. Typically, arms may comprise a minimum of 2 segments. In some configurations, arms may comprise 3 to 5 segments.

Arms are also be configured to interface proximally to a main support base or base interface (e.g., robot, table, table/bed rail, cart, floor mount, etc.) and distally to the frame/assembly and overall "UMC" or "coupling solution". This specific distal interface may further include features for controlling position/orientation of the frame/assembly, at the frame/assembly interface.

For example, in some embodiments, the arm/frame interface may comprise a ball joint wrist. In another example, the interface may include use of a gimbal wrist or an adjustable pitch and roll controlled wrist. These interfaces may be further employed with specific user interfaces and inputs, to assist with interacting with the various wrists, of which may include additional handles or knobs (as an unlimited example), to further enable positioning the UMC/coupling solution. For example, a gimbal wrist may benefit from allowing the frame/assembly to have 3 degrees of freedom (independent of the arm degrees of freedom), including pitch, roll and yaw adjustments.

Support arms, configured with arm wrists, further interfaced with frames/assemblies, may comprise features such as brakes, including cable or electronic actuated brakes, and quick releases, which may interact with one or more axis, individually, or in groupings. They may also include electronic lift systems and base supports. In some embodiments, these lift systems/base supports are co-located with robot arm bases, wherein said robot arm is equipped with the histotripsy therapy transducer configured to fit/work within the enclosed coupling solution. In other embodiments, the support arm is located on a separate cart. In some cases, the separate cart may comprise a fluidics system or user console. In other embodiments, it is interfaced to a bed/table, including but not limited to a rail, side surface, and/or bed/table base. In other examples/embodiments, it's interfaced to a floor-based structure/footing, capable of managing weight and tipping requirements.

Fluidics Systems, Control Systems and System Architectures

As a part of overall fluidics management, histotripsy systems including acoustic/patient coupling systems, may be configured to include an automated fluidics system, which primarily is responsible for providing a reservoir for preparation and use of coupling medium, where preparation may include the ability to degas, chill, monitor, adjust, dispense/fill, and retrieve/drain coupling medium to/from the frame/assembly. The fluidics system may include an emergency high flow rate system for rapid draining of the coupling medium from the UMC. In some embodiments, the fluidics system can be configured for a single use of the coupling medium, or alternatively, for re-use of the medium. In some embodiments, the fluidics system can implement positive air pressure or vacuum to carry out leak tests of the UMC and membrane prior to filling with a coupling medium. Vacuum assist can also be used for removal of air from the UMC during the filling process. The fluidics system can further include filters configured to prevent particulate contamination from reaching the UMC.

The fluidics system may implemented in the form of a mobile fluidics cart. The cart may comprise an input tank, drain tank, degassing module, fill pump, drain pump, inert gas tank, air compressor, tubing/connectors/lines, electronic and manual controls systems and input devices, power supplies and one or more batteries. The cart in some cases may also comprise a system check vessel/reservoir for evaluating histotripsy system performance and related system diagnostics (configured to accommodate a required water volume and work-space for a therapy transducer).

Force Sensing and Calibration

As described above, the treatment head, comprising the therapy transducer, co-axially mounted ultrasound imaging probe, user input physical controls (robot and imaging probe), handles, and electromechanical interfaces/connections, can be coupled to a robotic arm and be configured to translate and move around within a fluid filled coupling assembly during a histotripsy procedure. In some embodiments, a treatment plan for a given target tissue volume may require movement of the treatment head to positions at or near the physical perimeter of the coupling assembly. Additionally, in some situations, the treatment plan may result in movement or translation of the treatment head that causes physical contact between the treatment head and the patient. This may include physical contact between the patient or one or more of the various system components (e.g., coupling container) and the treatment head. Furthermore, accidents in the operating room can occur including medical staff or professionals bumping into or contacting the robotic arm or treatment head during a procedure. In these scenarios, the system may implement systems and methods configured to sense or detect the amount of force acting upon the treatment head to alert the user and/or prevent excessive forces from being applied to the patient, the coupling assembly, or both.

As also described above, histotripsy procedures may comprise various work-flow steps wherein the ability to sense, detect and respond to various force scenarios is clinically important. Such work-flow steps may include system setup and system check, introducing the treatment head into the coupling assembly which contains coupling medium (e.g., degas sed water), accounting and allowing for buoyancy forces of said coupling medium, further targeting and localizing regions of interest and treatment targets (e.g., tumors or unwanted tissue), treatment planning, surveying said treatment plans with potential physical interactions with the coupling assembly and/or patient via robotically-enabled motion and movement through and around the plan(s), and during therapy delivery. In some embodiments, responses to measured forces, as well as how they are displayed to the user via system interfaces and displays, may vary by work-flow stage and associated risks to the patient, equipment and/or user.

First, to be able to accurately track the forces acting against the treatment head and robotic arm based on the environment, the system can include a dynamic calibration function to calibrate for buoyancy forces applied by the coupling medium or water bath against the treatment head and/or robot. The calibration function can be based on depth of submersion of the treatment head and pose (e.g., insertion angle) of treatment head within the coupling container. In some examples, the treatment head comprises a partially hollow or hollow treatment head which, when submerged into the coupling medium, can cause buoyancy forces to be detected up to 20 newtons. The magnitude of the buoyancy force depends on depth of submersion and area of the treatment head the upward forces are acting upon. Without accounting for the buoyancy forces acting against the system, the system cannot accurately know or measure the amount of relevant force acting against the treatment head and robot during the procedure (e.g., such as collision forces between the treatment head and the coupling assembly or patient).

In some aspects, a histotripsy system may include more than one treatment head that may be used depending on the size/location of the target tissue volume and other factors including size, shape, or anatomy of the patient. The appropriate treatment head may be chosen by a medical provider and quickly attached or swapped onto the robotic positioning arm. The various treatment heads may include different sizes or shapes (e.g., small, medium, large) and/or different transducer orientations, resulting in different buoyancy forces acting against a given treatment head. In some embodiments, the dynamic calibration function allows for calibration of a given treatment head, allowing a medical provider to swap or change treatment heads while still accounting for the correct buoyancy forces acting against the treatment head.

In one embodiment, the average buoyancy force for a given treatment head can be calculated or measured with repeated controlled submersions of the transducer array into the coupling container. In another embodiment, the buoyancy may be estimated or calculated based on a depth of insertion and pose angle of the treatment head within the coupling container. In some examples, the height can be input or set by the user, or automatically calculated or determined by the system. The pose angle is typically calculated automatically by the system based on the angle of the robotic positioning arm at the connection to the treatment head, but it is contemplated that this angle could also be set or input manually if desired. Once these inputs is known by the system, an algorithm to calculate buoyancy forces based on depth of submersion and/or pose angle can be applied. The buoyancy force which is calculated or estimated may be subtracted out from the overall force measurement of the robotic arm (e.g., forces acting against the treatment head) when performing/displaying force feedback.

Figure 3:
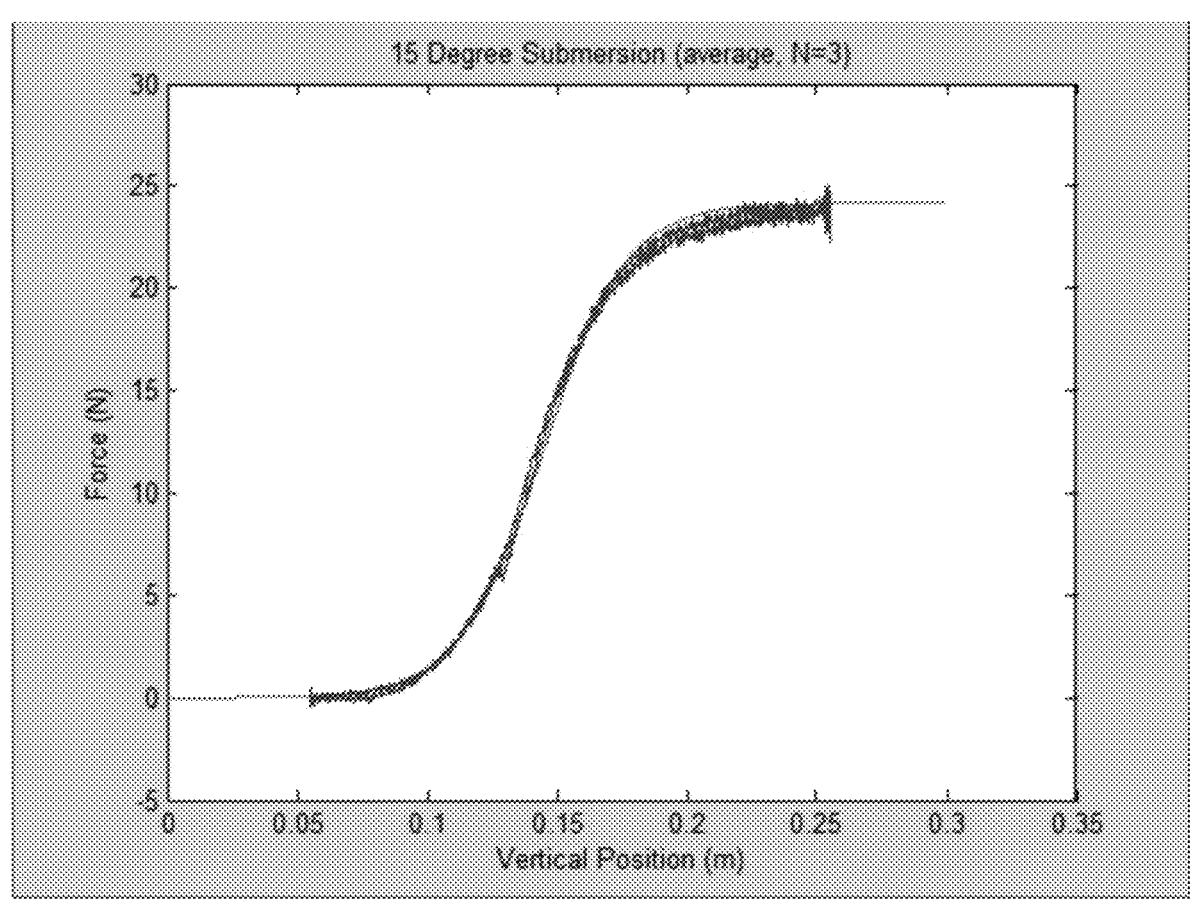
FIG. 3 is a chart that illustrates the force applied against a transducer array submerged in a coupling container or medium at a 15 degree submersion angle at various vertical positions from the surface of the medium.
Figure 4:
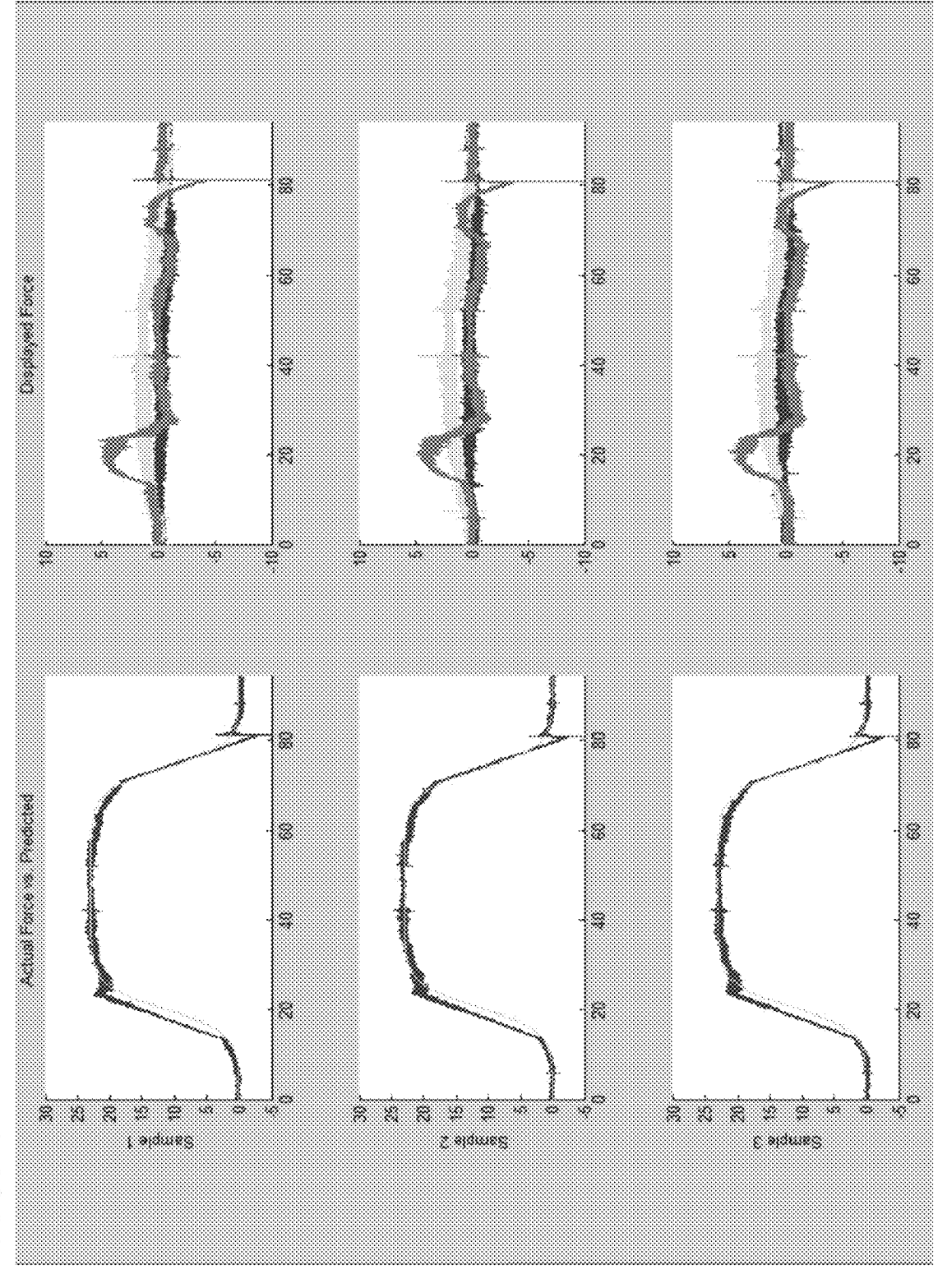
FIGS. 4-7 illustrate actual force vs. estimated/calculated force for a plurality of submersion pose angles.
Figure 5:
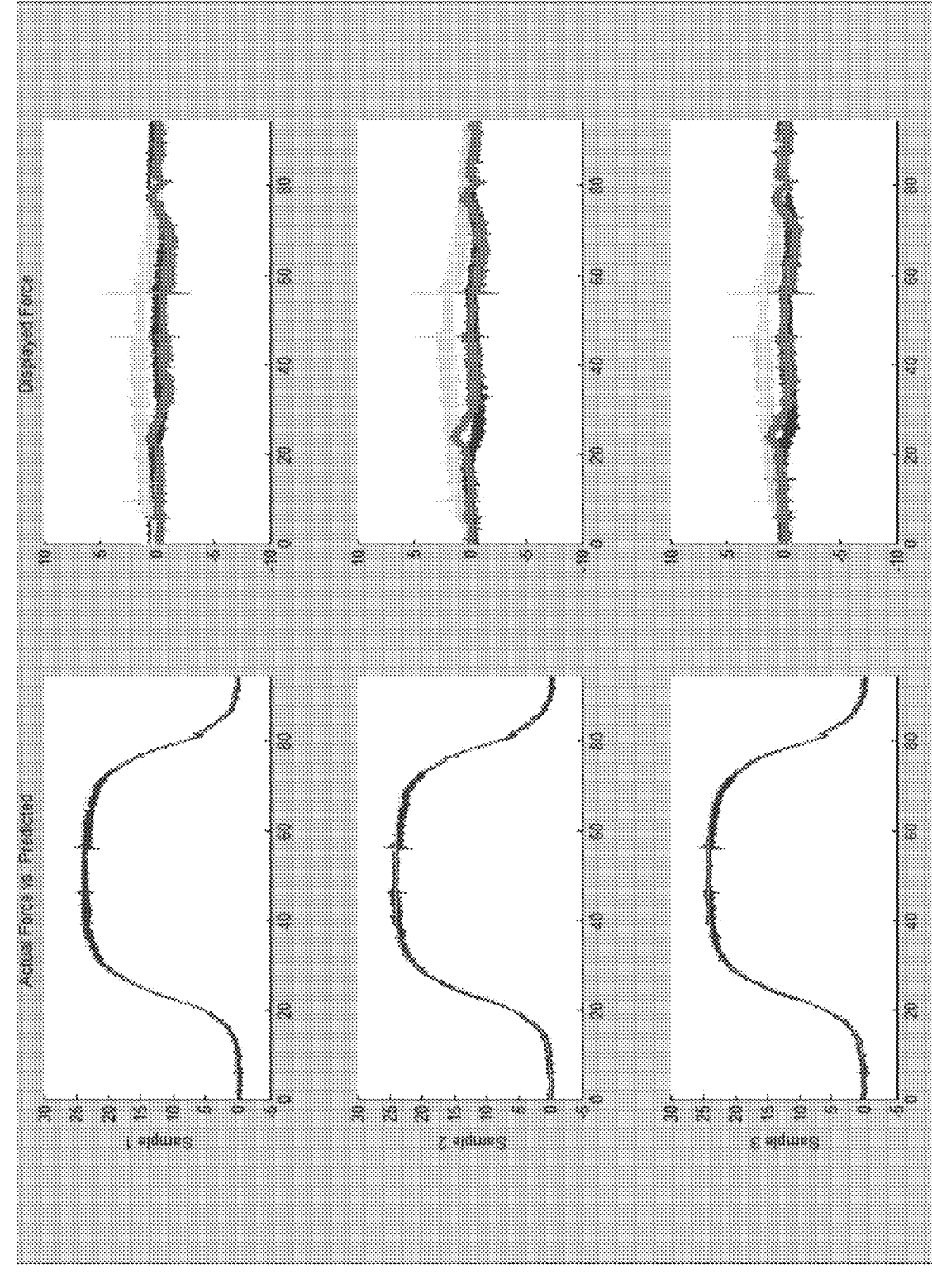
Figure 6:
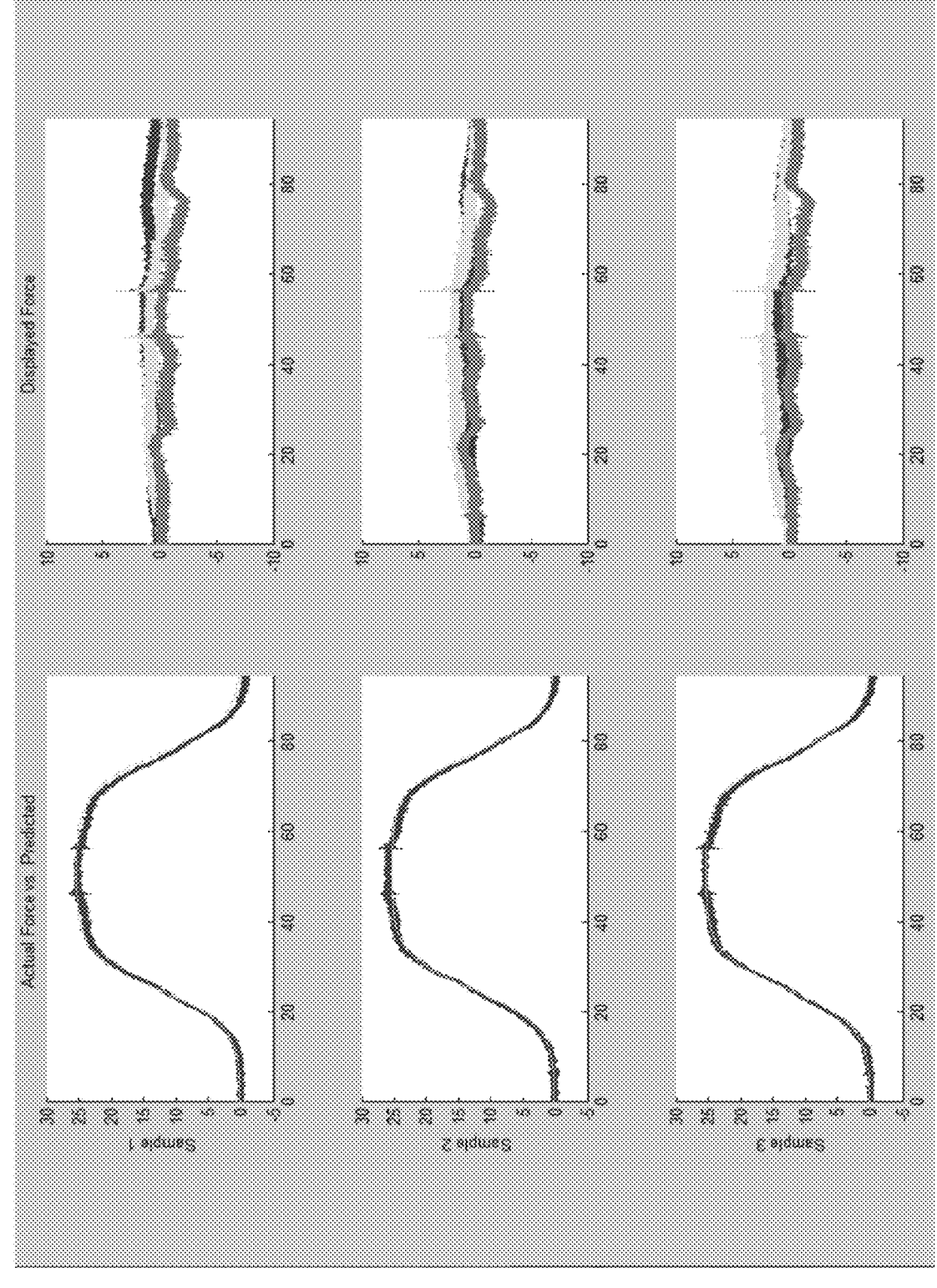

In one exemplary embodiment, FIG. 3 is a chart that illustrates the force applied against a transducer array submerged in a coupling assembly or medium at a 15 degree submersion angle at various vertical positions from the surface of the medium. For example, referring to the chart of FIG. 3, a submersion of 0.2 m from the surface at a 15 degree submersion angle results in a force of approximately 22N acting on the transducer array. While FIG. 3 illustrates controlled submersions at a 15 degree angle, a plurality of controlled submersions can be performed at various submersion angles to generate data regarding acting forces against the treatment head from submersion. From this, average buoyancy forces at specific pose angles (known throughout workflow from robot positional data) over the vertical position can be estimated. Additionally, the forces acting in the x, y, and z directions against the transducer array can also be estimated/calculated. While FIG. 3 illustrates an example of calculating or measuring buoyancy forces at a 15 degree submersion angle, it should be understood that this process can be repeated for other submersion angles and depths, including no submersion angle (e.g., where the treatment head is orthogonal to the water or acoustic coupling medium/fluid surface).

In some embodiments, the buoyancy forces acting against the treatment head can be calculated or estimated with a model equation with best fit coefficients. Inputs into the model equation including, but not limited to treatment head depth within the coupling medium and/or treatment head angle of insertion can be used to estimate or calculate the buoyancy. The buoyancy force vs. position below water/coupling medium level can be fit well at each angle of the treatment head with a sigmoidal function. Sigmoidal coefficients can then be fit versus submersion angle. The force acting against the treatment head as a result of submersion can then be estimated strictly as a function of pose (e.g., angle and position of the treatment head) and the vertical position of the treatment head with respect to the surface of the coupling medium (e.g., depth). In some examples, both the angle of the treatment head and the depth can be determined automatically, such as with sensors on the robotic arm and/or treatment head. In other embodiments, the depth of insertion into the coupling container can be a user input.

In one example, a formula to calculate the buoyancy force acting against the transducer array is below in Formula 1:

$$z = -\text{position}(3) + z\_\text{water};$$

$$\text{rot\_ang} = \text{sqrt}(\text{sum}(\text{position}(4{:}6)\cdot^2));$$

$$\text{rot\_vec} = \text{position}(4{:}6)\cdot/\text{rot\_ang};$$

$$uz = [0\,0\;\cos(\text{rot\_ang})] + \text{cross}(\text{rot\_vec}, [0\;0\;1])*\sin(\text{rot\_ang}) + \text{rot\_vec}*\text{rot\_vec}(3)*(1-\cos(\text{rot\_ang}));$$

$$\text{theta} = a\;\cos(uz*[0;0;-1]);$$

$$A = -75 + 5*\text{theta}/6;$$

$$B = 0.15*\cos(\text{theta});$$

$$C = 23 + 4.9*\sin(\text{theta});$$

$$\text{predicted\_force} = C/(1 + \exp(A*(z-B)));$$

Figure 7:
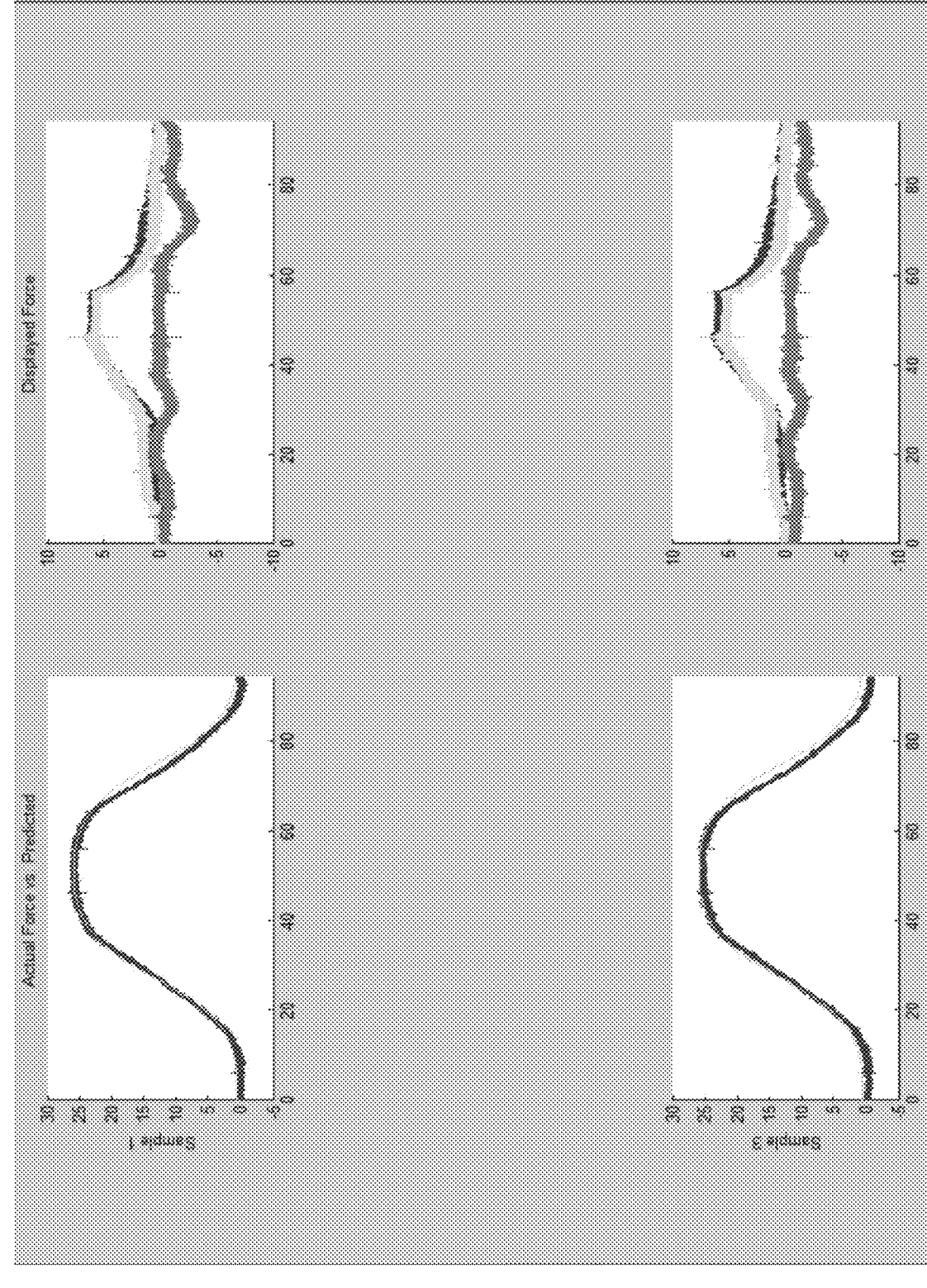

In this example, the predicted buoyancy force acting against the treatment head can be calculated for any selected, measured, or controlled pose angle. FIGS. 4-7 illustrate actual force vs. estimated/calculated force for vertical submersion (FIG. 4), 15 degree pose angle (FIG. 5), 30 degree pose angle (FIG. 6), and 45 degree pose angle (FIG. 7). The left column of data in each figure shows chart of actual force measured against the treatment head at the respective pose angles vs. predicted or calculated forces using Formula 1. The right column of data in each figure shows clinically relevant force in each of the X, Y, and Z directions acting against the transducer array. This force is adjusted to remove the buoyancy forces calculated in the left side of the column. In some embodiments, the resulting relevant force (with buoyancy removed) in each direction can be displayed to the user.

In one implementation, an electronic controller, robotic positioning system, and/or treatment planning system can be configured to look-up, determine, or calculate buoyancy forces acting against the treatment head and robot (e.g., from the coupling medium within the coupling assembly), and to remove, subtract, or account for those buoyancy forces during histotripsy procedures and therapy. By knowing and accounting for the buoyancy forces acting against the treatment head, the system can then accurately calculate and monitor the clinically relevant forces acting against the treatment head. For example, if the robotic positioning system moves the therapy transducer component into contact with the patient and/or the coupling assembly during the course of navigating the treatment plan, the system can know the actual or true forces being applied by the treatment head to the patient and/or coupling assembly. The system can use this information to determine and modify behavior, which may include the ability to command and pause, terminate, or modify treatment or navigation of the treatment plan when excessive forces risk harming the patient and/or damaging system components, such as damaging the therapy transducer, imaging probe, robotic arm, coupling medium container, or other related/connected components. Additionally, the actual or true forces acting against the treatment head can be used in other scenarios/workflows of the system, including across some or all of patient set-up, targeting, planning, threshold testing, and automated treatment portions of the overall therapy and pre-therapy workflows.

Figure 8A:
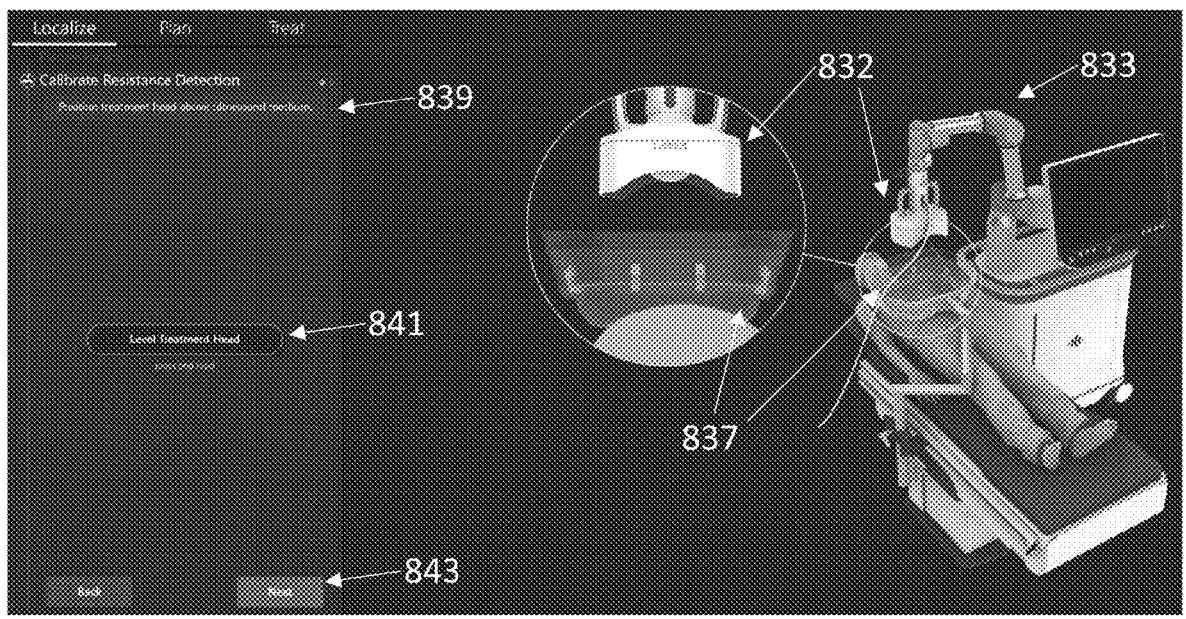
FIGS. 8A-8X illustrate examples of a GUI or user interface of a histotripsy therapy system that can include indications about an amount and/or direction of force applied to the therapy transducer array and/or robotic positioning arm.
Figure 8B:
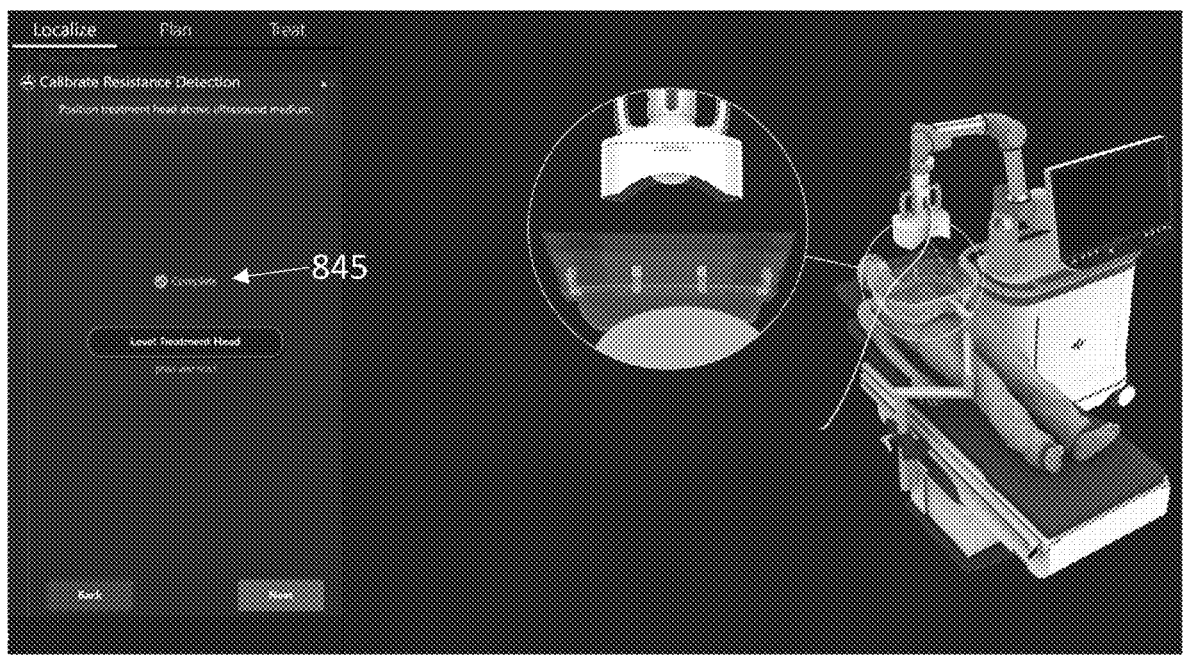
Figure 8C:
Figure 8D:
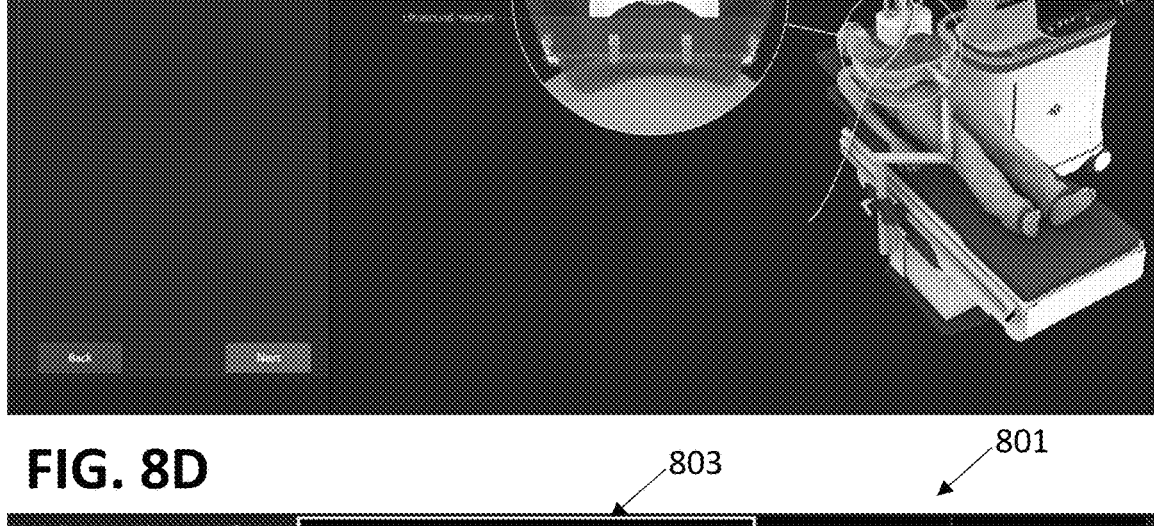
Figure 8D:
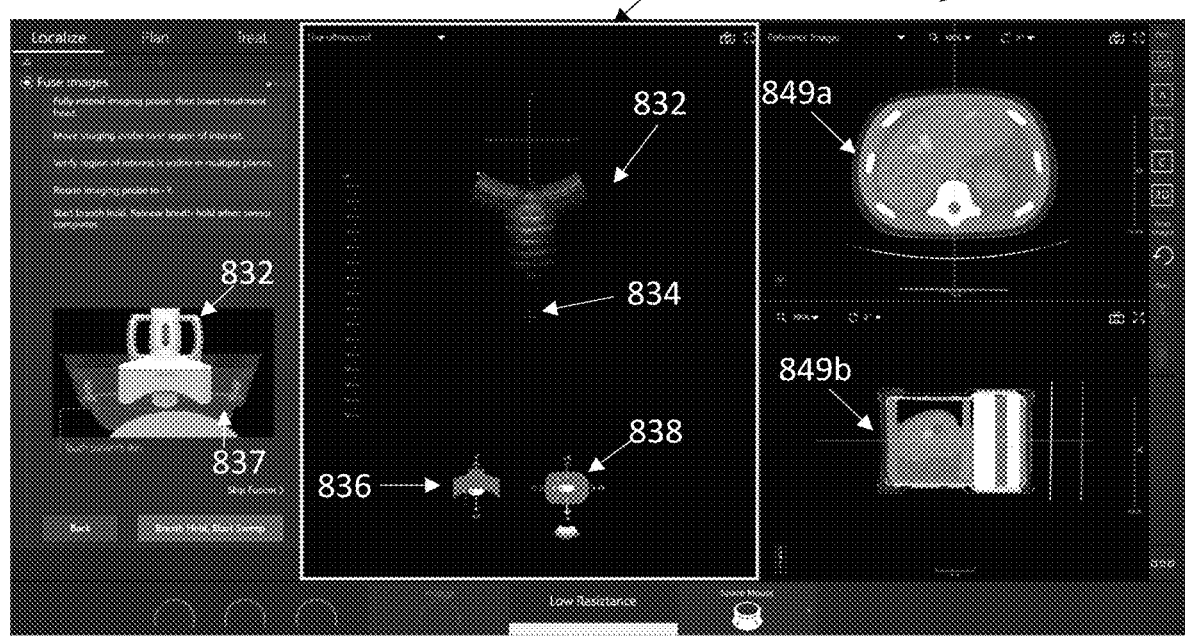
Figure 8E:
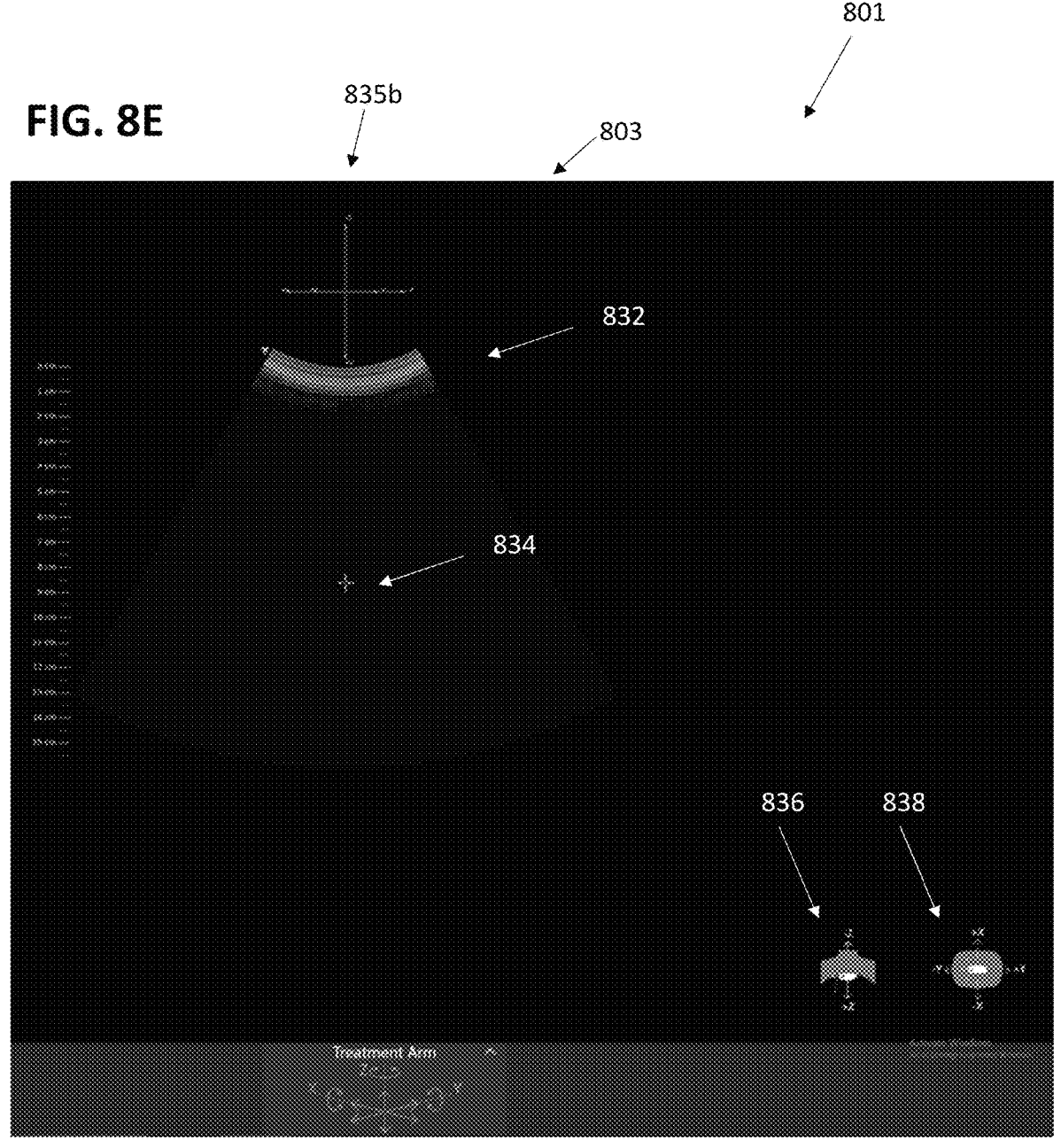
Figure 8F:
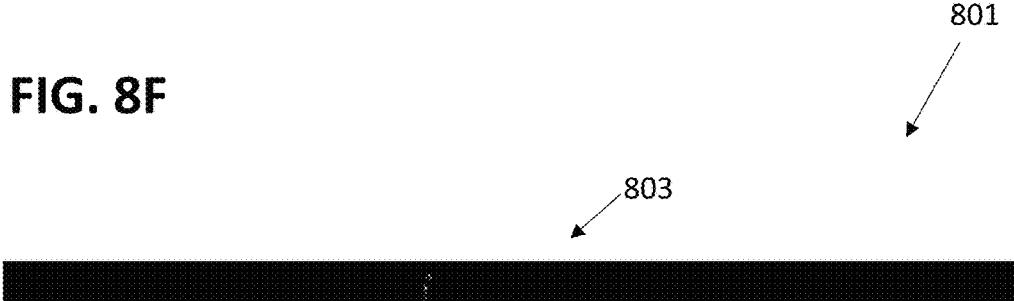
Figure 8F:
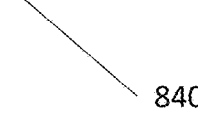
Figure 8G:
Figure 8G:
Figure 8H:
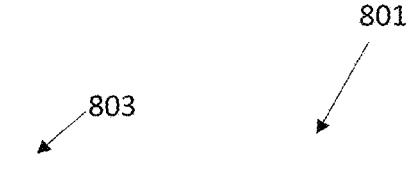
Figure 8H:
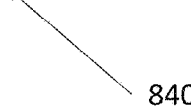
Figure 8I:
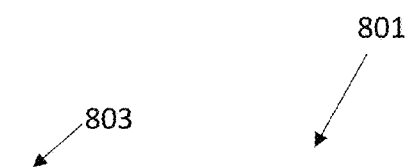
Figure 8I:
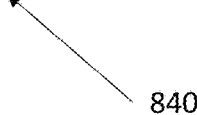
Figure 8J:
Figure 8K:
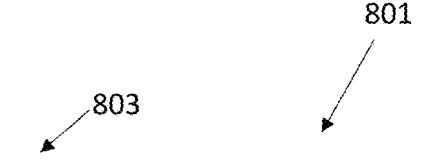
Figure 8K:
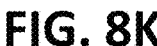
Figure 8K:
Figure 8L:
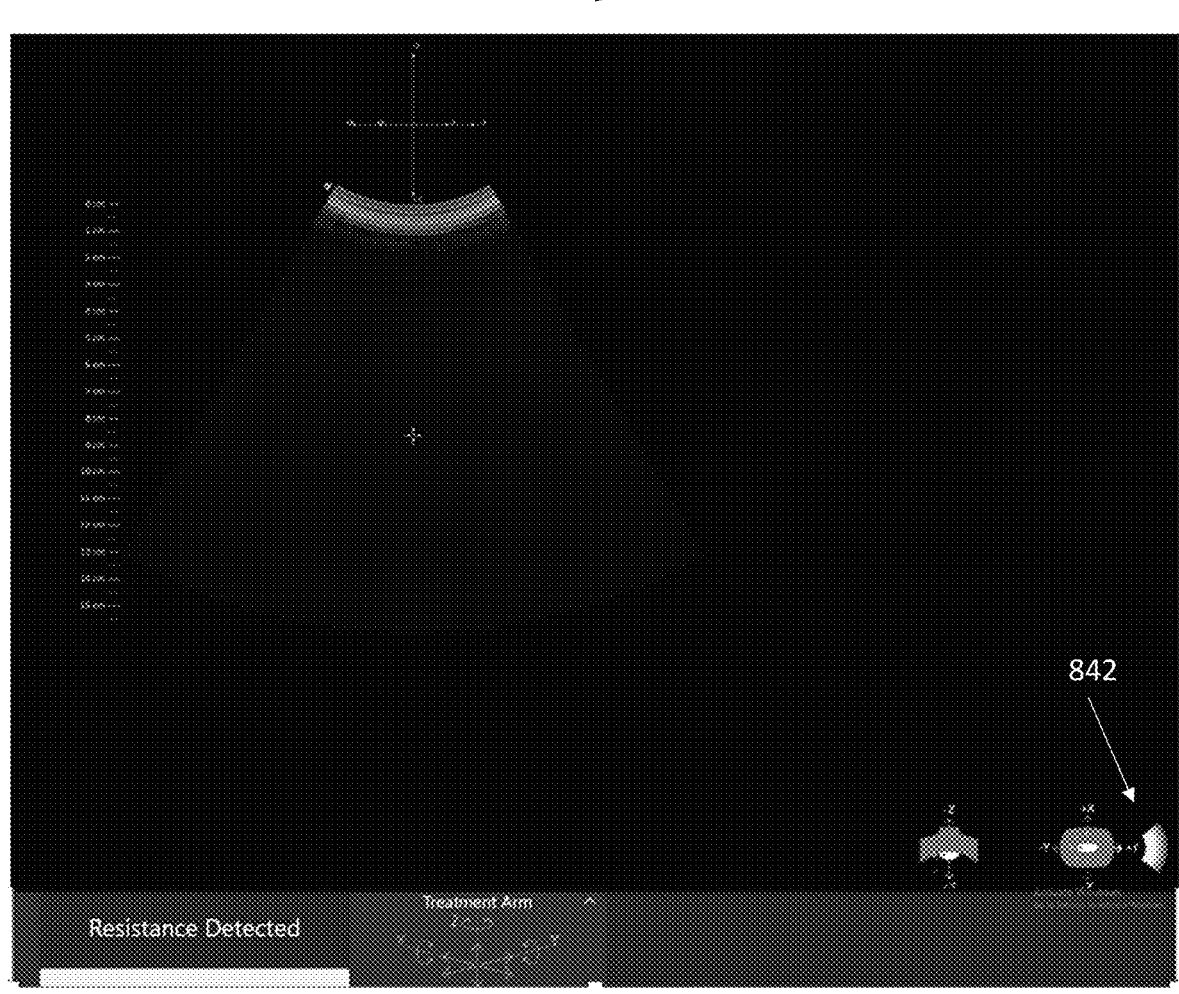
Figure 8M:
Figure 8N:
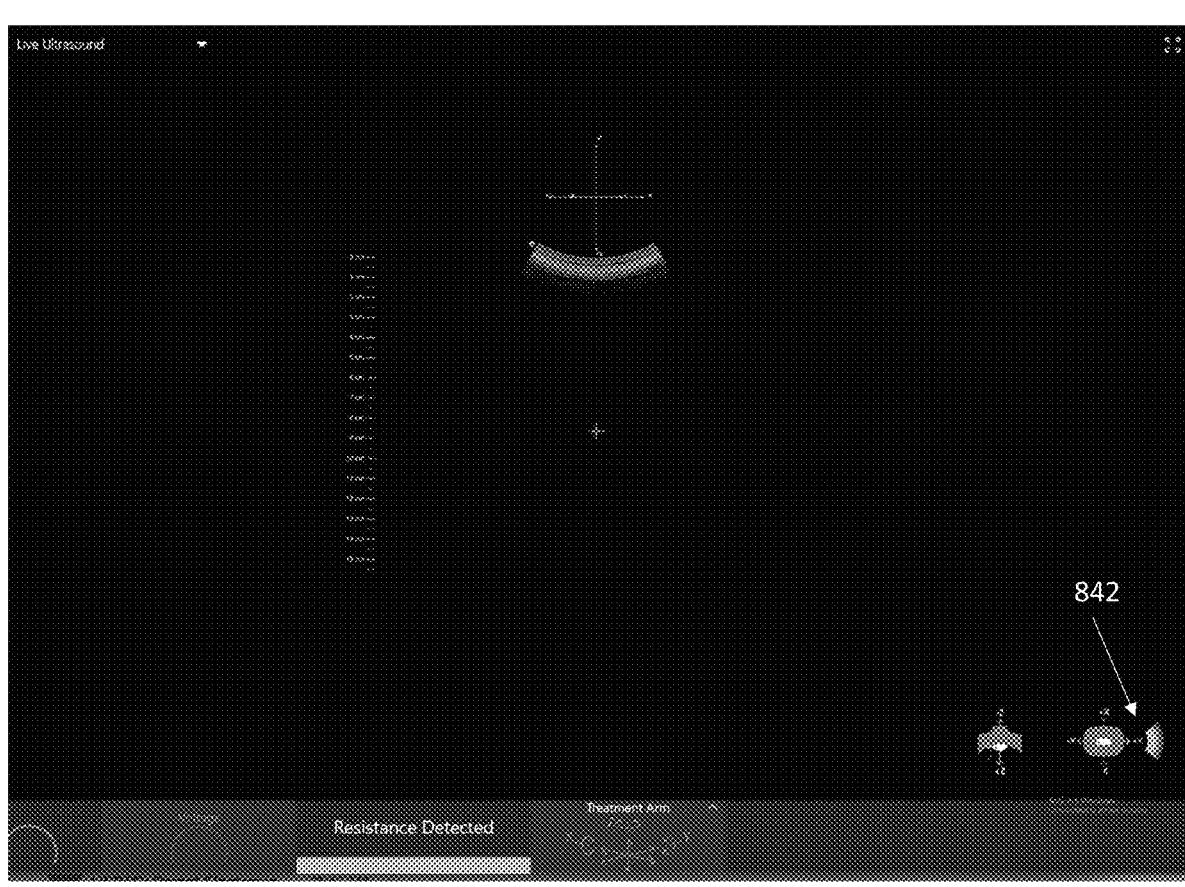
Figure 8O:
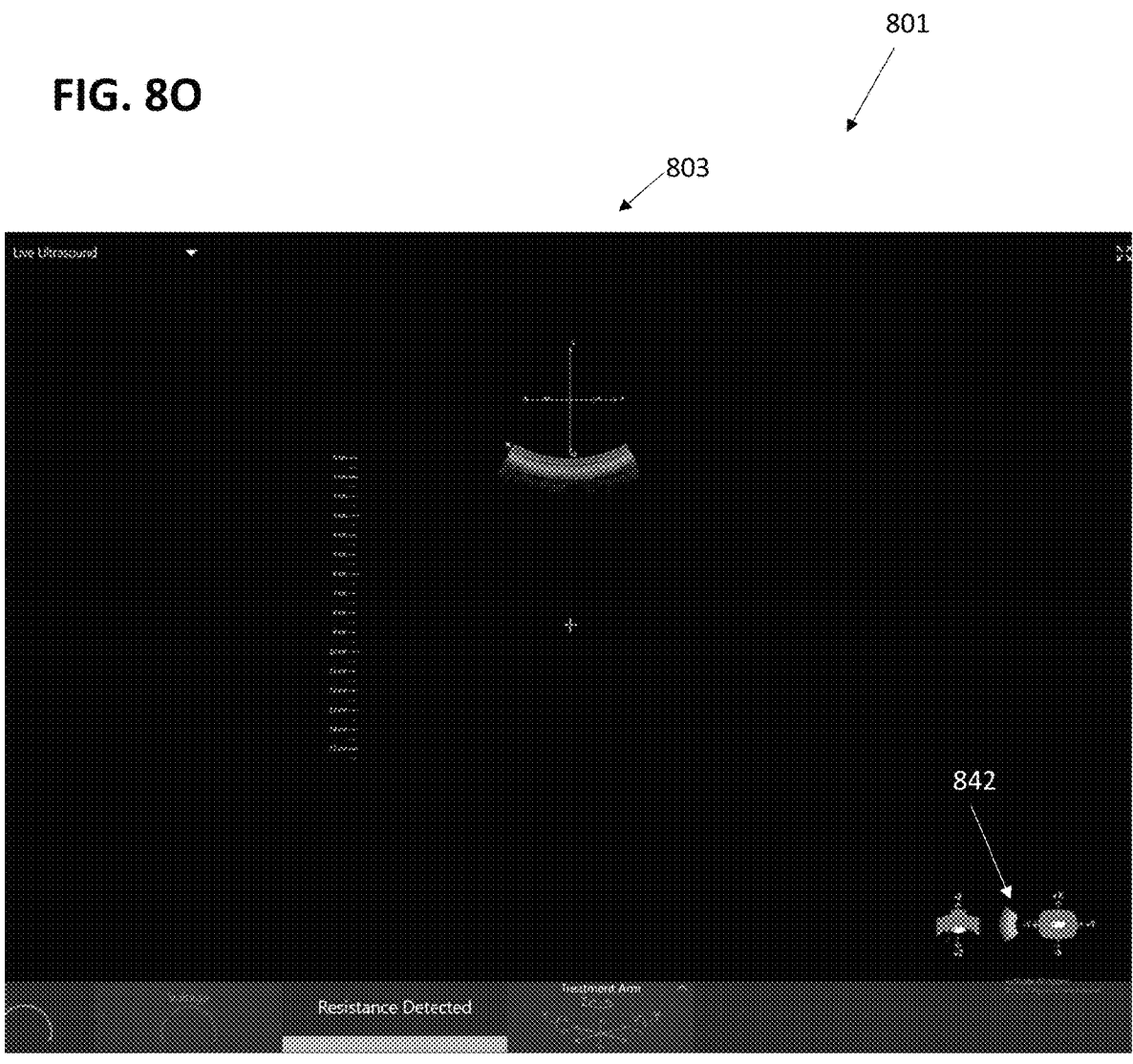
Figure 8P:
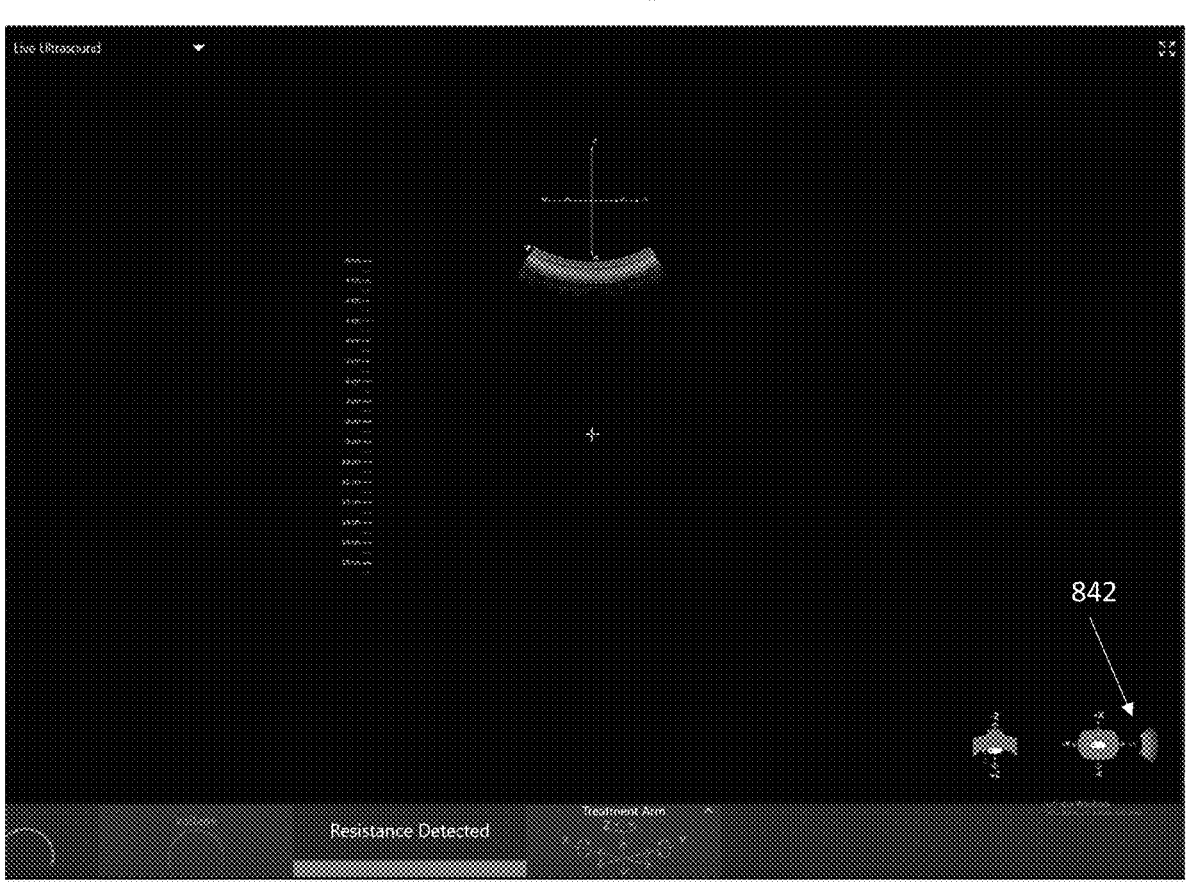
Figure 8Q:
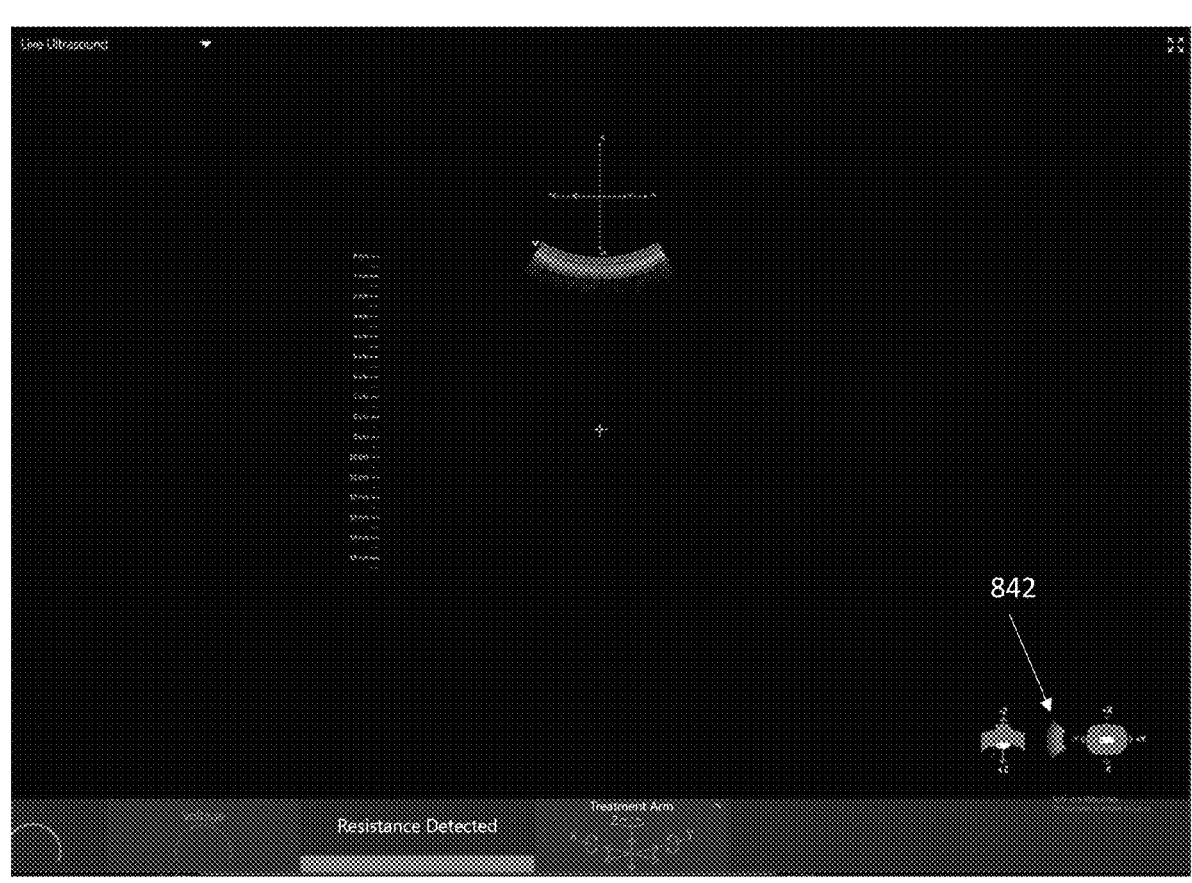
Figure 8R:
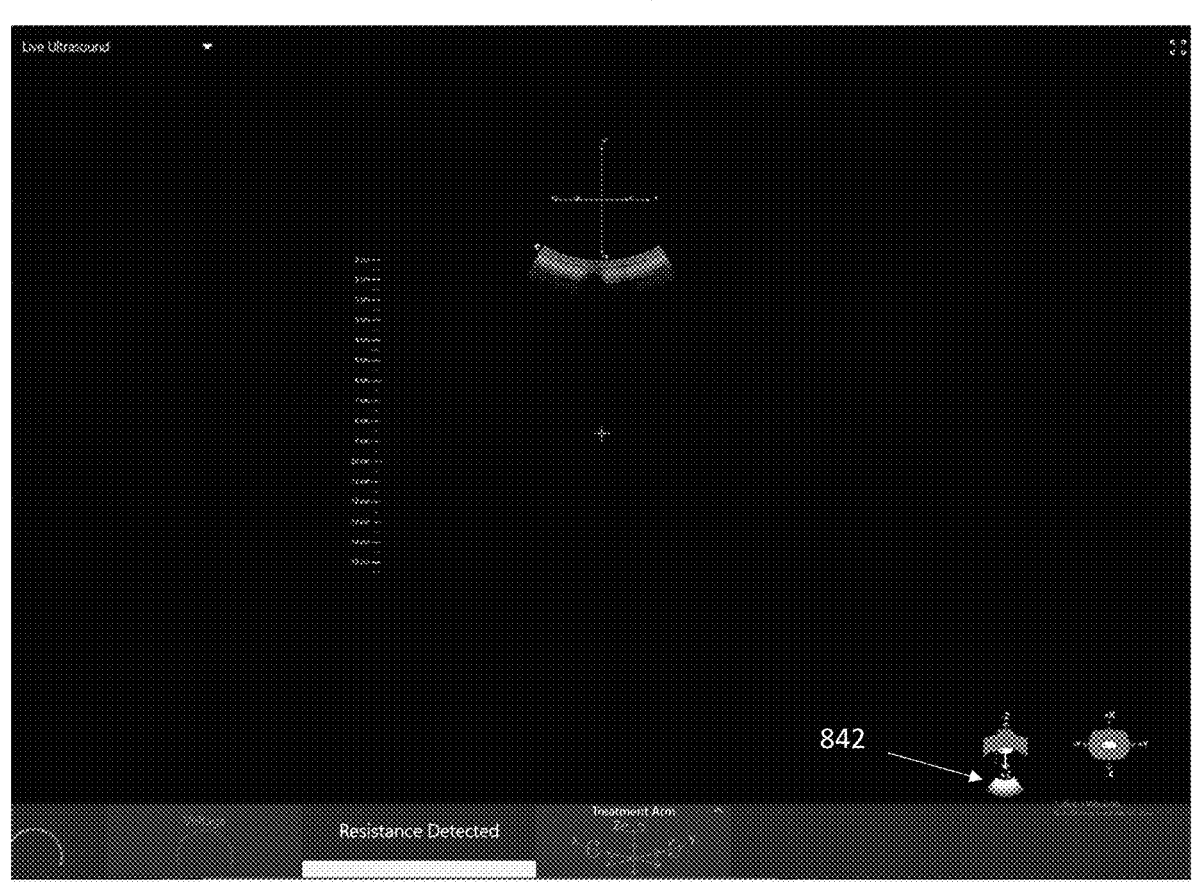
Figure 8S:
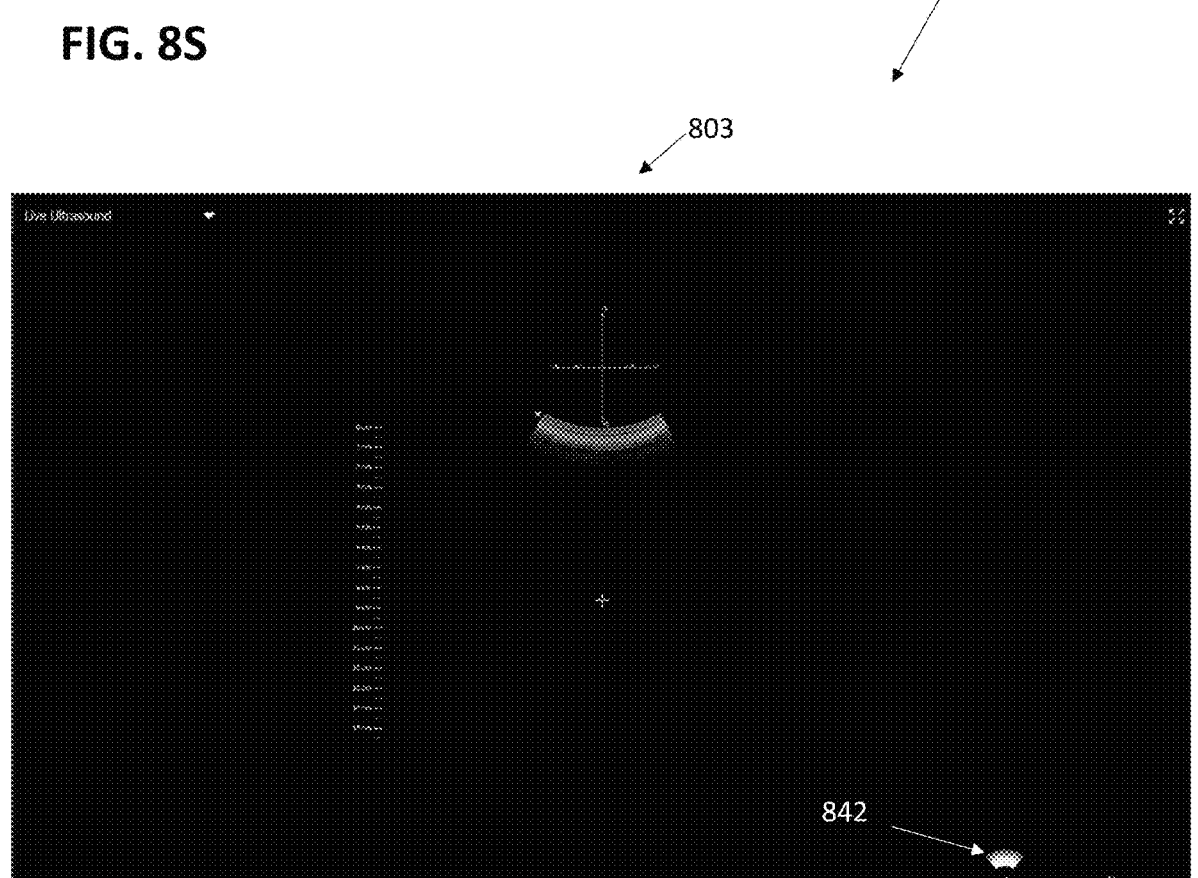
Figure 8S:
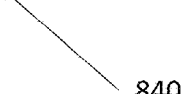
Figure 8T:
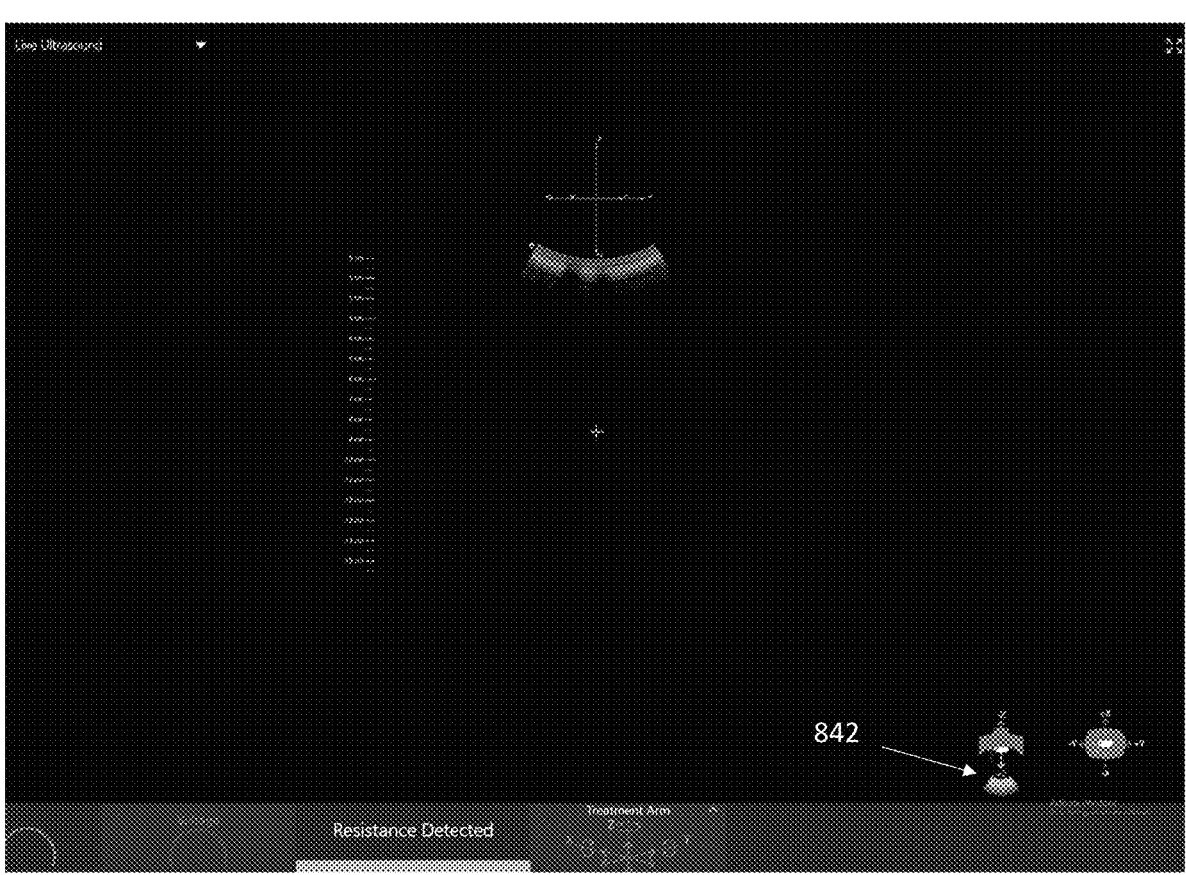
Figure 8U:
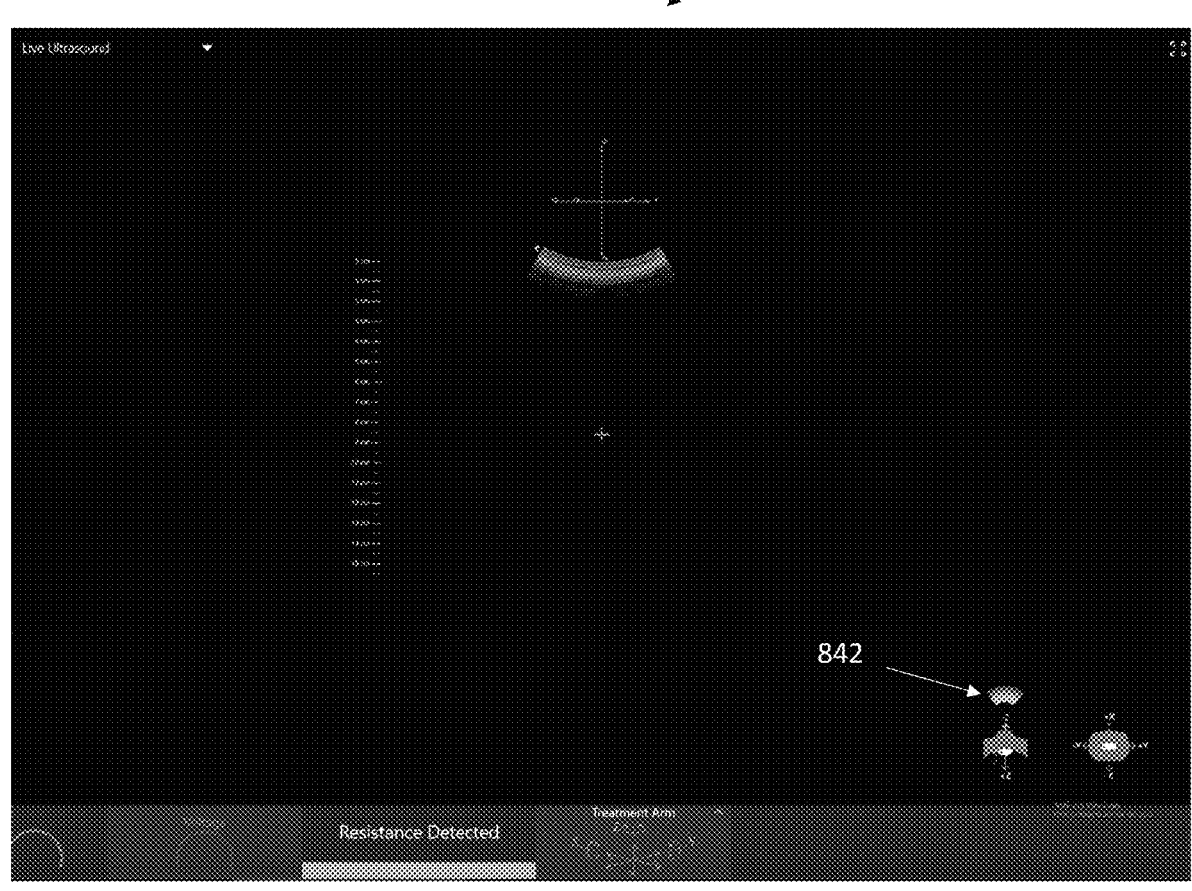
Figure 8V:
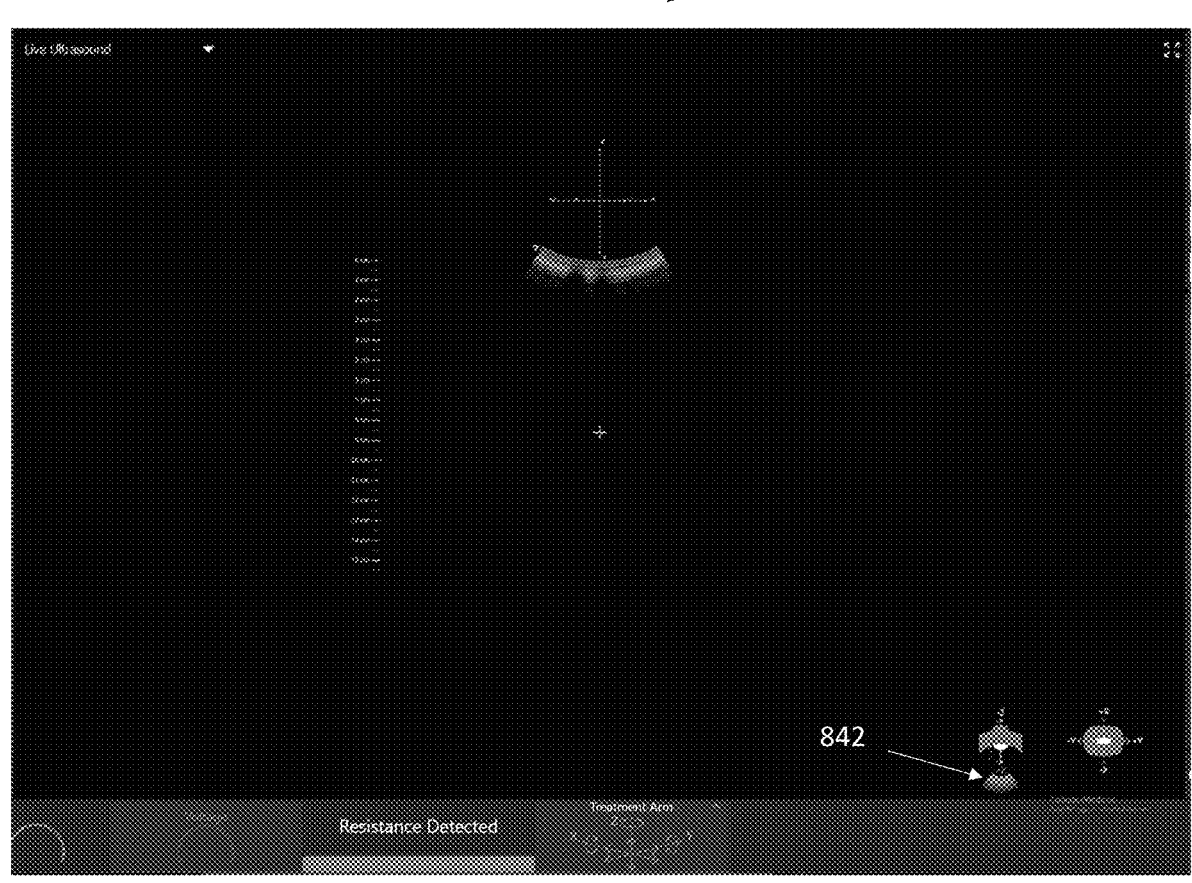
Figure 8W:
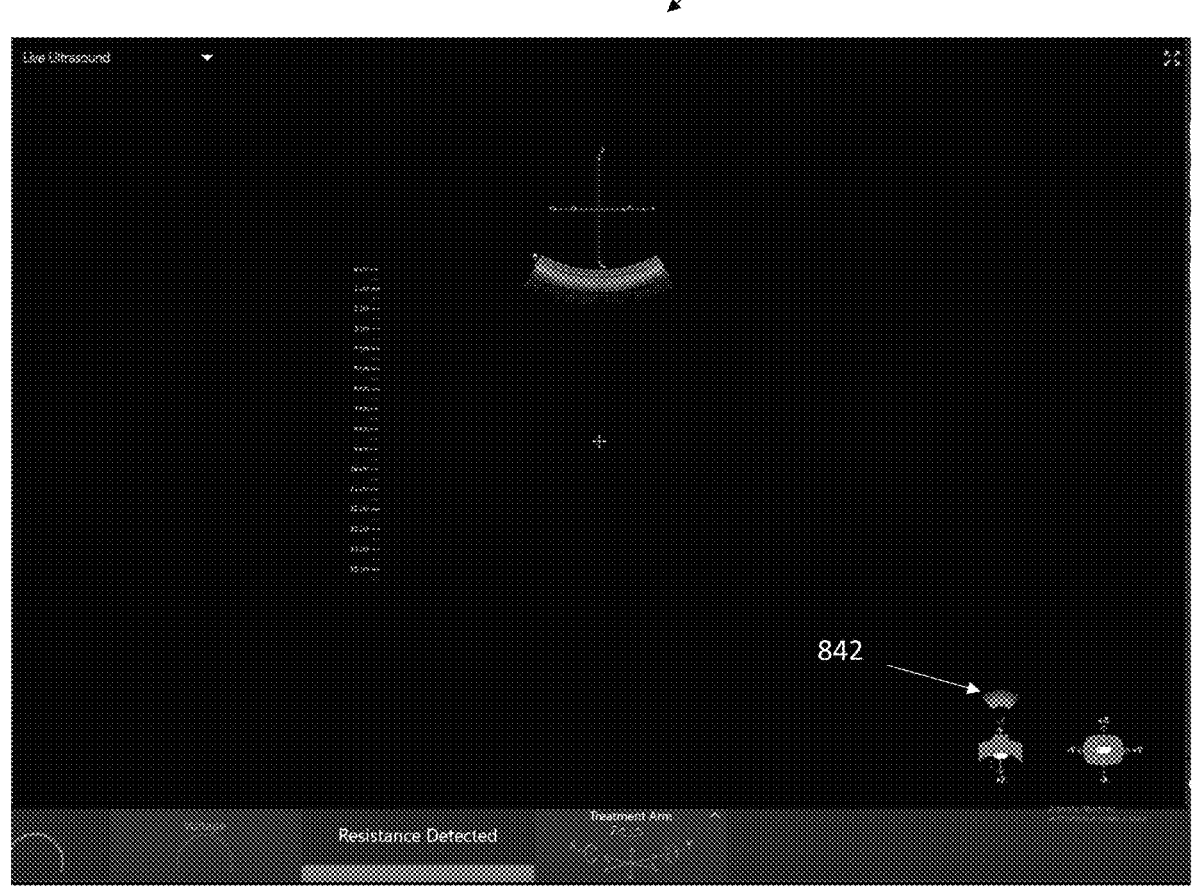
Figure 8X:
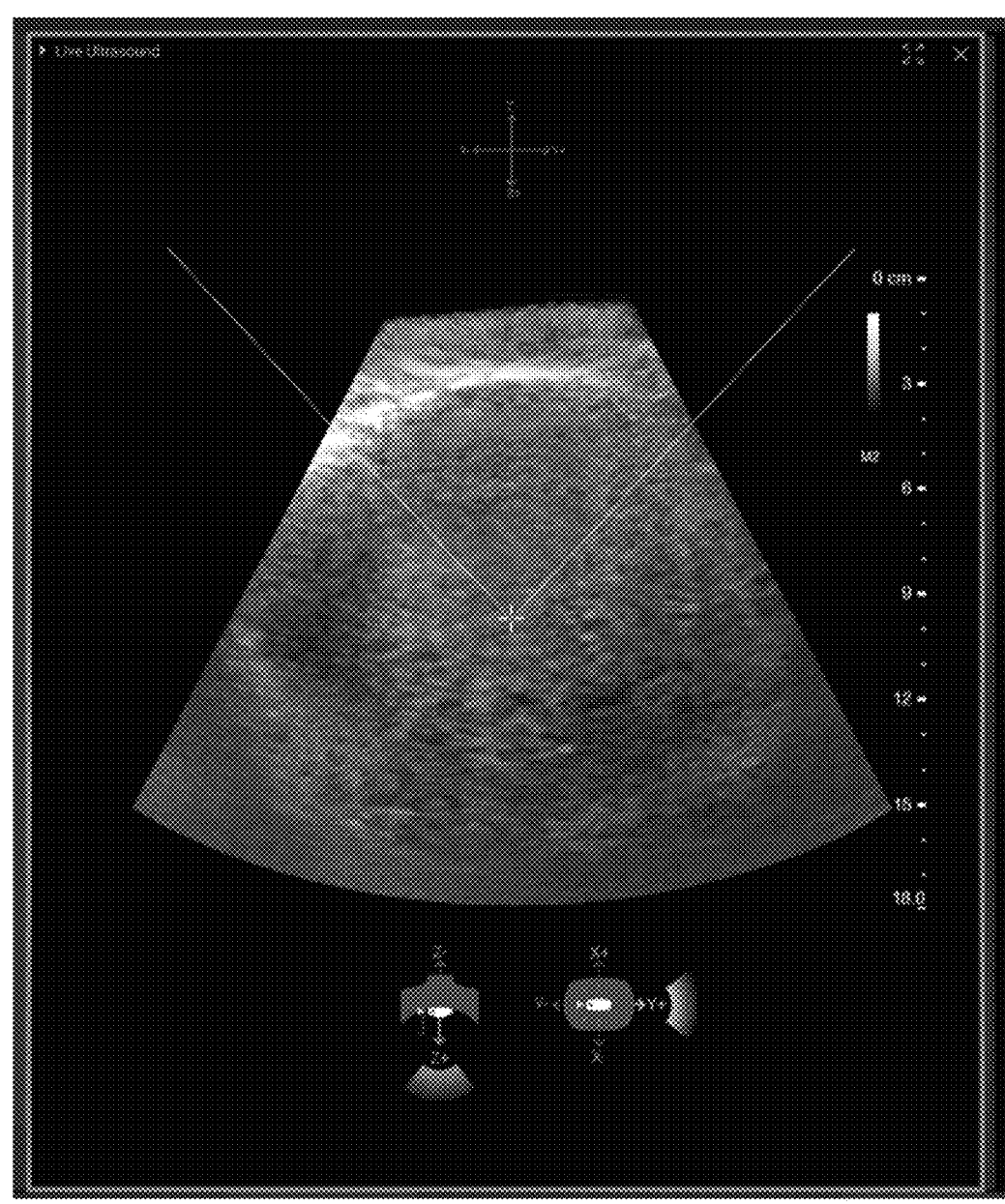

FIGS. 8A-8X illustrate examples of a GUI or user interface 801 of a histotripsy therapy system, such as the system described herein. In some embodiments, the GUI or user interface can be presented to a user on a console or display of the system. The GUI interface can guide a user of a histotripsy therapy system through a histotripsy procedure, including initial setup and calibration of a treatment head of the system to facilitate force monitoring and force feedback of the treatment head during the histotripsy procedure. Referring to FIG. 8A, the GUI 801 can include one or more visual representations of a treatment head 832 and/or therapy transducer coupled to a robotic positioning system or arm 833. The GUI can further include one or more graphical or visual representations of a coupling container 837 placed over a patient for acoustically coupling the treatment head to the patient. As described above, the coupling container of the histotripsy system may be filled or partially filled with an acoustic coupling medium (e.g., degassed saline or fluid) to acoustically coupled the treatment head to the patient.

At the start of a histotripsy procedure, still referring to FIG. 8A, the GUI 801 can direct the user with prompt 839 to position the treatment head above the ultrasound medium (e.g., the acoustic coupling medium) of the coupling container. The GUI 801 can further include an interface 841 that directs the robotic positioning system to level the treatment head (e.g., achieve an insertion angle of 0). When the treatment head is positioned, the user can interact with interface 843 to indicate that the treatment head is properly positioned above the ultrasound medium. In FIG. 8B, the GUI can provide a prompt 845 that this positioning step has been completed.

At FIG. 8C, the GUI 801 can direct the user with prompt 847 to lower the treatment head (e.g., with a user input device such as a "space mouse", mouse, keyboard, joystick, or other user input device) until the treatment head touches or contacts the ultrasound medium. While the illustrated embodiment prompts the user to manually control movement of the treatment head until the treatment head contacts the acoustic medium, other embodiments are provided in which this step is automated. For example, once the treatment head is positioned over the acoustic medium, the user may be prompted to initiate resistance detection which can then automatically control lowering of the treatment head towards the acoustic medium until resistance is detected (e.g., with force sensors on the robotic arm). As soon as the treatment head touches the acoustic medium, these forces can be detected and stop movement of the treatment head precisely at the upper level of the acoustic medium. Other sensors can be used to detect when the treatment head contacts the acoustic medium, including for example optical, contact, or acoustic sensors on the treatment head or within the coupling container.

Placing the treatment head at the acoustic medium surface indicates to the system where the acoustic coupling medium is in 3D space. Any further movement of the treatment head in the +z direction will be into the acoustic coupling medium, resulting in buoyancy forces acting against the treatment head. Therefore, the system can determine or calculate any forces applied against the treatment head once therapy starts that are attributed to buoyancy forces from the acoustic medium, and subtract them to give a true indication of forces acting against the treatment head as a result of contact with the coupling container, the patient, or other persons such as medical personnel.

Once the acoustic medium surface been calibrated/zeroed in 3D space, histotripsy treatment can begin. As the treatment head moves within the acoustic coupling medium of the coupling container, forces acting against the treatment head can be continuously or periodically monitored, and buoyancy forces can be subtracted from the measured forces or accounted for to provide a true measure of the forces acting against the treatment head. As described above, the buoyancy forces for a given pose/depth of the treatment head can be calculated with an algorithm (e.g., a sigmoid function) and subtracted from the measured forces acting against the treatment head.

Referring to FIG. 8D, the GUI 801 can provide a graphical overlay 803 or interface that includes a visual representation of treatment head 832 that includes the acoustic field or focal point 834 of the therapy transducer. In some embodiments, when therapy is active, the visual representation of the treatment head and/or therapy transducer and the acoustic field and/or focal point 834 can also include real-time imaging of the cavitation produced by the histotripsy therapy. Furthermore, the GUI 801 shows a side-view 836 of the treatment head showing the probe in the z plane and a top-down view 838 of the treatment head showing it in the x-y plane. Generally herein, the z plane of the treatment head is defined as the axis along which therapy is delivered.

Additional information can be provided to the user on the GUI 801, including pre or peri medical or diagnostic images 849a/849b (e.g., CT, MRI, ultrasound, etc.) of the patient and/or the target tissue volume to be treated. The images 849a/849b can be presented in on or more imaging planes or slices, can also be manipulated (e.g., zoomed, rotated, adjusted, marked-up, etc.) by the user as needed.

In some embodiments, a real-time graphical representation of the relative location or orientation of the treatment head 832 relative to the coupling container 837 can also be provided on GUI 801, as shown.

In the example of FIG. 8E, a close-up view of graphical overlay 803 of the GUI 801 is shown which can provide information on a number of functions or features of the histotripsy system. For example, the graphical overlay 803 of GUI 801 can include a visual representation of the treatment head 832 and/or therapy transducer that includes the acoustic field or focal point 834 of the therapy transducer. In some embodiments, when therapy is active, the visual representation of the treatment head and/or therapy transducer and the acoustic field and/or focal point 834 can also include real-time imaging of the cavitation produced by the histotripsy therapy.

Additionally, the graphical overlay 803 of GUI 801 can further include a xyz plane key 835a and/or 835b that shows the orientation of the xyz coordinate system of the histotripsy therapy system with respect to a visual representation of the treatment head. Furthermore, the GUI 801 shows a side-view 836 of the treatment head showing the probe in the z plane and a top-down view 838 of the treatment head showing it in the x-y plane. As will be described in more detail below, the side-view 836 and top-down view 838 can provide indications to the user about forces applied by the treatment head and robotic arm to objects such as when the treatment head is moved or translated by the robotic arm so as to contact the patient and/or the coupling assembly of the system. Further, indications are also provided to the user about forces applied to the treatment head or robotic arm such as an accidental bump or forces applied to the system by another person, object or medical system. Advantageously, the force sensing of the system and force indications provided by the GUI to the user provide an important safety feature to ensure that the patient and/or the equipment is not damaged or harmed during therapy due to movement of the robotic arm and treatment head, or forces exerted thereon. Additionally, the indications to the user about forces applied to the treatment head or other system components can be calibrated or adjusted to account for buoyancy forces acting against the treatment head and robotic arm, so as to provide a true or accurate indication of the acting forces on the patient and/or system components. The clinically relevant forces acting against the system components can further be used to modify or halt therapy (either by user or automatically when a set force threshold is met) in situations where harm may occur to the patient or system components across the work-flow.

Referring to FIGS. 8F-8G, the graphical overlay 803 of GUI 801 can further include a force indication 840 that displays an amount or indication of the force applied against the system. In this example, the force indication 840 can be used in conjunction with directional force indicator 842 to indicate to the user 1) an indication of the amount of force applied against the treatment head and 2) the direction or location on the treatment head where the force is being applied. Additionally, as described above, all embodiments described herein where the applied force is displayed to the user can be adjusted or calibrated to account for buoyancy forces acting against the system components as a result of the coupling medium. As shown in FIG. 8F, the force indication 840 in this example provides a color-coded indication to the user representing the amount of force applied against the probe. In one example, the color-coded force indication can comprise a yellow color code for a "low" or "acceptable" range of forces, an orange color code for a "medium" or "increased" range of forces, and a red color code for a "high" or "excessive" or "dangerous" range of force. However, it should be understood that other colors can be used in a color-coded system, or other indication systems, such as visual, audible and tactile indication systems can be used that do not rely on displayed colors to indicate the force. For example, the force indication 840 can display words to the user such as "low force", "medium force", or "high force" or "dangerous force". Generally, the force indication can provide any number of levels of force indication, including three or more force levels (e.g., low, medium, high). In other embodiments, only a single force indication (e.g., "high" or "excessive") is indicated to the user. Alternatively, the force indication can display the actual measured force value to the user (e.g., 20 ft/lbs of force, etc.).

Generally, the indications of the force level or ranges of forces being applied against/with the treatment head can fall into at least three categories. For example, reference to "low" or "acceptable" ranges of forces can describe forces that fall within a range of forces that are within operating ranges and will not cause damage or harm to the patient, or any of the system hardware, including the coupling container, the treatment head, the robotic arm, etc. "Medium" or "increased" force ranges can refer to ranges of forces that are elevated beyond normal operating ranges and indicate some contact between the system and a foreign body (e.g., the patient, the coupling container, etc.). While these increased forces may not be enough to cause damage to the system or the patient, they can be indicative of unplanned contact or collisions between the treatment head and something else. These levels of forces can generally be used to alert or warn the user about a potential problem with the system. Finally, reference to "high" or "dangerous" forces indicate a serious problem with the system, such as collisions between the treatment head and the patient or another aspect of the system that can cause harm to the patient and/or the system. While these forces are also typically indicated to the user, the system can further implement safeguards within the system that immediately stop treatment or reverse/adjust treatment head movement to attempt to avoid or eliminate the excessive forces.

In combination with the force indicator 840, the graphical overlay 803 of GUI 801 can also display the direction or location of the measured force on a representation of the treatment head itself with directional force indicator 842. In FIG. 8F, for example, directional force indicator 842 shows that the "low" or code yellow force is being applied against the +X direction of the treatment head. Similarly, FIG. 8G shows that the "low" force is being applied against the −X direction of the treatment head. In embodiments where the force indication 840 is a color-coded system, the directional force indicator 842 can display a color that matches the color of the force indication 840. For example, in FIGS. 8F-8G, the force indication 840 can provide a yellow indicator and the directional force indicator 842 can also display a yellow indicator in the +X and −X directions, respectively.

FIGS. 8H-8I illustrate an example of graphical overlay 803 of GUI 801 with force indication 840 and directional force indicator 842 showing that a "medium" or code orange force is being applied against the +X and −X directions of the treatment head, respectively. As with the examples above, the indication of the force applied to the treatment head or robotic arm(s) can be adjusted or calibrated to account for buoyancy forces acting against it or robotic arm from the coupling medium within the coupling assembly.

The remaining FIGS. 8J-8X illustrate the various permutations or examples of the "low", "medium", and "high" force indicator levels to the user for each of the +/−X, Y, and Z directions of the treatment head. Specifically:

FIGS. 8J-8K illustrate an example of GUI 801 with force indication 840 and directional force indicator 842 showing that a "high" or code red force is being applied against the +X and −X directions of the treatment head, respectively. As with the examples above, the indication of the force applied to it or robotic arm(s) can be adjusted or calibrated to account for buoyancy forces acting against the probe or robotic arm from the coupling medium within the coupling assembly.

FIGS. 8L-8M illustrate an example of GUI 801 with force indication 840 and directional force indicator 842 showing that a "low" or code yellow force is being applied against the +Y and −Y directions of the treatment head, respectively. As with the examples above, the indication of the force applied to it or robotic arm(s) can be adjusted or calibrated to account for buoyancy forces acting against the probe or robotic arm from the coupling medium within the coupling assembly.

FIGS. 8N-8O illustrate an example of GUI 801 with force indication 840 and directional force indicator 842 showing that a "medium" or code orange force is being applied against the +Y and −Y directions of the treatment head, respectively. As with the examples above, the indication of the force applied to it or robotic arm(s) can be adjusted or calibrated to account for buoyancy forces acting against it or robotic arm from the coupling medium within the coupling assembly.

FIGS. 8P-8Q illustrate an example of GUI 801 with force indication 840 and directional force indicator 842 showing that a "high" or code red force is being applied against the +Y and −Y directions of the treatment head, respectively. As with the examples above, the indication of the force applied to it or robotic arm(s) can be adjusted or calibrated to account for buoyancy forces acting against it or robotic arm from the coupling medium within the coupling assembly.

FIGS. 8R-8S illustrate an example of GUI 801 with force indication 840 and directional force indicator 842 showing that a "low" or code yellow force is being applied against the +Z and −Z directions of the treatment head, respectively. As with the examples above, the indication of the force applied to it or robotic arm(s) can be adjusted or calibrated to account for buoyancy forces acting against it or robotic arm from the coupling medium within the coupling assembly.

FIGS. 8T-8U illustrate an example of GUI 801 with force indication 840 and directional force indicator 842 showing that a "medium" or code orange force is being applied against the +Z and −Z directions of the treatment head, respectively. As with the examples above, the indication of the force applied to it or robotic arm(s) can be adjusted or calibrated to account for buoyancy forces acting against it or robotic arm from the coupling medium within the coupling assembly.

FIGS. 8V-8W illustrate an example of GUI 801 with force indication 840 and directional force indicator 842 showing that a "high" or code red force is being applied against the +Z and −Z directions of the treatment head, respectively. As with the examples above, the indication of the force applied to it or robotic arm(s) can be adjusted or calibrated to account for buoyancy forces acting against the probe or robotic arm from the coupling medium within the coupling assembly.

The embodiments described above have mostly focused on showing the various force indicators for singular forces acting against the therapy head and/or robotic arm (e.g., a single force acting in a single direction against the system). However, it should be understood that in practice, forces may be applied against the treatment head and/or robotic arm from a plurality of directions simultaneously. It should be understood that in some examples, the system can display and indicate acting forces in more than one direction. FIG. 8X shows an example of a first force acting against the +Z direction of the treatment head while a second force is acting in the +Y direction of the treatment head. In this example, the first force comprises a "high" or code red force acting against the system and the second force comprises a "medium" or code orange force acting against the system. In general, the system can be configured to measure, sense, or determine any number and severity of forces acting against the treatment head and/or robotic arm in any number of directions, and indicate those forces to the user in any of the manners disclosed herein.

Methods of controlling or modifying histotripsy procedures and therapy based on the measured and/or displayed forces acting against the system and/or components of the system including the robotic sub-systems are also provided. As described above, the systems and methods provided herein can provide valuable information to a user and/or to the controllers or processors of the system relating to the forces acting upon the transducer array and/or robotic sub-systems, including the robotic positioning arms. This information can be used by the user and/or system to modify, adjust, pause/terminate, and/or reinitiate the therapy in the event that it is determined the specific forces and scenarios are excessive or may cause harm to the patient and/or system components, and with such responses and commanded behaviors specialized by work-flow stage and status.

FIG. 9 is a flowchart describing a method of dynamically calibrating an ultrasound system to determine an acoustic coupling medium surface location in 3D space.

At step 902 of FIG. 9, the method can include positioning an ultrasound treatment head near an acoustic coupling medium. The acoustic coupling medium may be contained within a coupling container that is positioned on a patient, for example. In some aspects, positioning the treatment head near the acoustic coupling medium can comprise positioning the treatment head near the acoustic coupling medium with a robotic positioning system. The positioning can be automatically controlled by one or more processors of the ultrasound therapy system, or alternatively, may be manually positioned by a user (e.g., by physically manipulating the treatment head). Typically the coupling container is placed on top of a patient's skin, so the positioning step may include positioning the treatment head above a surface of the acoustic coupling medium.

At step 904 of FIG. 9, the method can include identifying the location of the acoustic coupling medium surface in 3D space. In one implementation, the surface of the acoustic coupling medium can be identified by moving or positioning the treatment head at the acoustic coupling medium surface. The treatment head can be moved or positioned with the robotic positioning system (e.g., automatically or manually controlled by the user) or alternatively, can be physically manipulated by the user. In one aspect, once the treatment head is positioned at the acoustic coupling medium surface, the system can receive an input from the user indicating the surface level, and this position can be "zeroed" out in the system to indicate the surface level relative to the treatment head position (or position of the robotic positioning system) in 3D space.

In other aspects, the system can identify the acoustic coupling medium surface automatically. For example, the robotic positioning system can move/lower the treatment head until forces measured by the system are detected, such as forces applied against the treatment head when the treatment head first contacts the acoustic coupling medium. Alternatively, one or more sensors on the treatment head itself (e.g., contact sensors, acoustic sensors, optical sensors) can measure or detect the surface level, sometimes even without having to physically move the treatment head into contact with the acoustic surface. Additionally, as described herein, the coupling container itself may have sensors configured to measure or indicate the surface level of the acoustic coupling medium.

At step 906 of FIG. 9, the method can include registering the acoustic coupling medium surface position to the 3D coordinate system of the robotic positioning arm or the treatment head. For example, when the surface level is detected or identified in step 904, the surface level can be registered or identified within the robotic positioning system coordinate system. In examples where the treatment head is physically placed in contact with the surface level, the system can mark the physical position of the treatment head as the location of the acoustic coupling medium surface. Then, during therapy, the system knows that any movement of the treatment head in the +z direction past the acoustic coupling medium surface will result in buoyancy forces of the coupling medium acting against the treatment head.

Optionally, at step 908 of FIG. 9, the method can include at least partially submerging the treatment head into the acoustic coupling medium. This can comprise, for example, controlling the robotic positioning arm to move the treatment head into the acoustic coupling medium below the surface of the acoustic coupling medium.

Optionally, at step 910 of FIG. 9, the method can include determining buoyancy forces acting against the treatment head based on the depth and pose of the treatment head. The depth can be automatically determined by the system based on the amount of treatment head movement (as controlled by the robotic positioning system) below the surface of the acoustic coupling medium as identified above in step 904. The pose of the treatment head can also be automatically determined with the robotic positioning system, by identifying or sensing the pose angle/orientation of the arm where it attaches to the treatment head, such as with accelerometers, gyroscopes, or other orientation sensors of the robotic positioning arm.

FIG. 10 is a flowchart describing one method of measuring, determining, indicating, and using force applied against a treatment head and/or robotic positioning arm of a histotripsy therapy system during therapy. As described above, the method can advantageously account for, subtract from, or use buoyancy forces acting against the treatment head to determine the clinically relevant forces acting against the treatment head or robotic arm resulting from the histotripsy procedure, including forces caused by collisions between the probe/arm and a patient or medical provider or between the treatment head/arm and a coupling assembly of the histotripsy system.

At step 1002 of FIG. 10, the method can include the step of at least partially submerging the treatment head in an acoustic coupling medium. The acoustic coupling medium may be contained within a coupling container that is positioned on a patient, for example. In some aspects, submerging the treatment head in the acoustic coupling medium can comprise positioning the treatment head in the acoustic coupling medium with a robotic positioning system. The positioning can be automatically controlled by one or more processors of the ultrasound therapy system, or alternatively, may be manually positioned by a user (e.g., by physically manipulating the treatment head).

The treatment head can be moved, for example, with a robotic sub-system that can include at least one robotic positioning arm. As is further described herein, a histotripsy treatment may include a treatment plan that provides a plurality of treatment locations (focal locations) within the patient's body. The treatment locations may be mapped or correlated to focal point(s) of the treatment head (and therapy transducer array component). Thus, submerging the treatment head in the acoustic coupling medium may comprise positioning the treatment head within the coupling container to place a focus of the treatment head at a treatment/focal location within the patient. It should be understood that when the treatment location is inside the patient's body, movement of the treatment head to a position within the coupling container that places the focus at the treatment location may include moving the treatment head to a location outside of the patient's body. In some examples, as described above, the treatment head may be moved entirely within the confines of a coupling assembly filled with an acoustic coupling medium so as to acoustically couple the therapy transducer on the outside of the body to the patient's skin, and therefore to the treatment location within the patient's body.

At step 1004 of FIG. 10, the method can include periodically, repeatedly, and/or continuously determining or measuring the raw forces applied against the treatment head and/or robotic arm. In some examples, this includes measuring or sensing the forces acting against the treatment head and/or robotic arm(s), such as with force sensors on the treatment head or on the robotic arm. The measured forces can be monitored or analyzed by one or more processors of the ultrasound system.

At step 1006 of FIG. 10, the method may include repeatedly or continuously determining or calculating buoyancy forces acting against the treatment head and/or robotic arm(s) for a given pose angle and insertion depth of the treatment head within the acoustic coupling medium. In some embodiments, the buoyancy forces are calculated in real-time by the histotripsy system based on the depth of insertion of the treatment head in the acoustic coupling medium, the current pose angle of the treatment head, and information relating to the size and configuration of the robotic arm and the treatment head. The calculation can include, for example, a sigmoid function with depth and pose angle as inputs. In some aspects, the depth and pose are automatically determined by the system, based on sensors on or within the robot/treatment head and/or tracking movement of the treatment head relative to a known position of the acoustic coupling medium surface in 3D space. In some embodiments, the buoyancy forces are pre-calculated and the system can utilize a lookup table or other data source to obtain buoyancy force data for a given pose angle and depth of submersion. The buoyancy forces can be calculated continuously, repeatedly, or at pre-determined time periods as the treatment head and robot are moved towards the target location, region of interest, and/or in and around treatment plans.

Next, at step 1008 of FIG. 10, the method can include determining clinically forces acting against the treatment head and/or robotic arm(s) irrespective of the buoyancy forces. In some examples, this includes subtracting the buoyancy forces calculated in step 1006 from the raw forces acting against the treatment head and/or robotic arm in step 1004. By removing the buoyancy forces from the measured or sensed forces acting against the treatment head and/or robotic arm, the system can determine, calculate, or know the clinically relevant forces acting against the treatment head and/or arm, such as forces caused by a collision between the head/arm and the patient, collisions with medical personnel, or contact between the head/arm and the coupling assembly. Knowledge of these clinically relevant forces can be used in later steps to modify, change, pause, reinitiate, and/or terminate the procedure or therapy so as to prevent damage or harm to the patient and/or the coupling assembly or other system components either automatically by the system or through user-initiated actions based on force information presented on the UI.

At step 1010 of FIG. 10, the method can optionally include providing an indication to the user regarding the clinically relevant forces acting against the treatment head and/or robotic arm during therapy. As described above, these forces can be the forces acting against the treatment head or arm accounting for buoyancy forces from submersion of the treatment head into the coupling assembly and coupling medium. In some embodiments, providing an indication of the forces can comprise displaying the forces to the user on a display. The display can include an indicator that conveys the amount of the force applied against the treatment head and/or robotic arm. This can include, for example, a color-coded system (e.g., green, yellow, orange, red, etc.), a system that indicates the force amount in words (e.g., "low", "medium", "high", etc.) or alternatively a system that displays or indicates the actual measured force. Other embodiments can include other visual indicators such as patterns or shapes. In some embodiments, this display of the force can also include an indicator or other feature that indicates either the direction of the force, or the plane and/or direction of the force with respect to the treatment head and/or robotic arm. For example, the display can indicate that the force is acting on the +/−X, Y, and/or Z planes of the treatment head and/or arm relative to an X,Y,Z coordinate system that can also be displayed to the user. Thus, the user can see the forces acting upon the treatment head and/or robotic arm(s) and also see the direction from which those forces are acting on the head/arm(s). Tactile and audible indicators can also be used to display or communicate clinically relevant forces.

At step 1012 of FIG. 10, the method can further include pausing, adjusting, limiting, reinitiating, or terminating treatment head movement or therapy delivery in response to measured or calculated forces that are excessive or exceed a safety threshold. In some implementations, each stage or level of force measurement can be associated with a threshold. For example, a force acting against the head/arm that is deemed "low" or falling within a "green" or "yellow" color code may result in no limitations being placed on movement of the head. This can be, for example, considered a "normal" mode of operation in which the head and/or robotic arm is free to move the treatment head in the given work-flow step, including as an example, to each target/focal location according to the treatment plan with no limitations placed on the speed of robotic arm movement or on steering, manipulating, or adjusting the degrees of freedom (pitch, roll, yaw, angle, or x, y or z location) of the treatment head or robotic arm.

In some implementations, the next level of forces applied against the head/arm, such as forces associated with a "medium" or "orange" color code level of force, may result in the system imparting moderate restrictions or limitations on head/arm movement. For example, a "medium" level of force may indicate that the system detects a collision or resistance between the head/arm and the patient/coupling assembly, but the measured force is not yet enough to harm the patient or the coupling assembly. In this instance, it may be desirable to limit the speed of movement of the head/arm, since rapid movements when a collision is present or imminent may result in harm to the system or patient occurring rapidly. In some examples, the system can be configured to automatically limit or prevent further movement in the direction of the detected forces when the detected forces are in the "medium" or "code orange" category of forces. For example, if a "medium" or "code orange" force is detected in the +X direction of the therapy probe/arm, then the system may restrict or limit movement of the head/arm in that direction.

In other embodiments, detection of the final or highest level of forces applied against the head may result in completely pausing, terminating, or stopping the therapy and/or all movement of the treatment head. This level of forces may be a determination or indication to the user that a major collision between the patient and the head/arm is occurring that may result in imminent harm or damage to the patient or the system. In one implementation, when the system detects or enters the "high" or "code red" level of forces, the system may immediately stop movement of the head/arm. In another embodiment, this event may include forcing an exit to the therapy session altogether. In another embodiment, the system may automatically "back off" or move the head in the opposite direction of the detected force so as to reduce or relieve the excessive forces that are being applied to the probe/arm. In another embodiment, the system can be configured to automatically remove or release all tension from the robotic positioning arm(s) (e.g., unlock the joints of the robotic arm), or to cause the arms to enter a manual manipulation mode where the weight of the therapy transducer is supported but no additional tension is applied to the robotic arm, and the user may be further allowed to "free drive" the treatment head and robot to a safe position. This allows a user to immediately manually move the probe and/or robotic arm(s) away from the collision site, such as away from the patient or the coupling assembly.

It should be noted that, during the course of performing the method steps of FIG. 10, any and/or all of the method steps can be repeated for subsequent treatment/focal locations or multiple treatment sessions in a single procedure session (e.g., multiple targets treated). So, in some examples, the method steps can be repeated for each subsequent treatment location of the treatment plan until the therapy or treatment is completed. The system can constantly or continuously monitor the forces acting against the head/arm (including accounting for buoyancy forces) and can indicate or alert to the user those forces, and the direction upon the probe from which those forces are acting. Additionally, the system can automatically adjust, limit, or pause therapy when forces become excessive to the point that harm to the patient or the system itself is a possibility.

As described above, force sensing and monitoring may be implemented for histotripsy systems and methods across histotripsy procedure work-flows as described in the following unlimited examples:

Example 1: In one embodiment, the histotripsy system is configured for force sensing and monitoring during "free drive" mode.

Example 2: In one embodiment, the histotripsy system is configured for force sensing and monitoring and use raw sensor readouts as an input for applying speed limits, visual indicators and notifications (where applicable), providing visual indicators and notifications and applying speed limits when defined feedback thresholds are exceeded.

In one embodiment, the histotripsy system is configured for force sensing and monitoring and use raw and/or compensated sensor values (e.g., buoyancy) when checking for overall safety force limits.

In one embodiment, the histotripsy system is configured for force sensing and monitoring and whenever speed limits are applied or "red/maximum" thresholds are reached, the system will allow motion away from the patient/coupling assembly.

In one embodiment, the histotripsy system is configured for force sensing and monitoring during the procedure, and the system software may have a dedicated flag in the configuration file to govern responses to a force fault or threshold event. This flag may be used to force a specific system response (e.g., trigger an emergency stop, etc.).

In one embodiment, the histotripsy system is configured for force sensing and monitoring during histotripsy therapy delivery, wherein the system software is designed to stop therapy and robot motion (if in motion) when a "red/maximum" force threshold is met and/or exceeded in the +/−x, +/−y, and/or +z directions, and the system may be further configured to check therapy status to confirm the pause in therapy delivery and if therapy stoppage can't be confirmed, the system may be configured for a soft emergency stop.

In one embodiment, the histotripsy system is configured for force sensing and monitoring during a histotripsy procedure, wherein the system software may display visual indicators including display of the treatment head and position of the imaging probe (e.g., translated out or in home position).

In one embodiment similar to above, the histotripsy system is configured for force sensing and monitoring, and wherein the visual indicators include a treatment head and associated direction of the force(s), as well as the UI ultrasound imaging pane highlighted with the relevant force state color ("green, "yellow", "orange", and/or "red").

In one embodiment similar to above wherein the software displays a text notification of "low", "medium" or "high resistance" in addition to the colored visual indicators or highlighted imaging panes.

In another example embodiment, wherein the system configured for force sensing/detection includes software features to command the robotic arm to a "ready pose" or "level treatment head pose", wherein the poses are utilized as a part of setup or service (no patient) and/or during clinical procedures (patient involved).

In one example, wherein the histotripsy system software is configured to allow the user to execute steps to set the water level (e.g., point of contact of the treatment head and acoustic coupling medium), including user interface buttons to verify the step is complete.

In another embodiment, the histotripsy system is configured for force sensing and monitoring wherein during commanded robot motion (via the space mouse) as a part of the targeting and localizing phase after the water level is set, the system software is designed to monitor force sensor values and apply buoyancy compensation, and to further monitor and notify users of force states and apply any defined speed or force limits.

In one embodiment, the histotripsy system is configured for force sensing and monitoring and allows the user to command the robot to move to various treatment plan locations/points, while monitoring and displaying force feedback indicators to the user to ensure the treatment plan minimizes the risk of collisions or force faults with the patient and/or coupling assembly. In addition to the force visual indicators, the treatment plan may be visualized through a 2D or 3D graphic and corresponding plan parameters.

In another example including above, the system is configured to allow "locking" the treatment plan, and robotically surveying around the plan in space, while monitoring/displaying force states with visual indicators and text notifications.

In another embodiment, the system is configured to execute the above features but while in "automated treatment" phase.

In one embodiment, the histotripsy system is configured for force sensing and monitoring during specific work-flow steps wherein controlled robotically-enabled ultrasound sweeps are executed with the system and treatment head (with the imaging probe translated out on the skin and/or near the skin), wherein the system is monitoring force before the sweep, during the sweep, and after the sweep, and wherein the thresholds established for safety may or may not vary across these steps.

In the above example, wherein the force is displayed to the user as a highlighted shape (e.g., box) encompassing one or more imaging panes, including ultrasound, MRI, CT, PET-CT, and/or combinations or fusions of, and/or wherein the displayed imaging data is multi-planar.

In general, the disclosure provides for or contemplates the following types/scenarios of forces acting against the treatment head and/or robotic arm:

Buoyancy forces—treatment head submerged/partially submerged in ultrasound medium and solutions for how to dynamically account for buoyancy forces.

Collision forces—physical collisions/interactions and applied force(s) between treatment head, robotic arm, patient, and/or coupling assembly Lack of force—treatment head isn't partially or fully submerged in coupling assembly.

Additionally, the forces sensing/measurement workflows described herein can include the following clinical and system/work-flow context:

Monitoring/watchdogging over forces while introducing treatment head into coupling assembly; and Once inside the coupling assembly, collisions/excessive force on patient anatomy (and potentially coupling assembly at same time)

From a system/work-flow side, this disclosure provides uniqueness in needing to target/localize with very large, high surface area and curved end-effectors (e.g., treatment heads) that can present challenges to safely positioning the system over the patient; and When force thresholds are met the need to provide safe options to react/respond to these force scenarios; and all the while accounting for base forces (buoyancy) to ensure thresholds aren't artificially exceeded when normally clinically acceptable.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of monitoring forces against an ultrasound treatment head, comprising:

submerging at least a portion of the ultrasound treatment head in a fluid reservoir filled with an acoustic coupling medium;

determining raw forces acting against the ultrasound treatment head;

determining a pose angle of the ultrasound treatment head within the acoustic coupling medium;

determining an insertion depth of the ultrasound treatment head within the acoustic coupling medium;

determining buoyancy forces applied by the acoustic coupling medium against the treatment head for the determined pose angle and insertion depth of the ultrasound treatment head;

determining clinically relevant forces acting against the ultrasound treatment head by subtracting the buoyancy forces from the raw forces; and adjusting ultrasound treatment head movement in response to clinically relevant forces that exceed at least one safety threshold.

2. The method of claim 1, wherein determining the raw forces acting against the ultrasound treatment head comprises measuring the raw forces with one or more force sensors disposed on or within the ultrasound treatment head.

3. The method of claim 1, wherein determining the raw forces acting against the ultrasound treatment head comprises measuring the raw forces with one or more force sensors disposed on or within a robotic positioning arm coupled to the ultrasound treatment head.

4. The method of claim 1, wherein the pose angle is determined by one or more processors operatively coupled to the ultrasound treatment head.

5. The method of claim 1, wherein the insertion depth is determined based on a surface level of the acoustic coupling medium.

6. The method of claim 1, wherein determining the buoyancy forces further comprises calculating the buoyancy forces with a model equation with best fit coefficients that uses the insertion depth and pose angle as inputs.

7. The method of claim 1, wherein the fluid reservoir comprises a coupling container placed on a patient.

8. The method of claim 1, wherein submerging the ultrasound treatment head comprises moving the ultrasound treatment head with at least one robotic positioning arm.

9. The method of claim 1, wherein determining buoyancy forces further comprises repeatedly or continuously determining buoyancy forces applied by the acoustic coupling medium against the ultrasound treatment head for the determined pose angle and insertion depth of the ultrasound treatment head.

10. The method of claim 1, wherein the buoyancy forces are determined in real time.

11. The method of claim 1, wherein the buoyancy forces are determined from a lookup table.

12. The method of claim 1, further comprising indicating the clinically relevant forces to a user.

13. The method of claim 1, further comprising providing a visual indicator of the clinically relevant forces to a user on a graphical user interface.

14. The method of claim 13, wherein the visual indicator indicates if the clinically relevant forces fall within a low range of forces, a medium range of forces, or a high range of forces.

15. The method of claim 12, wherein indicating further comprises displaying a color coded force indication system to the user.

16. The method of claim 12, wherein indicating further comprises displaying words that indicate to the user a level of the clinical relevant forces.

17. The method of claim 12, wherein indicating further comprises displaying the raw forces.

18. The method of claim 12, wherein indicating further comprises indicating a direction or location on the treatment head where the clinically relevant forces are sensed or measured.

19. The method of claim 1, wherein the at least one safety threshold comprises a moderate or medium safety threshold, and wherein adjusting treatment head movement further comprises limiting treatment head movement speed to a maximum movement speed.

20. The method of claim 1, wherein the at least one safety threshold comprises a moderate or medium safety threshold, and wherein adjusting treatment head movement further comprises limiting treatment head movement in the direction of the detected clinically relevant force that exceeds the moderate or medium safety threshold.

21. The method of claim 1, wherein the at least one safety threshold comprises a high or excessive safety threshold, and wherein adjusting treatment head movement further comprises terminating treatment head movement.

22. The method of claim 1, wherein the at least one safety threshold comprises a high or excessive safety threshold, and wherein adjusting treatment head movement further comprises moving the treatment head in the opposite direction of the clinically relevant force that exceeds the high or excessive safety threshold.

\* \* \* \* \*